United States Patent
Shelton, IV et al.

(10) Patent No.: US 11,748,924 B2
(45) Date of Patent: Sep. 5, 2023

(54) TIERED SYSTEM DISPLAY CONTROL BASED ON CAPACITY AND USER OPERATION

(71) Applicant: Cilag GmbH International, Zug (CH)

(72) Inventors: Frederick E. Shelton, IV, New Vienna, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/062,512

(22) Filed: Oct. 2, 2020

(65) Prior Publication Data

US 2022/0104897 A1 Apr. 7, 2022

(51) Int. Cl.
*G06T 11/20* (2006.01)
*G06F 3/01* (2006.01)
(Continued)

(52) U.S. Cl.
CPC .......... *G06T 11/206* (2013.01); *G06F 3/011* (2013.01); *G06F 3/048* (2013.01); *G06F 3/1423* (2013.01);
(Continued)

(58) Field of Classification Search
CPC ........ G06T 11/206; G06F 3/011; G06F 3/048; G06F 3/1423; G06F 11/3058; G09G 2360/04
(Continued)

(56) References Cited

U.S. PATENT DOCUMENTS 5,754,192 A * 5/1998 Sugaya .................. G06K 15/00
358/404
6,451,015 B1 9/2002 Rittman, III et al.
(Continued)

FOREIGN PATENT DOCUMENTS

CA 3089858 A1 8/2019
EP 2491872 A1 8/2012
(Continued)

OTHER PUBLICATIONS

U.S. Appl. No. 17/062,504, filed Oct. 2, 2021, Shelton, et al.
(Continued)

*Primary Examiner* — William A Beutel
(74) *Attorney, Agent, or Firm* — Condo Roccia Koptiw LLP

(57) ABSTRACT

A surgical hub may be configured to receive an image from a laparoscopic scope and surgical information from at least one surgical instrument. The surgical hub may be operatively connected to multiple displays such as a primary display and a secondary display. The surgical hub may generate visualization data for the primary display. The surgical hub may obtain a visualization control mode based on a visualization control parameter and may determine whether to generate a different set of visualization data for a secondary display based on the visualization control mode. When the visualization control mode supports multiple display capabilities, the surgical hub may generate the visualization data specifically for the secondary display. When the visualization control mode does not support multiple display capabilities, the surgical hub may send the same the visualization data for display at the secondary display as the primary display.

20 Claims, 46 Drawing Sheets

(51) Int. Cl.
*G06F 3/048* (2013.01)
*G06F 3/14* (2006.01)
*G06F 11/30* (2006.01)

(52) U.S. Cl.
CPC ..... *G06F 11/3058* (2013.01); *G09G 2360/04* (2013.01)

(58) Field of Classification Search
USPC ........................................................ 345/1.1
See application file for complete search history.

(56) References Cited

U.S. PATENT DOCUMENTS

| | | |
|---|---|---|
| 6,847,336 B1 | 1/2005 | Lemelson et al. |
| 7,032,798 B2 | 4/2006 | Whitman et al. |
| 7,164,940 B2 | 1/2007 | Hareyama et al. |
| 7,496,395 B2 | 2/2009 | Serov et al. |
| 7,667,592 B2 | 2/2010 | Ohyama et al. |
| 7,670,334 B2 | 3/2010 | Hueil et al. |
| 7,803,151 B2 | 9/2010 | Whitman |
| 7,833,219 B2 | 11/2010 | Tashiro et al. |
| 7,839,354 B2 * | 11/2010 | Moriwaki ............ G06F 3/1454 345/1.1 |
| 8,157,145 B2 | 4/2012 | Shelton, IV et al. |
| 8,255,045 B2 | 8/2012 | Gharib et al. |
| 8,476,227 B2 | 7/2013 | Kaplan et al. |
| 8,523,043 B2 | 9/2013 | Ullrich et al. |
| 8,608,045 B2 | 12/2013 | Smith et al. |
| 8,851,354 B2 | 10/2014 | Swensgard et al. |
| 8,918,207 B2 | 12/2014 | Prisco |
| 8,960,519 B2 | 2/2015 | Whitman et al. |
| 9,011,427 B2 | 4/2015 | Price et al. |
| 9,072,535 B2 | 7/2015 | Shelton, IV et al. |
| 9,123,155 B2 | 9/2015 | Cunningham et al. |
| 9,250,172 B2 | 2/2016 | Harris et al. |
| 9,283,054 B2 | 3/2016 | Morgan et al. |
| 9,345,481 B2 | 5/2016 | Hall et al. |
| 9,516,239 B2 | 12/2016 | Blanquart et al. |
| 9,538,962 B1 | 1/2017 | Hannaford et al. |
| 9,582,055 B2 | 2/2017 | De Jong et al. |
| 9,743,016 B2 | 8/2017 | Nestares et al. |
| 9,777,913 B2 | 10/2017 | Talbert et al. |
| 9,913,642 B2 | 3/2018 | Leimbach et al. |
| 10,492,783 B2 | 12/2019 | Shelton, IV et al. |
| 10,639,037 B2 | 5/2020 | Shelton, IV et al. |
| 10,695,081 B2 | 6/2020 | Shelton, IV et al. |
| 10,881,399 B2 | 1/2021 | Shelton, et al. |
| 10,912,567 B2 | 2/2021 | Shelton, IV et al. |
| 10,987,178 B2 | 4/2021 | Shelton, IV et al. |
| 11,123,074 B2 | 9/2021 | Adams et al. |
| 11,185,331 B2 | 11/2021 | Adams et al. |
| 11,284,963 B2 | 3/2022 | Shelton, IV et al. |
| 2004/0108825 A1 | 6/2004 | Lee et al. |
| 2005/0033117 A1 | 2/2005 | Ozaki et al. |
| 2005/0128184 A1 | 6/2005 | Mcgreevy |
| 2005/0134525 A1 | 6/2005 | Tanghe et al. |
| 2005/0206583 A1 | 9/2005 | Lemelson et al. |
| 2006/0004286 A1 | 1/2006 | Chang et al. |
| 2006/0076385 A1 | 4/2006 | Etter et al. |
| 2006/0082542 A1 | 4/2006 | Morita et al. |
| 2006/0184160 A1 | 8/2006 | Ozaki et al. |
| 2006/0273135 A1 | 12/2006 | Beetel |
| 2007/0013336 A1 | 1/2007 | Nowlin et al. |
| 2007/0055304 A1 | 3/2007 | Whitman |
| 2007/0151390 A1 | 7/2007 | Blumenkranz et al. |
| 2007/0173689 A1 * | 7/2007 | Ozaki .................... A61B 1/042 600/111 |
| 2007/0225690 A1 | 9/2007 | Sekiguchi et al. |
| 2008/0319275 A1 | 12/2008 | Chiu et al. |
| 2009/0046146 A1 | 2/2009 | Hoyt |
| 2009/0090763 A1 | 4/2009 | Zemlok et al. |
| 2009/0128084 A1 | 5/2009 | Johnson et al. |
| 2010/0096431 A1 | 4/2010 | Smith et al. |
| 2011/0181394 A1 | 7/2011 | Blair |
| 2012/0069131 A1 | 3/2012 | Abelow |
| 2012/0116365 A1 | 5/2012 | Price et al. |
| 2012/0138658 A1 | 6/2012 | Ullrich et al. |
| 2012/0182409 A1 | 7/2012 | Moriyama et al. |
| 2012/0211542 A1 | 8/2012 | Racenet |
| 2012/0248167 A1 | 10/2012 | Flanagan et al. |
| 2013/0116218 A1 | 5/2013 | Kaplan et al. |
| 2013/0197531 A1 | 8/2013 | Boukhny et al. |
| 2013/0245456 A1 | 9/2013 | Ferguson, Jr. et al. |
| 2014/0018637 A1 | 1/2014 | Bennett et al. |
| 2014/0066700 A1 | 3/2014 | Wilson et al. |
| 2014/0087999 A1 | 3/2014 | Kaplan et al. |
| 2014/0160002 A1 * | 6/2014 | Dent ................... G06F 3/1431 345/156 |
| 2014/0160259 A1 | 6/2014 | Blanquart et al. |
| 2014/0160260 A1 | 6/2014 | Blanquart et al. |
| 2014/0160318 A1 | 6/2014 | Blanquart et al. |
| 2014/0160319 A1 | 6/2014 | Nestares et al. |
| 2014/0166728 A1 | 6/2014 | Swayze et al. |
| 2014/0201126 A1 | 7/2014 | Zadeh et al. |
| 2014/0214311 A1 | 7/2014 | Stevens et al. |
| 2014/0263541 A1 | 9/2014 | Leimbach et al. |
| 2014/0263551 A1 | 9/2014 | Hall et al. |
| 2014/0263552 A1 | 9/2014 | Hall et al. |
| 2014/0267655 A1 | 9/2014 | Richardson et al. |
| 2014/0268860 A1 | 9/2014 | Talbert et al. |
| 2015/0125447 A1 | 5/2015 | Heider |
| 2015/0157416 A1 | 6/2015 | Andersson |
| 2015/0182220 A1 | 7/2015 | Yates et al. |
| 2015/0223890 A1 | 8/2015 | Miller et al. |
| 2015/0342621 A1 | 12/2015 | Jackson, III |
| 2016/0066915 A1 | 3/2016 | Baber et al. |
| 2016/0066916 A1 | 3/2016 | Overmyer et al. |
| 2016/0100839 A1 | 4/2016 | Marczyk et al. |
| 2016/0148052 A1 | 5/2016 | Tsuda et al. |
| 2016/0154620 A1 * | 6/2016 | Tsuda .................. G02B 27/017 345/633 |
| 2016/0171330 A1 | 6/2016 | Mentese et al. |
| 2016/0171947 A1 | 6/2016 | Chen |
| 2016/0249019 A1 | 9/2016 | Savage et al. |
| 2016/0253472 A1 | 9/2016 | Pedersen et al. |
| 2016/0256156 A1 | 9/2016 | Shelton, IV et al. |
| 2016/0256184 A1 | 9/2016 | Shelton, IV et al. |
| 2016/0265938 A1 | 9/2016 | Hryb et al. |
| 2016/0332296 A1 | 11/2016 | Kurnianto |
| 2017/0000551 A1 | 1/2017 | Ward et al. |
| 2017/0000575 A1 | 1/2017 | Griffiths et al. |
| 2017/0086914 A1 | 3/2017 | Wiener et al. |
| 2017/0172381 A1 | 6/2017 | Morimoto et al. |
| 2017/0199632 A1 | 7/2017 | Ohmura |
| 2017/0227754 A1 | 8/2017 | Huang |
| 2017/0249431 A1 | 8/2017 | Shelton, IV et al. |
| 2017/0272838 A1 | 9/2017 | Glazer et al. |
| 2017/0296169 A1 | 10/2017 | Yates et al. |
| 2017/0296178 A1 | 10/2017 | Miller et al. |
| 2017/0296213 A1 | 10/2017 | Swensgard et al. |
| 2017/0323062 A1 | 11/2017 | Djajadiningrat et al. |
| 2017/0333033 A1 | 11/2017 | Valentine et al. |
| 2018/0032130 A1 | 2/2018 | Meglan et al. |
| 2018/0098049 A1 | 4/2018 | Sugano et al. |
| 2018/0098768 A1 | 4/2018 | Zhang et al. |
| 2018/0165051 A1 * | 6/2018 | Kim ...................... G09G 5/006 |
| 2018/0197624 A1 | 7/2018 | Robaina et al. |
| 2018/0256025 A1 | 9/2018 | Yi et al. |
| 2018/0329504 A1 | 11/2018 | Ziraknejad et al. |
| 2018/0353186 A1 | 12/2018 | Mozdzierz et al. |
| 2018/0360449 A1 | 12/2018 | Shelton, IV et al. |
| 2018/0360452 A1 | 12/2018 | Shelton, IV et al. |
| 2018/0360460 A1 | 12/2018 | Mozdzierz et al. |
| 2019/0000446 A1 | 1/2019 | Shelton, IV et al. |
| 2019/0000464 A1 | 1/2019 | Shelton, IV et al. |
| 2019/0000478 A1 | 1/2019 | Messerly et al. |
| 2019/0020420 A1 | 1/2019 | Zocher et al. |
| 2019/0099180 A1 | 4/2019 | Leimbach et al. |
| 2019/0104919 A1 * | 4/2019 | Shelton, IV .......... A61B 90/361 |
| 2019/0117070 A1 | 4/2019 | Muhsin et al. |
| 2019/0125361 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0183591 A1 | 6/2019 | Johnson et al. |

(56) References Cited

U.S. PATENT DOCUMENTS

| | | |
|---|---|---|
| 2019/0200844 A1 | 7/2019 | Shelton, IV et al. |
| 2019/0200905 A1 | 7/2019 | Shelton et al. |
| 2019/0200906 A1 | 7/2019 | Shelton et al. |
| 2019/0200981 A1 | 7/2019 | Harris et al. |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201029 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201044 A1 | 7/2019 | Shelton, IV et al. |
| 2019/0201102 A1 | 7/2019 | Shelton, et al. |
| 2019/0201104 A1 | 7/2019 | Shelton, et al. |
| 2019/0201115 A1 | 7/2019 | Shelton, IV et al. |
| 2019/0201119 A1 | 7/2019 | Harris et al. |
| 2019/0201122 A1 | 7/2019 | Shelton, IV et al. |
| 2019/0201129 A1 | 7/2019 | Shelton, et al. |
| 2019/0201136 A1 | 7/2019 | Shelton et al. |
| 2019/0201137 A1 | 7/2019 | Shelton, et al. |
| 2019/0201140 A1 | 7/2019 | Yates et al. |
| 2019/0201141 A1 | 7/2019 | Shelton, IV et al. |
| 2019/0201144 A1 | 7/2019 | Shelton, IV et al. |
| 2019/0201146 A1 | 7/2019 | Shelton, IV et al. |
| 2019/0204201 A1 | 7/2019 | Shelton, et al. |
| 2019/0205001 A1 | 7/2019 | Messerly et al. |
| 2019/0206003 A1 | 7/2019 | Harris et al. |
| 2019/0206050 A1 | 7/2019 | Yates et al. |
| 2019/0206555 A1 | 7/2019 | Morgan et al. |
| 2019/0206562 A1 | 7/2019 | Shelton, et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV et al. |
| 2019/0206569 A1 | 7/2019 | Shelton, et al. |
| 2019/0250873 A1 | 8/2019 | Blume et al. |
| 2019/0314015 A1 | 10/2019 | Shelton, IV et al. |
| 2019/0388137 A1 | 12/2019 | Henrywood, et al. |
| 2020/0030044 A1 | 1/2020 | Wang et al. |
| 2020/0046208 A1 | 2/2020 | Kasai et al. |
| 2020/0078078 A1 | 3/2020 | Henderson et al. |
| 2020/0078079 A1 | 3/2020 | Morgan et al. |
| 2020/0090412 A1* | 3/2020 | Harviainen .......... G02B 27/017 |
| 2020/0120308 A1 | 4/2020 | Mcmillan et al. |
| 2020/0162664 A1 | 5/2020 | Maeda et al. |
| 2020/0188057 A1 | 6/2020 | Brandao et al. |
| 2020/0214571 A1 | 7/2020 | Bradbury et al. |
| 2020/0219319 A1* | 7/2020 | Lashmar ................. H04L 63/10 |
| 2020/0281790 A1 | 9/2020 | Augustine et al. |
| 2020/0342228 A1 | 10/2020 | Prevrhal et al. |
| 2020/0350063 A1 | 11/2020 | Thornton et al. |
| 2020/0356255 A1* | 11/2020 | Qing .................. G06F 3/04883 |
| 2020/0405304 A1 | 12/2020 | Mozdzierz et al. |
| 2020/0405439 A1 | 12/2020 | Shelton, IV et al. |
| 2021/0007574 A1 | 1/2021 | Hirayama et al. |
| 2021/0015461 A1* | 1/2021 | Karasawa .......... G01S 7/52053 |
| 2021/0060243 A1 | 3/2021 | Dave et al. |
| 2021/0077110 A1 | 3/2021 | Adams et al. |
| 2021/0077111 A1 | 3/2021 | Adams et al. |
| 2021/0077112 A1 | 3/2021 | Adams et al. |
| 2021/0113269 A1 | 4/2021 | Vilsmeier et al. |
| 2021/0137581 A1 | 5/2021 | Reid et al. |
| 2021/0169578 A1 | 6/2021 | Calloway et al. |
| 2021/0196384 A1 | 7/2021 | Shelton, IV et al. |
| 2021/0196423 A1 | 7/2021 | Shelton, IV et al. |
| 2021/0196425 A1 | 7/2021 | Shelton, IV et al. |
| 2021/0205027 A1 | 7/2021 | Leist |
| 2021/0240279 A1 | 8/2021 | Harviainen et al. |
| 2021/0307833 A1 | 10/2021 | Farley et al. |
| 2021/0401533 A1 | 12/2021 | Im |
| 2022/0022982 A1 | 1/2022 | Hares et al. |
| 2022/0104694 A1 | 4/2022 | Shelton, IV et al. |
| 2022/0104713 A1 | 4/2022 | Shelton, IV |
| 2022/0104765 A1 | 4/2022 | Shelton, IV et al. |
| 2022/0104806 A1 | 4/2022 | Shelton, IV et al. |
| 2022/0104807 A1 | 4/2022 | Shelton, IV et al. |
| 2022/0104813 A1 | 4/2022 | Shelton, IV et al. |
| 2022/0104814 A1 | 4/2022 | Shelton, IV et al. |
| 2022/0104820 A1 | 4/2022 | Shelton, IV et al. |
| 2022/0104821 A1 | 4/2022 | Shelton, IV et al. |
| 2022/0104822 A1 | 4/2022 | Shelton, IV et al. |
| 2022/0104843 A1 | 4/2022 | Shelton, IV et al. |
| 2022/0104867 A1 | 4/2022 | Shelton, IV et al. |
| 2022/0104889 A1 | 4/2022 | Shelton, IV et al. |
| 2022/0104896 A1 | 4/2022 | Shelton, IV et al. |
| 2022/0104908 A1 | 4/2022 | Shelton, IV et al. |
| 2022/0104910 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0108783 A1 | 4/2022 | Shelton, IV et al. |
| 2022/0108788 A1 | 4/2022 | Shelton, IV et al. |
| 2022/0108789 A1 | 4/2022 | Shelton, IV et al. |
| 2022/0246287 A1 | 8/2022 | Dawson et al. |

FOREIGN PATENT DOCUMENTS

| | | | |
|---|---|---|---|
| EP | 2659852 A2 | 11/2013 | |
| EP | 3412225 A1 | 12/2018 | |
| EP | 3449800 A1 | 3/2019 | |
| EP | 3506273 A1 | 7/2019 | |
| EP | 3506299 A1 | 7/2019 | |
| EP | 3628207 A1 | 4/2020 | |
| KR | 20010001630 A * | 1/2001 | ............... G09G 3/20 |
| WO | 2015125447 A1 | 8/2015 | |
| WO | 2016171947 A1 | 10/2016 | |
| WO | WO 2019-130108 A1 | 7/2019 | |
| WO | 2020101283 A1 | 5/2020 | |
| WO | 2020154351 A1 | 7/2020 | |

OTHER PUBLICATIONS

U.S. Appl. No. 17/062,508, filed Oct. 2, 2021, Shelton, et al.
U.S. Appl. No. 17/062,509, filed Oct. 2, 2021, Shelton, et al.
U.S. Appl. No. 17/062,507, filed Oct. 2, 2021, Shelton, et al.
U.S. Appl. No. 16/729,747, filed Dec. 31, 2019, Ethicon LLC.
U.S. Appl. No. 16/729,778, filed Dec. 31, 2019, Ethicon LLC.
U.S. Appl. No. 16/729,807, filed Dec. 31, 2019, Ethicon LLC.
ALSOS, "Interaction Techniques for Using Handhelds and PCs Together in a Clinical Setting", Dept of Computer and Information Science; Norwegian University of Science and Technology, Oct. 14-18, 2006, 10 pages.
"FPGA Fundamentals", https://www.ni.com/en-us.html, Jun. 17, 2020, accessed Sep. 8, 2020, 9 pages.
Google scholar search, Jun. 17, 2022.
Qamar, Rahil, "Semantic Mapping of Clinical Model Data To Biomedical Terminologies To Facilitate Interoperability", A these submitted to the University of Manchester, 2008, 260 pages.
George Slade, "The Fast Fourier Transform in Hardware: A Tutorial Based on an FPGA Implementation", http://web.mit.edu/, Mar. 21, 2013, accessed Sep. 8, 2020, 28 pages.

* cited by examiner

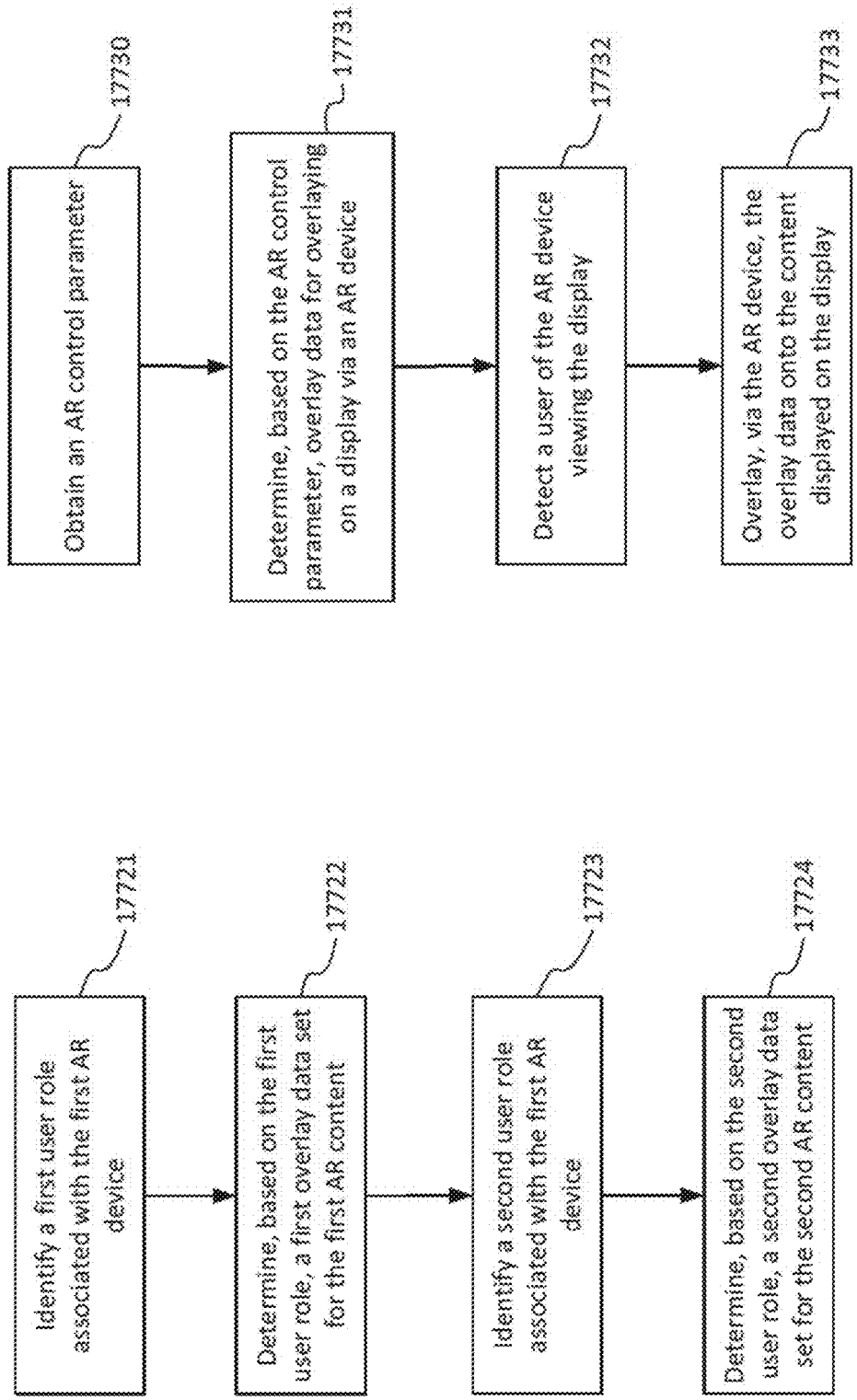

TIERED SYSTEM DISPLAY CONTROL BASED ON CAPACITY AND USER OPERATION

CROSS-REFERENCE TO RELATED APPLICATIONS

This application is related to the following, filed contemporaneously, the contents of each of which are incorporated by reference herein:

Ser. No. 17/062,504, titled METHOD FOR OPERATING TIERED OPERATION MODES IN A SURGICAL SYSTEM;

Ser. No. 17/062,508, titled COOPERATIVE SURGICAL DISPLAYS;

Ser. No. 17/062,509, titled INTERACTIVE INFORMATION OVERLAY ON MULTIPLE SURGICAL DISPLAYS; and Ser. No. 17/062,507, entitled COMMUNICATION CONTROL OPTIONS FOR A SURGEON CONTROLLED SECONDARY DISPLAY AND PRIMARY DISPLAY.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

A surgical hub may be configured to receive an image from a laparoscopic scope and surgical information from at least one surgical instrument. The surgical hub may be operatively connected to multiple displays such as a primary display and a secondary display. The surgical hub may generate visualization data for the primary display. The surgical hub may obtain a visualization control mode based on a visualization control parameter, and may determine whether to generate a different set of visualization data for a secondary display based on the visualization control mode. When the visualization control mode supports multiple display capabilities, the surgical hub may generate the visualization data specifically for the secondary display. When the visualization control mode does not support multiple display capabilities, the surgical hub may send the same the visualization data for display at the secondary display as the primary display. The visualization data may be generated by receiving data from multiple smart surgical devices, and combining the received data for displaying on both the primary and secondary displays.

For example, the surgical hub may receive an indication of changing the visualization control mode to an updated visualization control mode. The surgical hub may generate and send visualization data to the primary display and/or the secondary display in accordance with the updated visualization control mode. For example, based on updated visualization control mode, the surgical hub may generate and send visualization data for display to the primary display and a different set of visualization data for display to the secondary display. In an example visualization control mode that supports contactless control, the surgical hub may generate the visualization data based on a contactless control parameter such as user motions, user's head orientation relative to a monitor, user hand gesture(s), and/or user voice activation. In an example visualization control mode that supports augmented reality, the surgical hub may generate overlay information for overlaying on the primary display via the secondary display.

In various examples, the visualization control parameter may include one or more of available memory, available data bandwidth, heat generated by the surgical hub, heat generated by the secondary display, power capacity associated with the surgical hub, power capacity associated with an operating room, power capacity associated with a medical facility, a power usage, a balance of the power consumption to at least one attached system, processor utilization, and/or memory utilization. The visualization control parameter may include one or more of a subscription level associated with surgical display; a user preference associated with surgical display; a hardware capability associated with the surgical hub, the primary display and the secondary display; a software capability associated with the surgical hub, the primary display and the secondary display; or an indication from a tiered control system.

For example, the visualization control parameter(s) may include an indication from a tiered system. The tiered system may scale the display capabilities and interactive display control capabilities and/or the like, based on the available data bandwidth, power capacity and usage, processor and memory utilization, and/or internal or attached systems. The tiered system may determine max display and interactive display control capabilities the surgical hub may operate under.

BRIEF DESCRIPTION OF THE DRAWINGS

FIG. 45 shows an example flow of a hub operating under a visualization control mode that support role-based AR capabilities.

FIG. 46 shows an example flow of a hub operating under a visualization control mode with AR capabilities that support overlays on various displays.

DETAILED DESCRIPTION

Applicant of the present application owns the following U.S. patent applications, filed contemporaneously, each of which is herein incorporated by reference in its entirety:

U.S. patent application Ser. No. 16/209,416, entitled "METHOD OF HUB COMMUNICATION, PROCESSING, DISPLAY, AND CLOUD ANALYTICS," filed Dec. 4, 2018;

U.S. patent application Ser. No. 15/940,671, entitled "SURGICAL HUB SPATIAL AWARENESS TO DETERMINE DEVICES IN OPERATING THEATER," filed Mar. 29, 2018;

U.S. patent application Ser. No. 16/182,269 entitled "IMAGE CAPTURING OF THE AREAS OUTSIDE THE ABDOMEN TO IMPROVE PLACEMENT AND CONTROL OF A SURGICAL DEVICE IN USE," filed Nov. 6, 2018;

U.S. patent application Ser. No. 16/729,747 entitled "DYNAMIC SURGICAL VISUALIZATION SYSTEMS," filed Dec. 31, 2019;

U.S. patent application Ser. No. 16/729,778 entitled "SYSTEM AND METHOD FOR DETERMINING, ADJUSTING, AND MANAGING RESECTION MARGIN ABOUT A SUBJECT TISSUE," filed Dec. 31, 2019;

U.S. patent application Ser. No. 16/729,807 entitled METHOD OF USING IMAGING DEVICES IN SURGERY, filed Dec. 31, 2019;

U.S. patent application Ser. No. 15/940,654, entitled SURGICAL HUB SITUATIONAL AWARENESS, filed Mar. 29, 2018;

U.S. patent application Ser. No. 15/940,671, titled SURGICAL HUB SPATIAL AWARENESS TO DETERMINE DEVICES IN OPERATING THEATER, which was filed on Mar. 29, 2018;

U.S. patent application Ser. No. 15/940,704, titled USE OF LASER LIGHT AND RED-GREEN-BLUE COLORATION TO DETERMINE PROPERTIES OF BACK SCATTERED LIGHT, which was filed on Mar. 29, 2018;

U.S. patent application Ser. No. 16/182,290, entitled "SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION," filed Nov. 6, 2018;

U.S. Pat. No. 9,011,427, entitled SURGICAL INSTRUMENT WITH SAFETY GLASSES, issued on Apr. 21, 2015;

U.S. Pat. No. 9,123,155, titled APPARATUS AND METHOD FOR USING AUGMENTED REALITY VISION SYSTEM IN SURGICAL PROCEDURES, which issued on Sep. 1, 2015;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018; and U.S. patent application Ser. No. 16/182,246, titled ADJUSTMENTS BASED ON AIRBORNE PARTICLE PROPERTIES, filed Nov. 6, 2018.

A surgical hub may have cooperative interactions with one of more means of displaying the image from the laparoscopic scope and information from one of more other smart devices. The hub may have the capacity of interacting with these multiple displays using an algorithm or control program that enables the combined display and control of the data distributed across the displays in communication with the hub.

Figure 1:
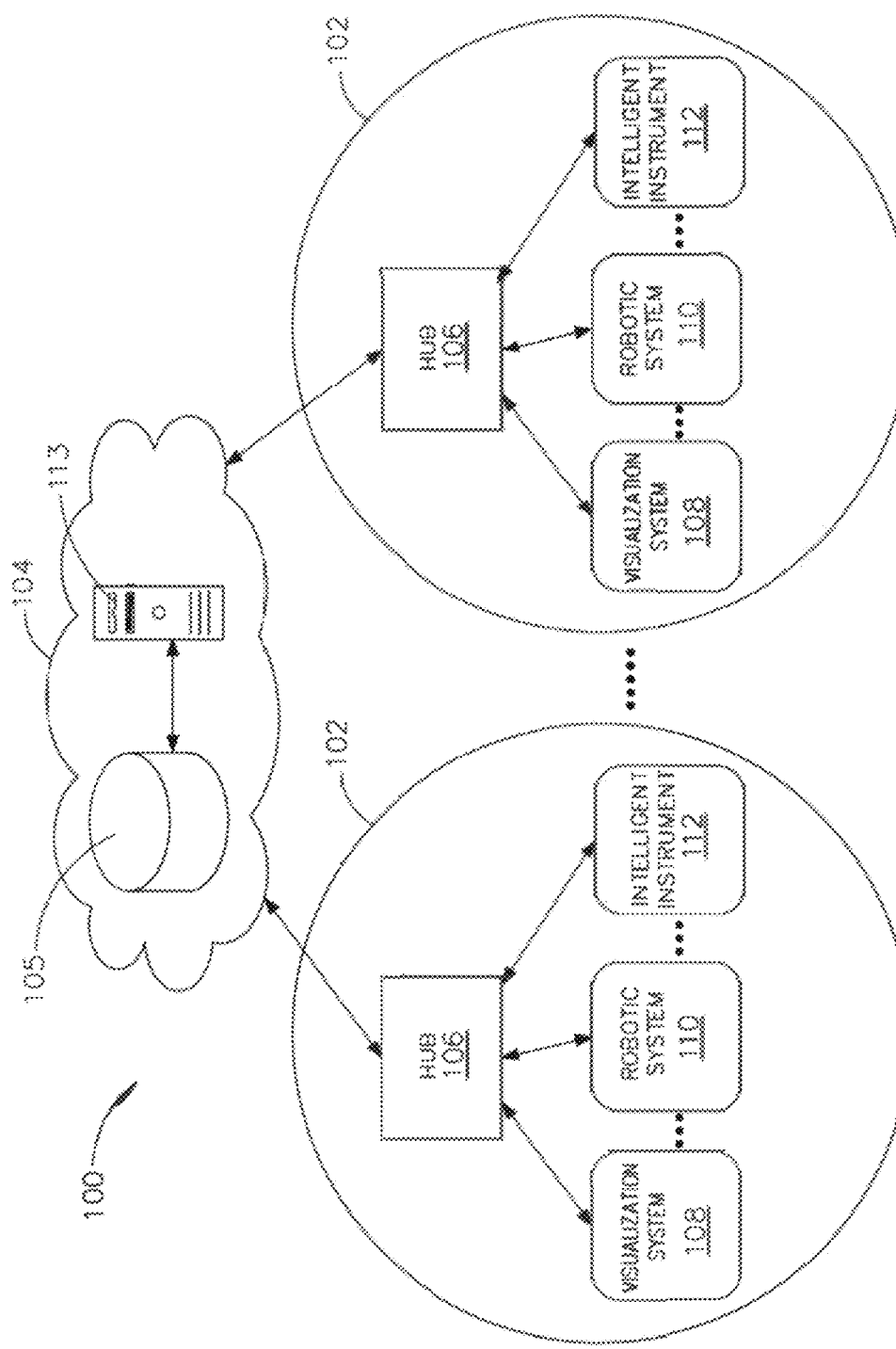
FIG. 1 is a block diagram of a computer-implemented interactive surgical system.

Referring to FIG. 1, a computer-implemented interactive surgical system 100 may include one or more surgical systems 102 and a cloud-based system (e.g., the cloud 104 that may include a remote server 113 coupled to a storage device 105). Each surgical system 102 may include at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
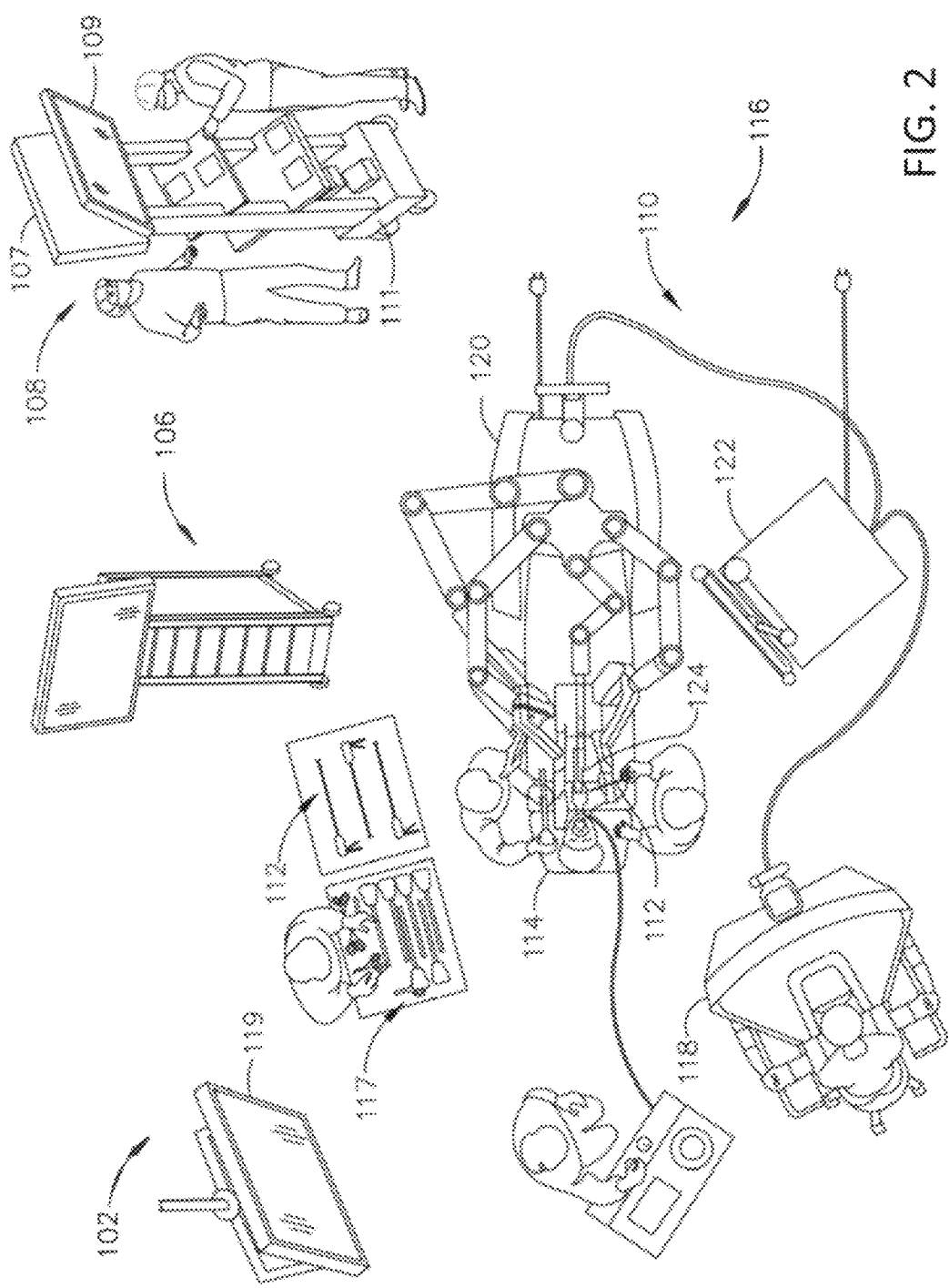
FIG. 2 shows an example surgical system being used to perform a surgical procedure in an operating room.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described under the heading "Advanced Imaging Acquisition Module" in US. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 may also be configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1 (U.S. patent application Ser. No. 16/209, 385), tided METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Patent Application Publication No. US 2019-0200844 A1 (U.S. patent application Ser. No. 16/209,385), tided METHOD OF HUB COMMUNICATION, PROCESSING, STORAGE AND DISPLAY, filed Dec. 4, 2018, the disclosure of which is herein incorporated by reference in its entirety, for example.

FIG. 2 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 3:
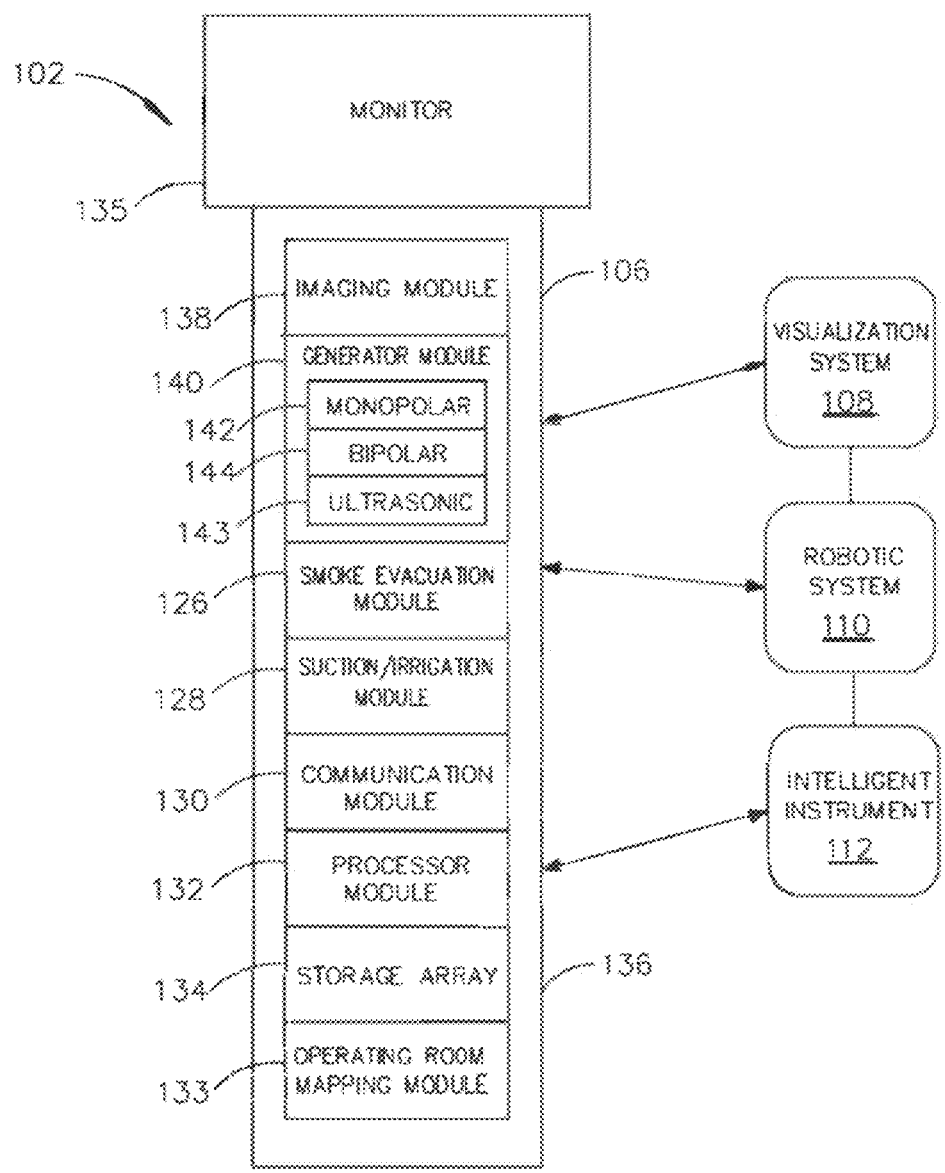
FIG. 3 shows an example surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, a storage array 134, and an operating-room mapping module 133. In certain aspects, as illustrated in FIG. 3, the hub 106 further includes a smoke evacuation module 126 and/or a suction/irrigation module 128. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines. Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line is a first fluid line and a second fluid line extends from the remote surgical site to a suction and irrigation module slidably received in the hub enclosure. In one aspect, the hub enclosure comprises a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 146. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

Figure 4:
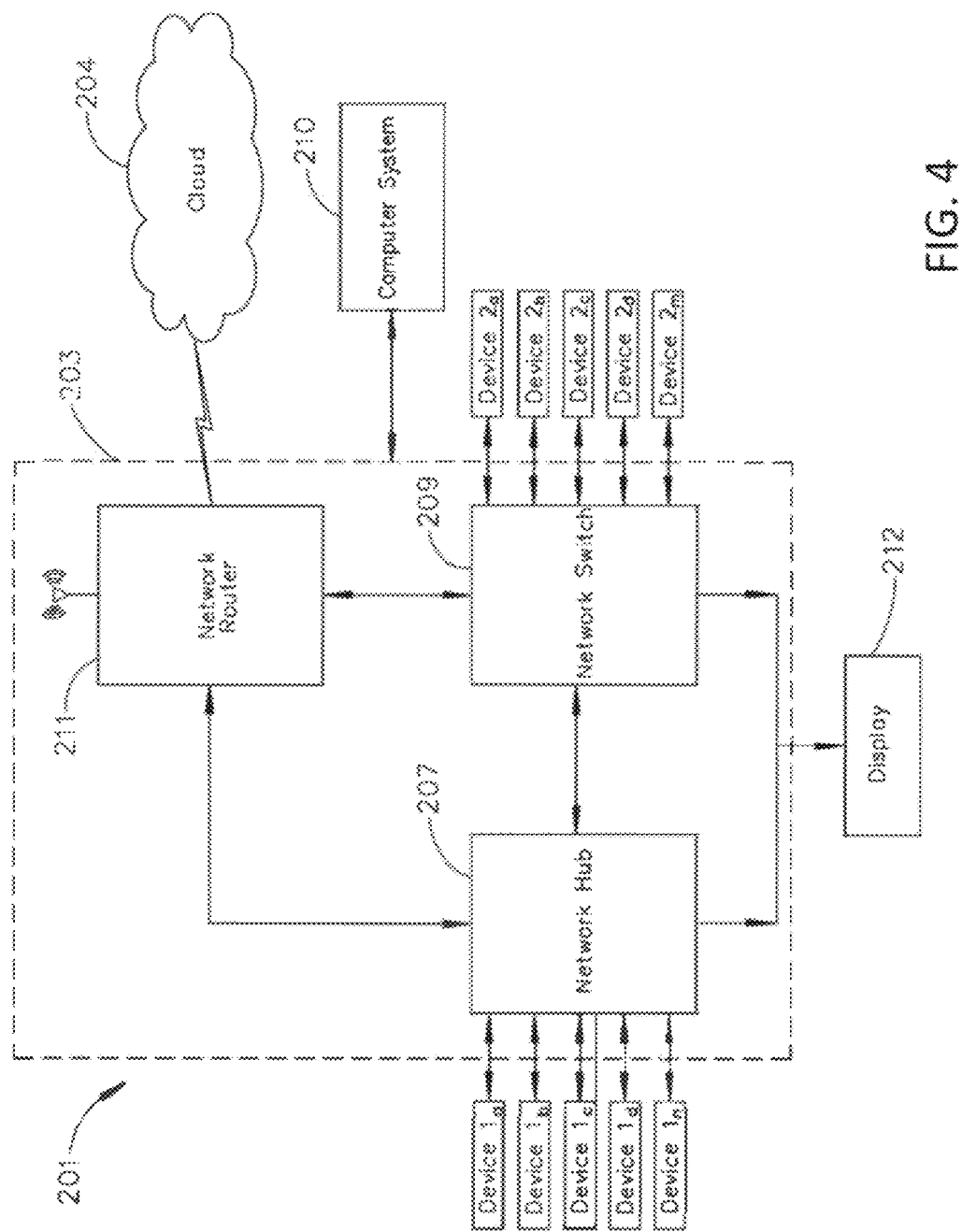
FIG. 4 illustrates a surgical data network having a communication hub configured to connect modular devices located in one or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1*a*-1*n*/2*a*-2*m* to the cloud. Any one of or all of the devices 1*a*-1*n*/2*a*-2*m* coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services-such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1*a*-1*n*/2*a*-2*m*, the surgical data network can provide improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathology, such as the effects of diseases, using the cloud-based computing to examine data including images of samples of body tissue for diagnostic purposes. This may include localization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

The operating theater devices 1*a*-1*n* may be connected to the modular communication hub 203 over a wired channel or a wireless channel depending on the configuration of the devices 1*a*-1*n* to a network hub. The network hub 207 may be implemented, in one aspect, as a local network broadcast device that works on the physical layer of the Open System Interconnection (OSI) model. The network hub may provide connectivity to the devices 1*a*-1*n* located in the same operating theater network. The network hub 207 may collect data in the form of packets and sends them to the router in half duplex mode. The network hub 207 may not store any media access control/Internet Protocol (MAC/IP) to transfer the device data. Only one of the devices 1*a*-1*n* can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions, but having all information broadcast to multiple ports can be a security risk and cause bottlenecks.

The operating theater devices 2*a*-2*m* may be connected to a network switch 209 over a wired channel or a wireless channel. The network switch 209 works in the data link layer of the OSI model. The network switch 209 may be a multicast device for connecting the devices 2*a*-2*m* located in the same operating theater to the network. The network switch 209 may send data in the form of frames to the network router 211 and works in full duplex mode. Multiple devices 2*a*-2*m* can send data at the same time through the network switch 209. The network switch 209 stores and uses MAC addresses of the devices 2*a*-2*m* to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1*a*-1*n*/2*a*-2*m*. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In examples, the operating theater devices 1*a*-1*n*/2*a*-2*m* may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1*a*-1*n*/2*a*-2*m* may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
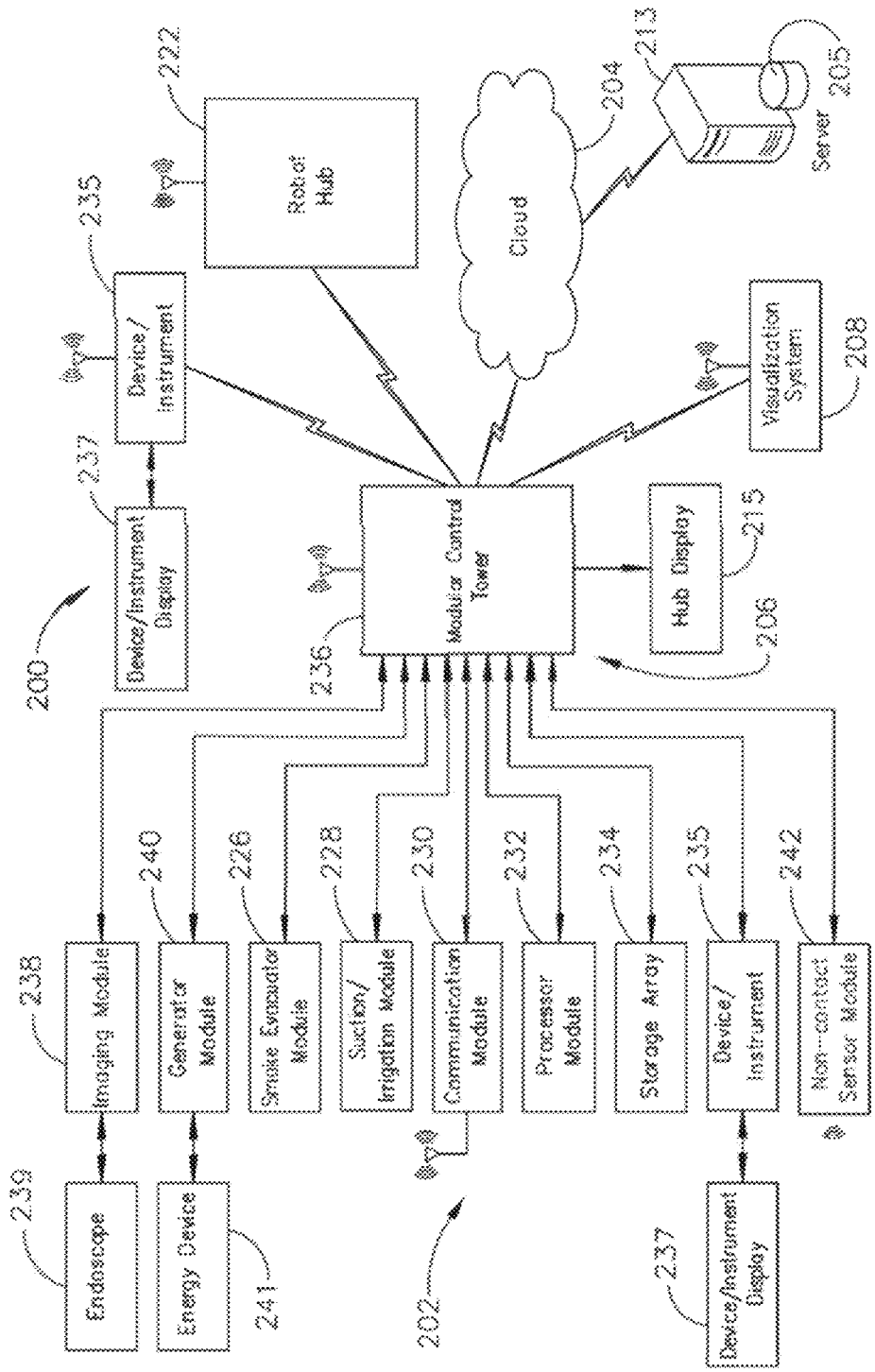
FIG. 5 illustrates an example computer-implemented interactive surgical system.
Figure 6:
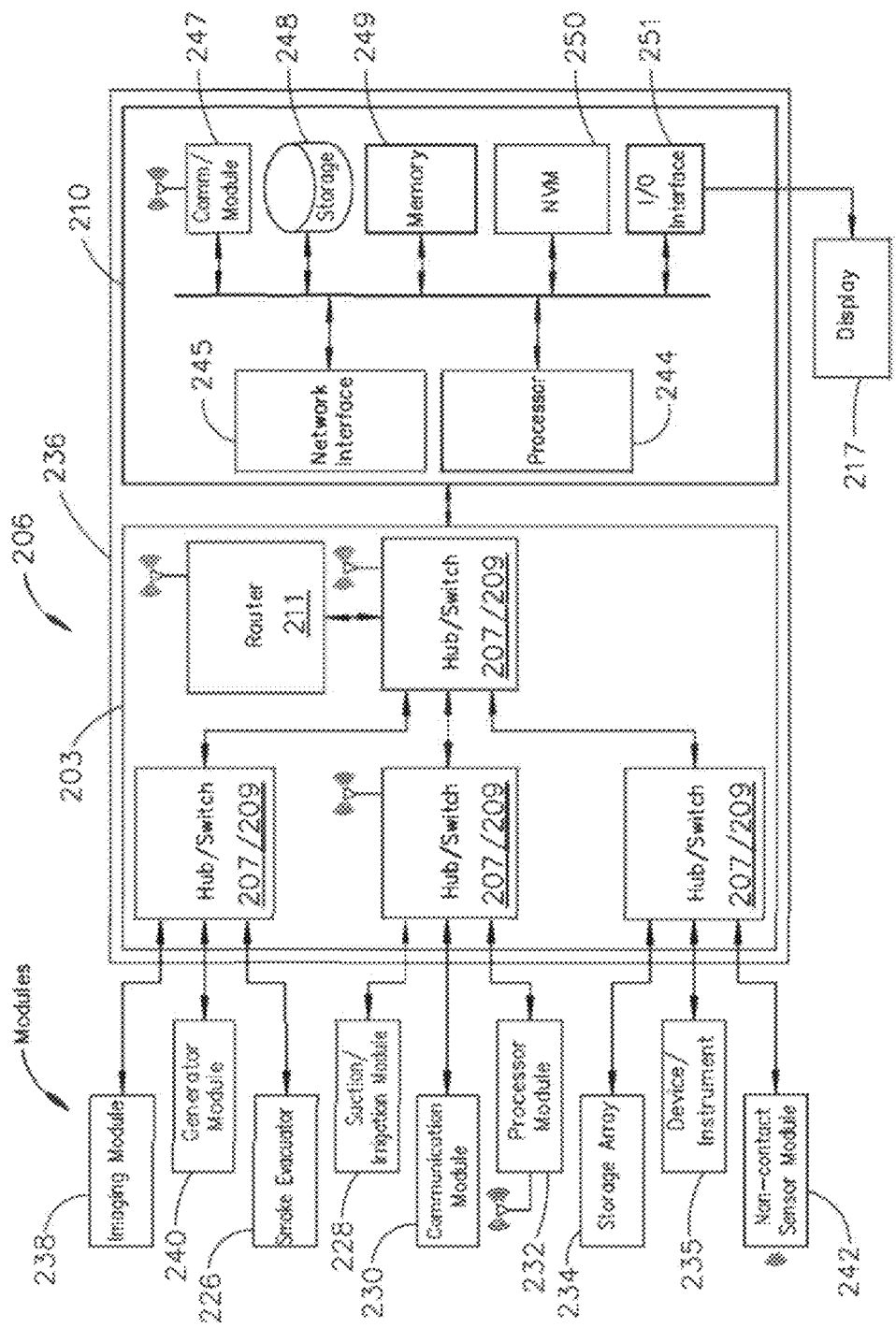
FIG. 6 illustrates an example surgical hub comprising a plurality of modules coupled to the modular control tower.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 210 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
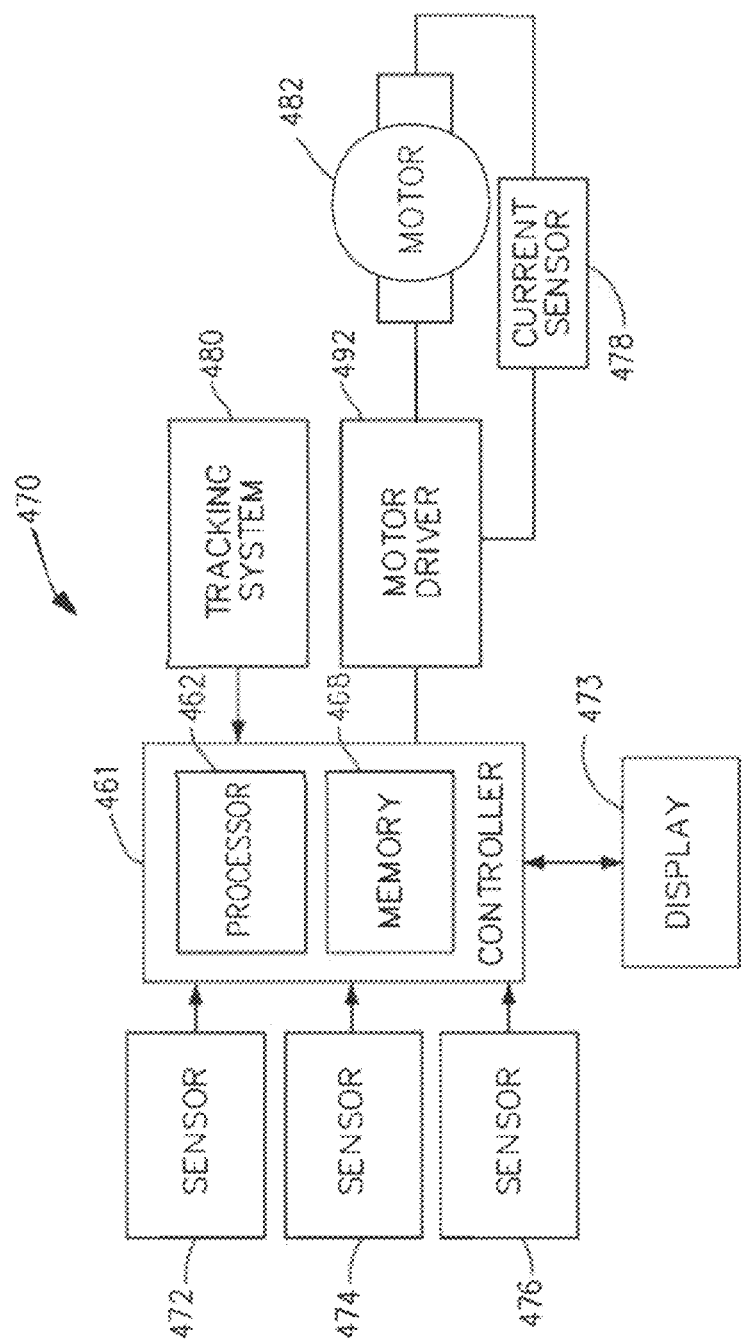
FIG. 7 shows an example surgical instrument or tool.

FIG. 7 illustrates a logic diagram of a control system 470 of a surgical instrument or tool in accordance with one or more aspects of the present disclosure. The system 470 may comprise a control circuit. The control circuit may include a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 may be configured to determine the position of the longitudinally movable displacement member. The position information may be provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 may display a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 may include a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In some examples, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 may be a full-bridge controller for use with external N-channel power metal-oxide semiconductor field-effect transistors (MOSFETs) specifically designed for inductive loads, such as brush DC motors. The driver 492 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the lowside FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 may comprise a controlled motor drive circuit arrangement comprising a position sensor 472 according to one aspect of this disclosure. The position sensor 472 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source may supplied power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 472 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches may be fed back to the microcontroller 461 that applies logic to determine a unique position signal corresponding to the longitudinal linear displacement d1+ d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system may comprise a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 may be a low-voltage and low-power component and includes four Hall-effect elements in an area of the position sensor 472 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bitshift, and table lookup operations. The angle position, alarm bits, and magnetic field information may be transmitted over a standard serial communication interface, such as a serial peripheral interface (SPI) interface, to the microcontroller 461. The position sensor 472 may provide 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertial, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force may be converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 474, such as, for example, a micro-strain gauge, that can be configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain can be converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub 203 as shown in FIGS. 5 and 6.

Figure 8:
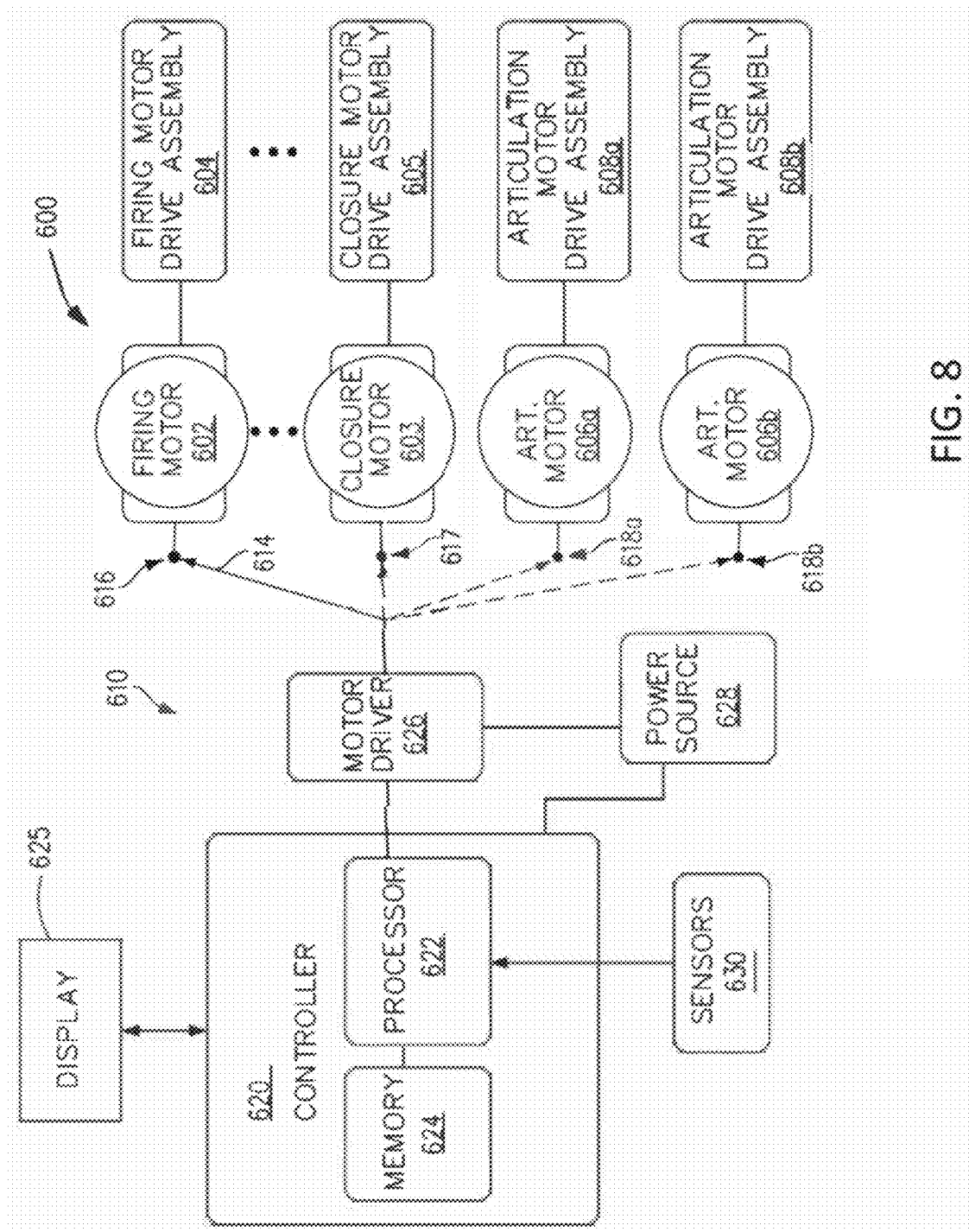
FIG. 8 illustrates an example surgical instrument or tool having motors that can be activated to perform various functions.

FIG. 8 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described herein, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 8, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 8, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described herein.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor can be a multipurpose, programmable device that accepts digital data as input, processes it according to instructions stored in its memory, and provides results as output. It can be an example of sequential digital logic, as it may have internal memory. Processors may operate on numbers and symbols represented in the binary numeral system.

The processor 622 may be any single-core or multicore processor such as those known under the trade name ARM Cortex by Texas Instruments. In certain instances, the microcontroller 620 may be an LM4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

The memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

One or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 9:
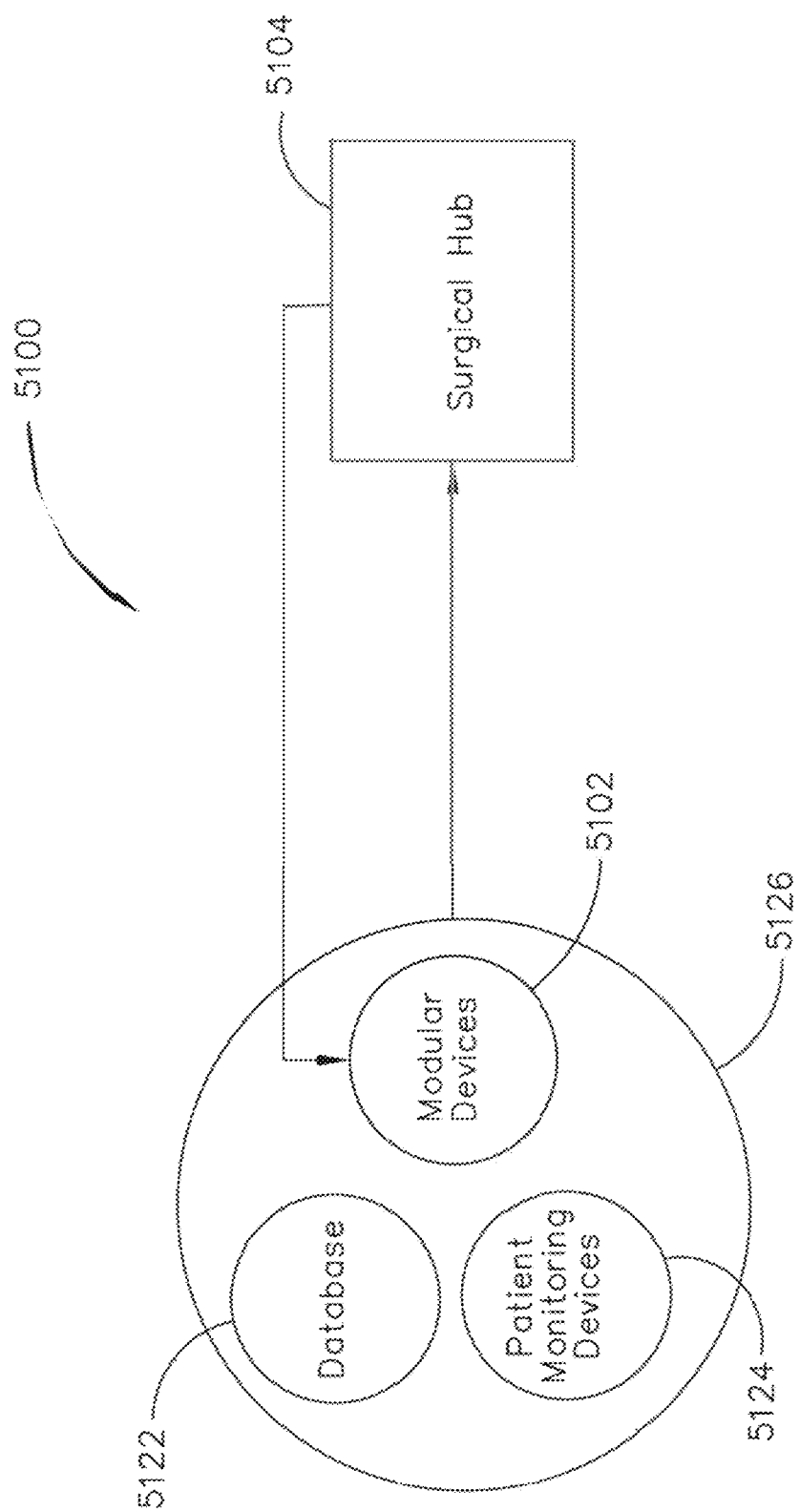
FIG. 9 is a diagram of an example situationally aware surgical system.

FIG. 9 illustrates a diagram of a situationally aware surgical system 5100, in accordance with at least one aspect of the present disclosure. In some exemplifications, the data sources 5126 may include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In an exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In an exemplification, the situational awareness system can include a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in an exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can be configured to compare the list of items for the procedure and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In some exemplifications, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In some exemplifications, the surgical hub 5104 can be configured to provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 10:
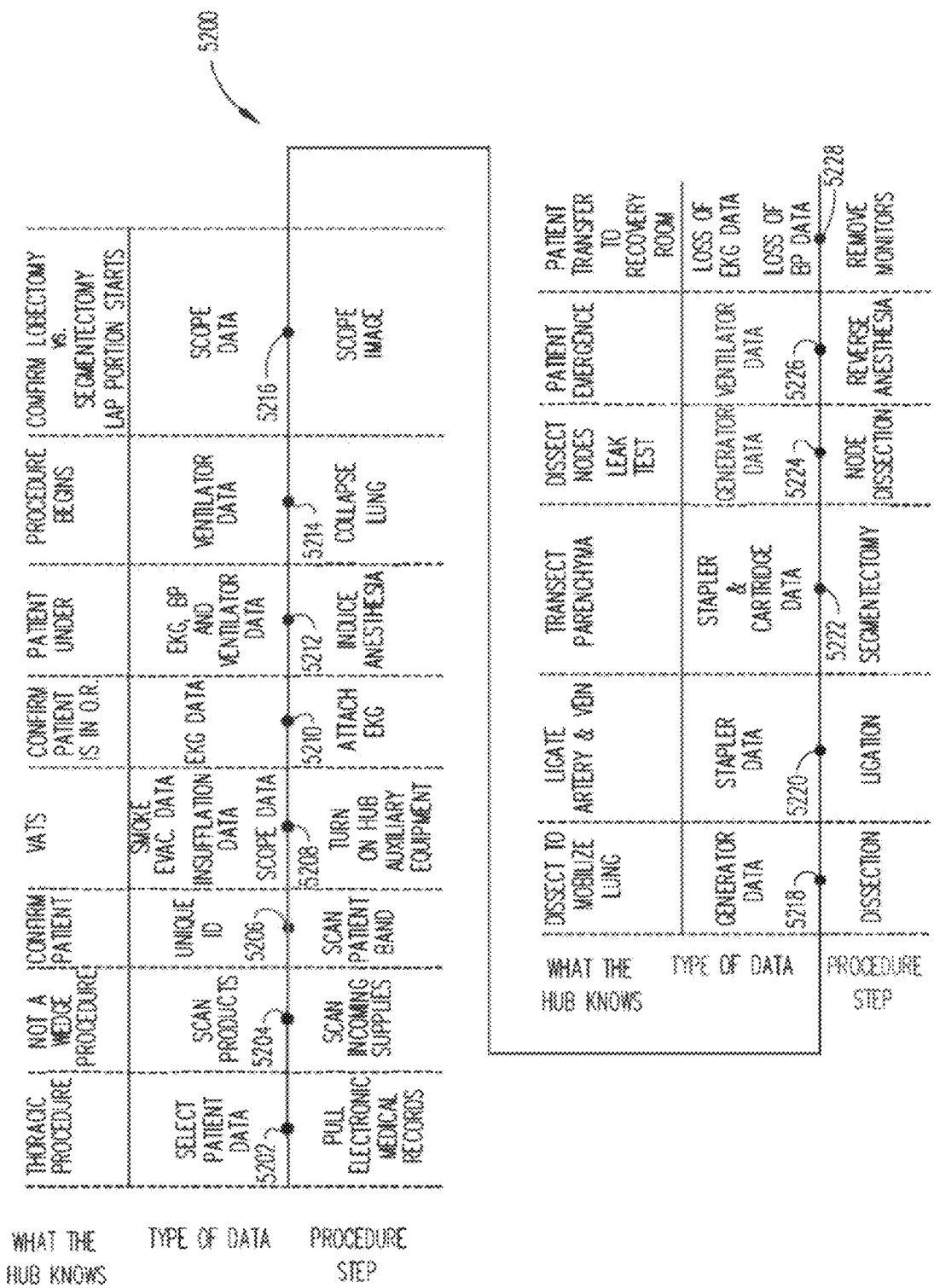
FIG. 10 illustrates an example timeline of an illustrative surgical procedure and the inferences that the surgical hub can make from the data detected at each step in the surgical procedure.

FIG. 10 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 9, reference should also be made to FIG. 9. The timeline 5200 may depict the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 may receive data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 can be able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described herein.

As the first step S202 in this illustrative procedure, the hospital staff members may retrieve the patient's EMR from the hospital's EMR database. Based on select patient data in the EMR, the surgical hub 5104 determines that the procedure to be performed is a thoracic procedure. Second 5204, the staff members may scan the incoming medical supplies for the procedure. The surgical hub 5104 cross-references the scanned supplies with a list of supplies that can be utilized in various types of procedures and confirms that the mix of supplies corresponds to a thoracic procedure. Further, the surgical hub 5104 may also be able to determine that the procedure is not a wedge procedure (because the incoming supplies either lack certain supplies that are necessary for a thoracic wedge procedure or do not otherwise correspond to a thoracic wedge procedure). Third 5206, the medical personnel may scan the patient band via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that may be located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 may determine that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 may pair with the surgical hub 5104. As the surgical hub 5104 begins receiving data from the patient monitoring devices 5124, the surgical hub 5104 may confirm that the patient is in the operating theater, as described in the process 5207, for example. Sixth 5212, the medical personnel may induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof. For example. Upon completion of the sixth step S212, the pre-operative portion of the lung segmentectomy procedure is completed and the operative portion begins.

Seventh 5214, the patient's lung that is being operated on may be collapsed (while ventilation is switched to the contralateral lung). The surgical hub 5104 can infer from the ventilator data that the patient's lung has been collapsed, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung can be the first operative step in this particular procedure. Eighth 5216, the medical imaging device 5108 (e.g., a scope) may be inserted and video from the medical imaging device may be initiated. The surgical hub 5104 may receive the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step S204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy may place the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. An example technique for performing a VATS lobectomy may utilize a single medical imaging device. An example technique for performing a VATS segmentectomy utilizes multiple cameras. An example technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team may begin the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team may proceed to the ligation step of the procedure. The surgical hub 5104 can infer that the surgeon is ligating arteries and veins because it may receive data from the surgical stapling and cutting instrument indicating that the instrument is being fired. Similar to the prior step, the surgical hub 5104 can derive this inference by cross-referencing the receipt of data from the surgical stapling and cutting instrument with the retrieved steps in the process. Eleventh 5222, the segmentectomy portion of the procedure can be performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (e.g., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step S224, the incisions and closed up and the post-operative portion of the procedure may begin.

Thirteenth 5226, the patient's anesthesia can be reversed. The surgical hub 5104 can infer that the patient is emerging from the anesthesia based on the ventilator data (i.e., the patient's breathing rate begins increasing), for example. Lastly, the fourteenth step S228 may be that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step S202 of the timeline 5200 depicted in FIG. 10, the patient data can also be utilized by a situationally aware surgical hub 5104 to generate control adjustments for the paired modular devices 5102.

Figure 11:
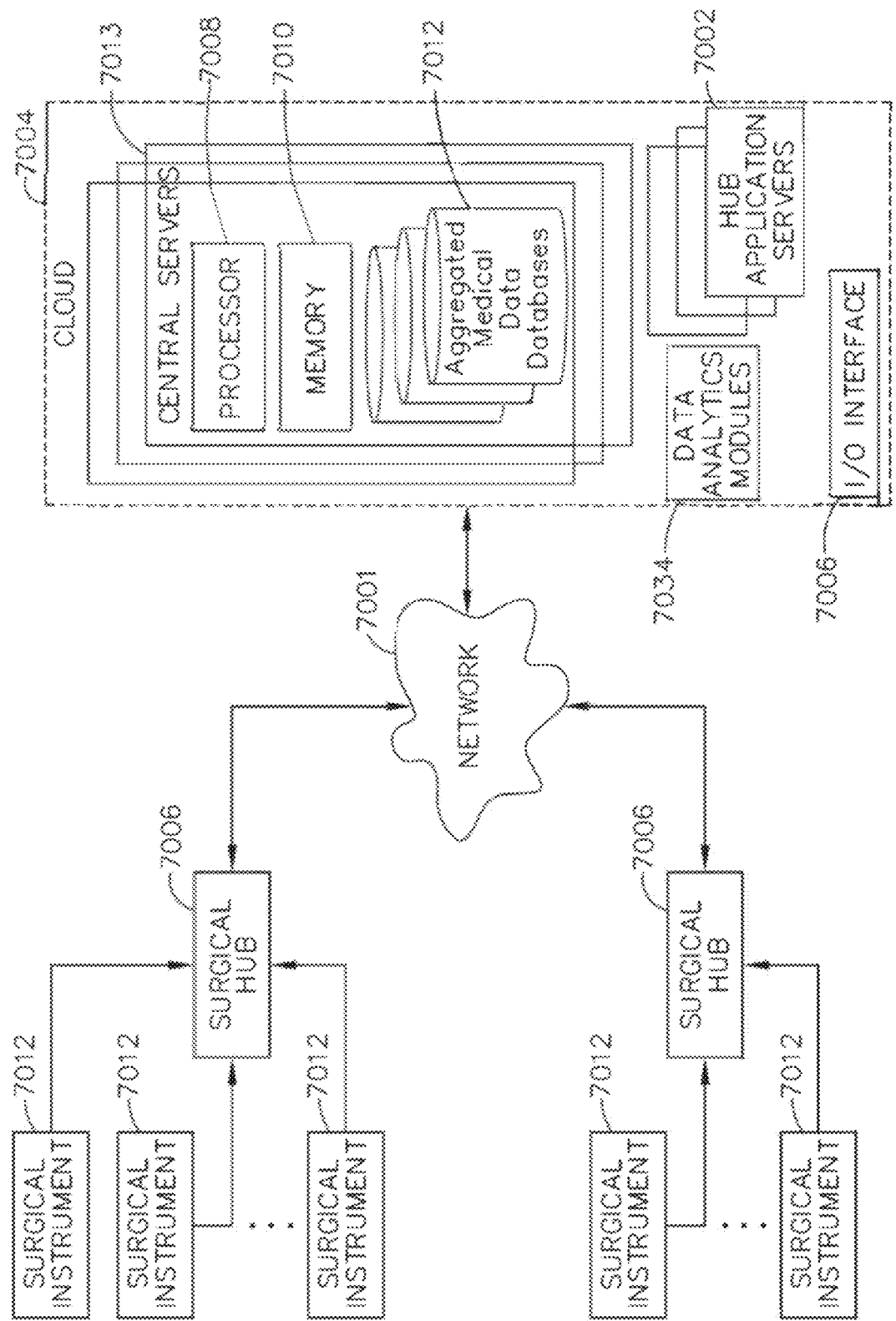
FIG. 11 is a block diagram of the computer-implemented interactive surgical system.

FIG. 11 is a block diagram of the computer-implemented interactive surgical system, in accordance with at least one aspect of the present disclosure. In one aspect, the computer-implemented interactive surgical system may be configured to monitor and analyze data related to the operation of various surgical systems that include surgical hubs, surgical instruments, robotic devices and operating theaters or healthcare facilities. The computer-implemented interactive surgical system may comprise a cloud-based analytics system. Although the cloud-based analytics system may be described as a surgical system, it may not be necessarily limited as such and could be a cloud-based medical system generally. As illustrated in FIG. 11, the cloud-based analytics system may comprise a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 may be communicatively coupled to one or more surgical instruments 7012. The hubs 7006 may also be communicatively coupled to the cloud 7004 of the computer-implemented interactive surgical system via the network 7001. The cloud 7004 may be a remote centralized source of hardware and software for storing, manipulating, and communicating data generated based on the operation of various surgical systems. As shown in FIG. 11, access to the cloud 7004 may be achieved via the network 7001, which may be the Internet or some other suitable computer network. Surgical hubs 7006 that may be coupled to the cloud 7004 can be considered the client side of the cloud computing system (i.e., cloud-based analytics system). Surgical instruments 7012 may be paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 11, the cloud 7004 comprises central servers 7013 (may be same or similar to remote server 7013), hub application servers 7002, data analytics modules 7034, and an input/output ("I/O") interface 7006. The central servers 7013 of the cloud 7004 collectively administer the cloud computing system, which includes monitoring requests by client surgical hubs 7006 and managing the processing capacity of the cloud 7004 for executing the requests. Each of the central servers 7013 may comprise one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also may comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7012 of the cloud 7004. In particular, the cloud 7004 may advantageously perform data analysis and operations on the aggregated data to yield insights and/or perform functions that individual hubs 7006 could not achieve on their own. To this end, as shown in FIG. 11, the cloud 7004 and the surgical hubs 7006 are communicatively coupled to transmit and receive information. The I/O interface 7006 is connected to the plurality of surgical hubs 7006 via the network 7001. In this way, the I/O interface 7006 can be configured to transfer information between the surgical hubs 7006 and the aggregated medical data databases 7011. Accordingly, the I/O interface 7006 may facilitate read/write operations of the cloud-based analytics system. Such read/write operations may be executed in response to requests from hubs 7006. These requests could be transmitted to the hubs 7006 through the hub applications. The I/O interface 7006 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 may be configured to host and supply shared capabilities to software applications (e.g., hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 12.

The particular cloud computing system configuration described in the present disclosure may be specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch-controlled user interfaces such that clinicians may control aspects of interaction between the surgical instruments 7012 and the cloud 7004. Other suitable user interfaces for control such as auditory controlled user interfaces can also be used.

Figure 12:
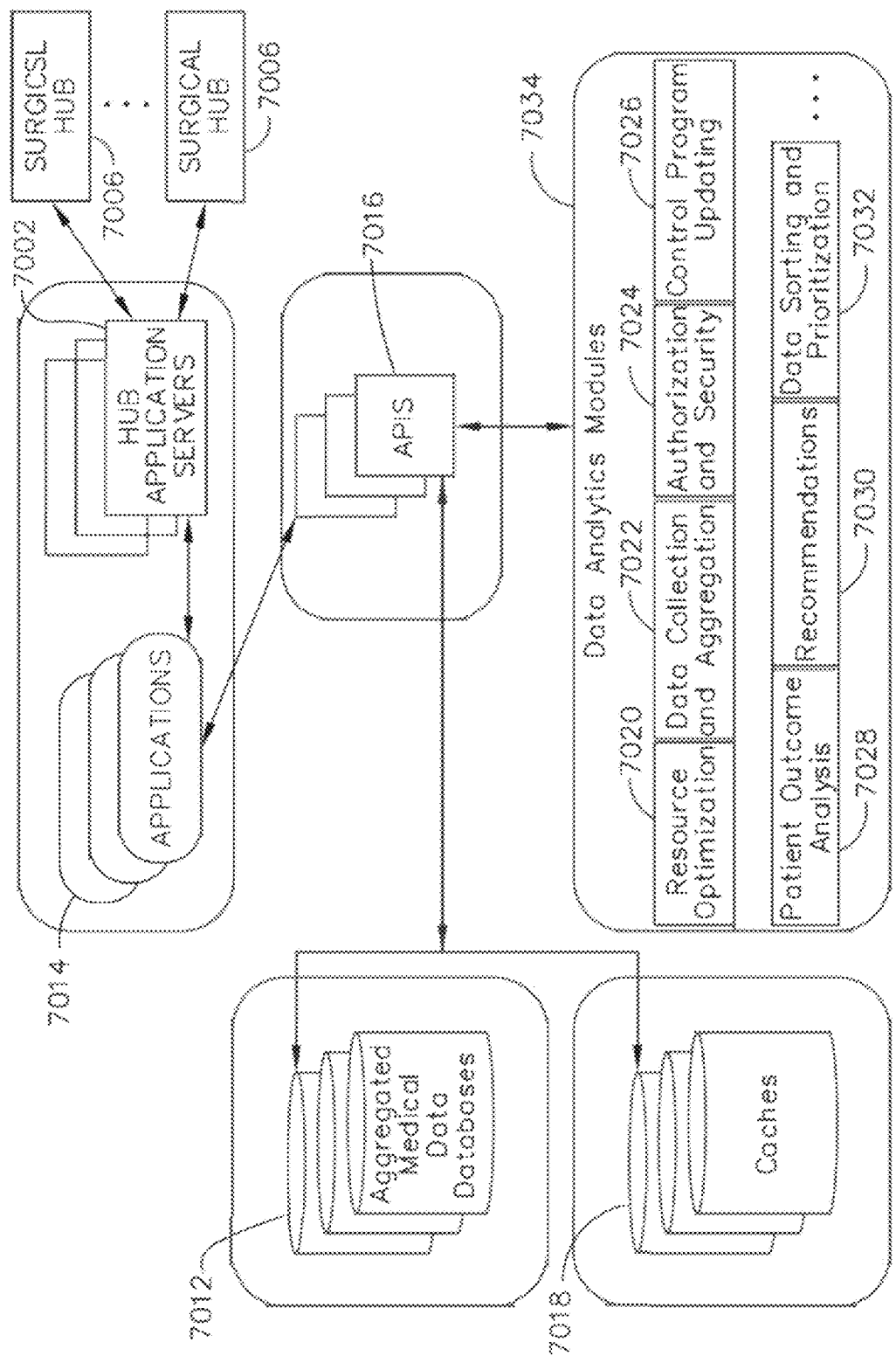
FIG. 12 illustrates the functional architecture of an example computer-implemented interactive surgical system.

FIG. 12 is a block diagram which illustrates the functional architecture of the computer-implemented interactive surgical system, in accordance with at least one aspect of the present disclosure. The cloud-based analytics system may include a plurality of data analytics modules 7034 that may be executed by the processors 7008 of the cloud 7004 for providing data analytic solutions to problems specifically arising in the medical field. As shown in FIG. 12, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 may define the set of protocols and routines corresponding to the hub applications 7014. Additionally, the APIs 7016 may manage the storing and retrieval of data into and from the aggregated medical databases 7012 for the operations of the applications 7014. The caches 7018 may also store data (e.g., temporarily) and may be coupled to the APIs 7016 for more efficient retrieval of data used by the applications 7014. The data analytics modules 7034 in FIG. 12 may include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules may be used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently. The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that may be transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004. Furthermore, for security purposes, the cloud could maintain a database of hubs 7006, instruments 7012, and other devices that may comprise a "black list" of prohibited devices. In particular, a surgical hubs 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally, or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash-based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described herein to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g., a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional example details for the various functions described are provided in the ensuing descriptions below. Each of the various descriptions may utilize the cloud architecture as described in FIGS. 11 and 12 as one example of hardware and software implementation.

Figure 13:
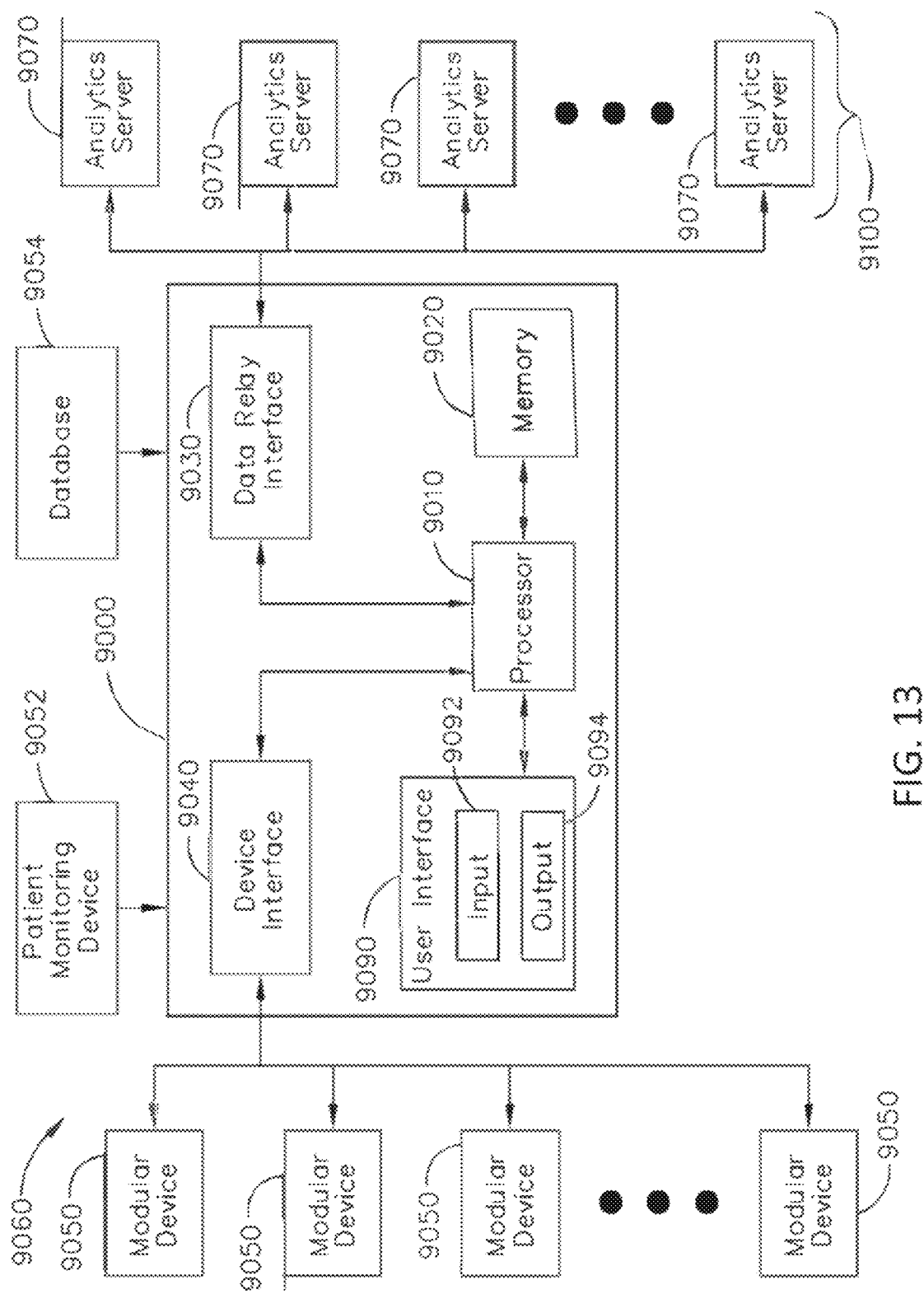
FIG. 13 illustrates an example computer-implemented interactive surgical system that is configured to adaptively generate control program updates for modular devices.

FIG. 13 illustrates a block diagram of a computer-implemented adaptive surgical system 9060 that is configured to adaptively generate control program updates for modular devices 9050, in accordance with at least one aspect of the present disclosure. In some exemplifications, the surgical system may include a surgical hub 9000, multiple modular devices 9050 communicably coupled to the surgical hub 9000, and an analytics system 9100 communicably coupled to the surgical hub 9000. Although a single surgical hub 9000 may be depicted, it should be noted that the surgical system 9060 can include any number of surgical hubs 9000, which can be connected to form a network of surgical hubs 9000 that are communicably coupled to the analytics system 9010. In some exemplifications, the surgical hub 9000 may include a processor 9010 coupled to a memory 9020 for executing instructions stored thereon and a data relay interface 9030 through which data is transmitted to the analytics system 9100. In some exemplifications, the surgical hub 9000 further may include a user interface 9090 having an input device 9092 (e.g., a capacitive touchscreen or a keyboard) for receiving inputs from a user and an output device 9094 (e.g., a display screen) for providing outputs to a user. Outputs can include data from a query input by the user, suggestions for products or mixes of products to use in a given procedure, and/or instructions for actions to be carried out before, during, or after surgical procedures. The surgical hub 9000 further may include an interface 9040 for communicably coupling the modular devices 9050 to the surgical hub 9000. In one aspect, the interface 9040 may include a transceiver that is communicably connectable to the modular device 9050 via a wireless communication protocol. The modular devices 9050 can include, for example, surgical stapling and cutting instruments, electrosurgical instruments, ultrasonic instruments, insufflators, respirators, and display screens. In some exemplifications, the surgical hub 9000 can further be communicably coupled to one or more patient monitoring devices 9052, such as EKG monitors or BP monitors. In some exemplifications, the surgical hub 9000 can further be communicably coupled to one or more databases 9054 or external computer systems, such as an EMR database of the medical facility at which the surgical hub 9000 is located.

When the modular devices 9050 are connected to the surgical hub 9000, the surgical hub 9000 can sense or receive perioperative data from the modular devices 9050 and then associate the received perioperative data with surgical procedural outcome data. The perioperative data may indicate how the modular devices 9050 were controlled during the course of a surgical procedure. The procedural outcome data includes data associated with a result from the surgical procedure (or a step thereof), which can include whether the surgical procedure (or a step thereof) had a positive or negative outcome. For example, the outcome data could include whether a patient suffered from postoperative complications from a particular procedure or whether there was leakage (e.g., bleeding or air leakage) at a particular staple or incision line. The surgical hub 9000 can obtain the surgical procedural outcome data by receiving the data from an external source (e.g., from an EMR database 9054), by directly detecting the outcome (e.g., via one of the connected modular devices 9050), or inferring the occurrence of the outcomes through a situational awareness system. For example, data regarding postoperative complications could be retrieved from an EMR database 9054 and data regarding staple or incision line leakages could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. In some exemplifications, the analytics system 9100 may include a network of analytics servers 9070 that are configured to receive data from the surgical hubs 9000. Each of the analytics servers 9070 can include a memory and a processor coupled to the memory that is executing instructions stored thereon to analyze the received data. In some exemplifications, the analytics servers 9070 may be connected in a distributed computing architecture and/or utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to the modular devices' 9050 control programs.

Additional detail regarding the computer-implemented interactive surgical system 9060, including the surgical hub 9000 and various modular devices 9050 connectable thereto, are described in connection with FIGS. 5-6.

Figure 14:
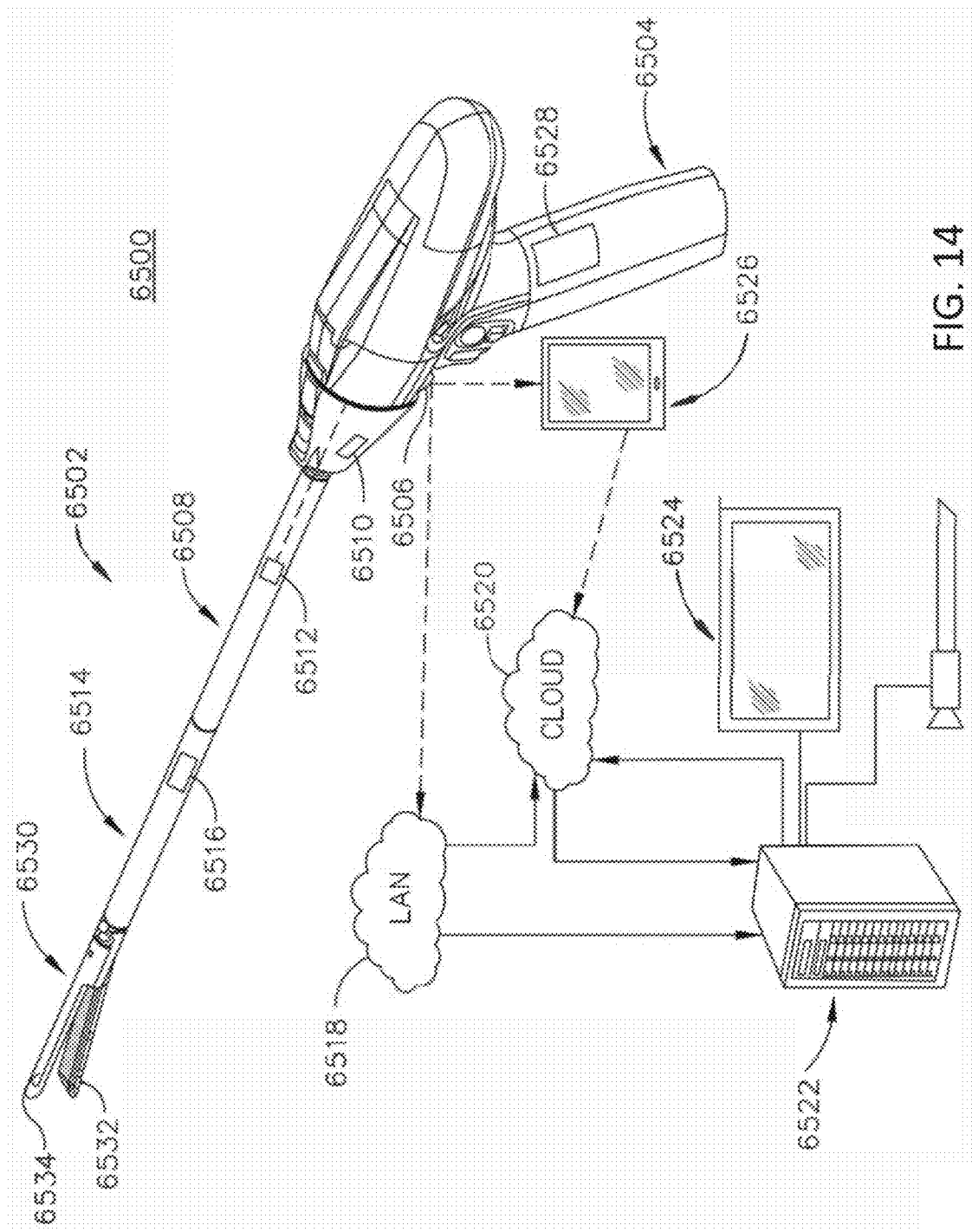
FIG. 14 illustrates an example surgical system that includes a handle having a controller and a motor, an adapter releasably coupled to the handle, and a loading unit releasably coupled to the adapter.

FIG. 14 provides a surgical system 6500 in accordance with the present disclosure and may include a surgical instrument 6502 that can be in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 may include a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 may include an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 may be configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more than one time prior to being replaced. The second jaw 6534 may include an anvil that deforms or otherwise secures the fasteners about tissue as the fasteners are ejected from the multi-fire fastener cartridge.

The handle 6504 may include a motor that is coupled to the drive shaft to affect rotation of the drive shaft. The handle 6504 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 may be in communication with a controller 6528 of the handle 6504 to selectively activate the motor to affect rotation of the drive shafts. The controller 6528 may be disposed within the handle 6504 and is configured to receive input from the control interface and adapter data from the adapter 6508 or loading unit data from the loading unit 6514. The controller 6528 may analyze the input from the control interface and the data received from the adapter 6508 and/or loading unit 6514 to selectively activate the motor. The handle 6504 may also include a display that is viewable by a clinician during use of the handle 6504. The display may be configured to display portions of the adapter or loading unit data before, during, or after firing of the instrument 6502.

The adapter 6508 may include an adapter identification device 6510 disposed therein and the loading unit 6514 includes a loading unit identification device 6516 disposed therein. The adapter identification device 6510 may be in communication with the controller 6528, and the loading unit identification device 6516 may be in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 may provide an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 can be configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 may include a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508) attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6528. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

Figure 15:
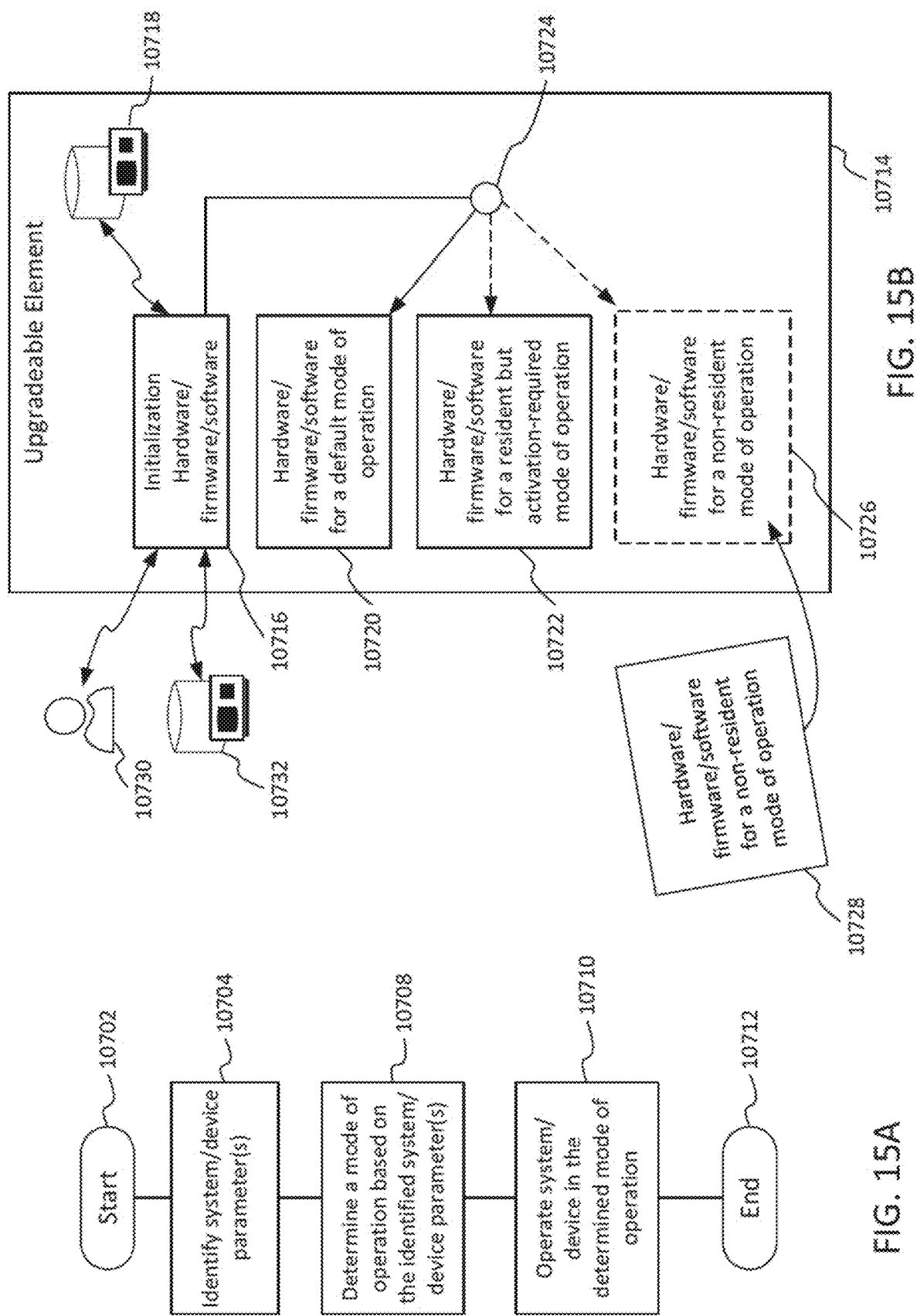
FIG. 15A illustrates an example flow for determining a mode of operation and operating in the determined mode.
FIG. 15B illustrates an example flow for changing a mode of operation.

FIG. 15A illustrates an example flow for determining a mode of operation and operating in the determined mode. The computer-implemented interactive surgical system and/or components and/or subsystems of the computer-implemented interactive surgical system may be configured to be updated. Such updates may include the inclusions of features and benefits that were not available to the user before the update. These updates may be established by any method of hardware, firmware, and software updates suitable for introducing the feature to the user. For example, replaceable/swappable (e.g., hot swappable) hardware components, flashable firmware devices, and updatable software systems may be used to update computer-implemented interactive surgical system and/or components and/or subsystems of the computer-implemented interactive surgical system.

The updates may be conditioned on any suitable criterion or set of criteria. For example, an update may be conditioned on one or more hardware capabilities of the system, such as processing capability, bandwidth, resolution, and the like. For example, the update may be conditioned on one or more software aspects, such as a purchase of certain software code. For example, the update may be conditioned on a purchased service tier. The service tier may represent a feature and/or a set of features the user is entitled to use in connection with the computer-implemented interactive surgical system. The service tier may be determined by a license code, an e-commerce server authentication interaction, a hardware key, a username/password combination, a biometric authentication interaction, a public/private key exchange interaction, or the like.

At 10704, a system/device parameter may be identified. The system/device parameter may be any element or set of elements on which an update in conditioned. For example, the computer-implemented interactive surgical system may detect a certain bandwidth of communication between a modular device and a surgical hub. For example, the computer-implemented interactive surgical system may detect an indication of the purchase of certain service tier.

At 10708, a mode of operation may be determined based on the identified system/device parameter. This determination may be made by a process that maps system/device parameters to modes of operation. The process may be a manual and/or an automated process. The process may be the result of local computation and/or remote computation. For example, a client/server interaction may be used to determine the mode of operation based on the on the identified system/device parameter. For example, local software and/or locally embedded firmware may be used to determine the mode of operation based on the identified system/device parameter. For example, a hardware key, such as a secure microprocessor for example, may be used to determine the mode of operation based on the identified system/device parameter.

At 10710, operation may proceed in accordance with the determined mode of operation. For example, a system or device may proceed to operate in a default mode of operation. For example, a system or device may proceed to operate in an alternate mode of operation. The mode of operation may be directed by control hardware, firmware, and/or software already resident in the system or device. The mode of operation may be directed by control hardware, firmware, and/or software newly installed/updated.

FIG. 15B illustrates an example functional block diagram for changing a mode of operation. An upgradeable element 10714 may include an initialization component 10716. The initialization component 10716 may include any hardware, firmware, and/or software suitable determining a mode of operation. For example, the initialization component 10716 may be portion of a system or device start-up procedure. The initialization component 10716 may engage in an interaction to determine a mode of operation for the upgradeable element 10714. For example, the initialization component 10716 may interact with a user 10730, an external resource 10732, and/or a local resource 10718 for example. For example, the initialization component 10716 may receive a licensing key from the user 10730 to determine a mode of operation. The initialization component 10716 may query an external resource 10732, such as a server for example, with a serial number of the upgradable device 10714 to determine a mode of operation. For example, the initialization component 10716 may query a local resource 10718, such as a local query to determine an amount of available bandwidth and/or a local query of a hardware key for example, to determine a mode of operation.

The upgradeable element 10714 may include one or more operation components 10720, 10722, 10726, 10728 and an operational pointer 10724. The initialization component 10716 may direct the operational pointer 10724 to direct the operation of the upgradable element 10741 to the operation component 10720, 10722, 10726, 10728 that corresponds with the determined mode of operation. The initialization component 10716 may direct the operational pointer 10724 to direct the operation of the upgradable element to a default operation component 10720. For example, the default operation component 10720 may be selected on the condition of no other alternate mode of operation being determined. For example, the default operation component 10720 may be selected on the condition of a failure of the initialization component and/or interaction failure. The initialization component 10716 may direct the operational pointer 10724 to direct the operation of the upgradable element 10714 to a resident operation component 10722. For example, certain features may be resident in the upgradable component 10714 but require activation to be put into operation. The initialization component 10716 may direct the operational pointer 10724 to direct the operation of the upgradable element 10714 to install a new operation component 10728 and/or a new installed operation component 10726. For example, new software and/or firmware may be downloaded. The new software and or firmware may contain code to enable the features represented by the selected mode of operation. For example, a new hardware component may be installed to enable the selected mode of operation.

A surgical hub may have cooperative interactions with one of more means of displaying the image from a surgical scope such as a laparoscopic scope and information from one of more other smart devices. The hub may be configured to interact with multiple displays to enable combined display and control of the data distributed across the multiple displays.

The display of the information can be controlled in different visualization control modes. For example, the content at one or more displays can be controlled by a user, and/or be automated. The visualization control mode may be operated at different levels based on the control schemes present in the operating room.

Display of information from surgical devices and the hub can be operated on multiple levels of complexity and control. These multiple levels may be associated with multiple levels of hardware capacity, software capability, and/or firmware capability. For example, visualization control modes with more supported capabilities may require interlocking hardware and/or software to ensure synchronization or pairing of data in time. These levels could be controlled or limited via different visualization control modes. For example, the current visualization control mode may be determined based on the hub's capability to operate the surgical devices at an appropriate refresh rate, the processing requirements, the memory requirements, user input(s), and/or the purchased level of software subscription for operating the surgical system.

The hub may adjust the visualization control mode, e.g., upgrading or downgrading, based on an internal parameter of the surgical hub. The internal control parameter may be determined based on a change of the internal control parameter. The change may be trigger by processing capability, free processing capacity or memory, heat generated by the system, its power consumption, balance of the power consumption to other attached systems, user inputs, and/or a subscription level of the system.

Figure 37:
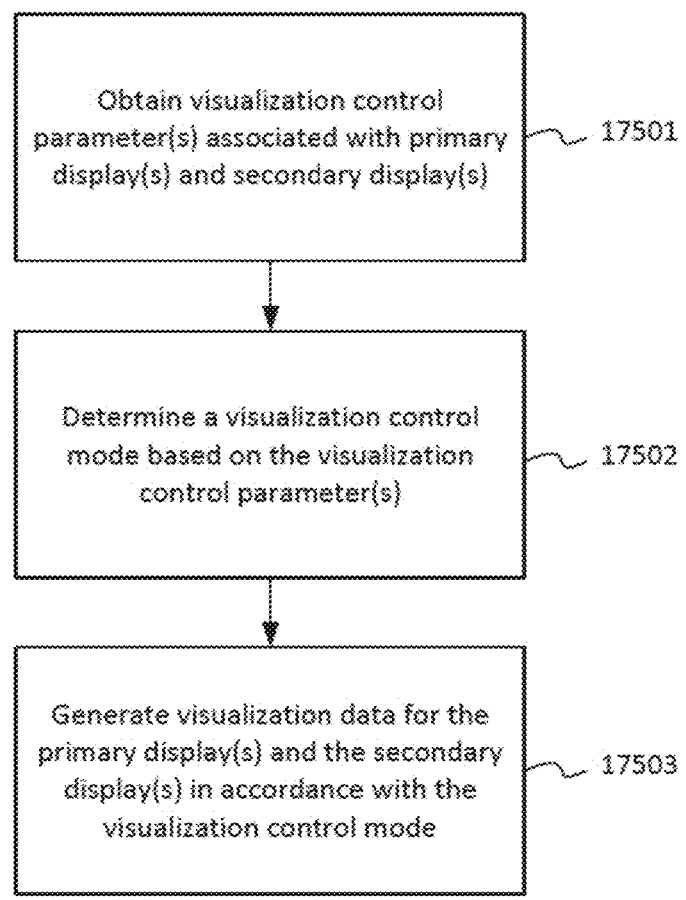
FIG. 37 shows an example flow for a hub operating under tiered visualization control modes.

FIG. 37 shows an example flow for a surgical hub operating under tiered visualization control modes. The hub may include a communication array that may be connected to a primary display, a secondary display, a laparoscopic scope and at least one surgical instrument. As shown, at 17501, the hub may obtain one or more visualization control parameter(s) associated with the primary and secondary displays.

As shown in FIG. 37, at 17502, the hub may determine a visualization control mode based on the visualization control parameter(s). The visualization control parameter may comprise at least one of: available memory, available data bandwidth, heat generated by the surgical hub, heat generated by the secondary display, power capacity associated with the surgical hub, power capacity associated with an operating room, power capacity associated with a medical facility, a power usage, a balance of the power consumption to at least one attached system, processor utilization, and/or memory utilization.

At 17503, the hub may generate visualization data for the primary displays and the secondary displays in accordance with the visualization control mode.

For example, the visualization control parameter(s) may include an indication from a tiered system. The tiered system may scale the display capabilities and interactive display control capabilities and/or the like, based on the available data bandwidth, power capacity and usage, processor and memory utilization, and/or internal or attached systems. The tiered system may determine max display and interactive display control capabilities the surgical hub may operate under. For example, upon detecting the power capability associated with the operation room, associated with the surgical hub, and/or associated with a medical facility is below a threshold, the tiered system may scale down the surgical hub's visualization control capabilities. For example, upon detecting available data bandwidth is below a threshold, memory utilization is above a certain threshold, power usage is above a certain threshold, and/or other system conditions that may warrant scaling down visualization control capabilities, the tiered system may limit or disable the display related communication between the surgical hub and the devices and/or the display related communication between the surgical hub and external server(s). Multiple-display capabilities may be disabled. Augmented reality capabilities may be disabled. The tiered system may be a module within the surgical hub or may be a system external to the surgical hub.

In an example visualization control mode, multiple displays may be used to display differing aspects of the information or different types of information with relevance to the primary viewer of the display. Some or all of the displays can be controlled by another system that the hub may be in communication with.

In an example visualization control mode, one or a portion of one display may be controlled via another display. The content shown at one or a portion of a display may be associated with another display. For example, in picture in picture display, the content source of the mini picture can be controlled in an example visualization control mode. This feature is further described in U.S. patent application Ser. No. 15/940,742, titled DUAL COMS ARRAY IMAGING, filed Mar. 29, 2018, which is incorporated by reference herein in its entirety.

In an example visualization control mode, individual users may have different display systems that work in concert with a main shared display. Different overlay information may be generated for different user roles, such that users may be provided with personally directed information or personalized overlaid data. For example, a user may be provided with personalize data for interaction as described in U.S. patent application Ser. No. 15/940,671, titled DUAL SURGICAL HUB SPATIAL AWARENESS TO DETERMINE DEVICES IN OPERATION THEATER, filed Mar. 29, 2018, which is incorporated by reference herein in its entirety.

In an example visualization control mode, the hub may restrict visualization display to be on a primary display. For example, when operating under a first visualization control mode, the hub may control the primary display. The hub may determine which pieces of information and video displays should be sharing portions of the overall display real estate.

Figure 16:
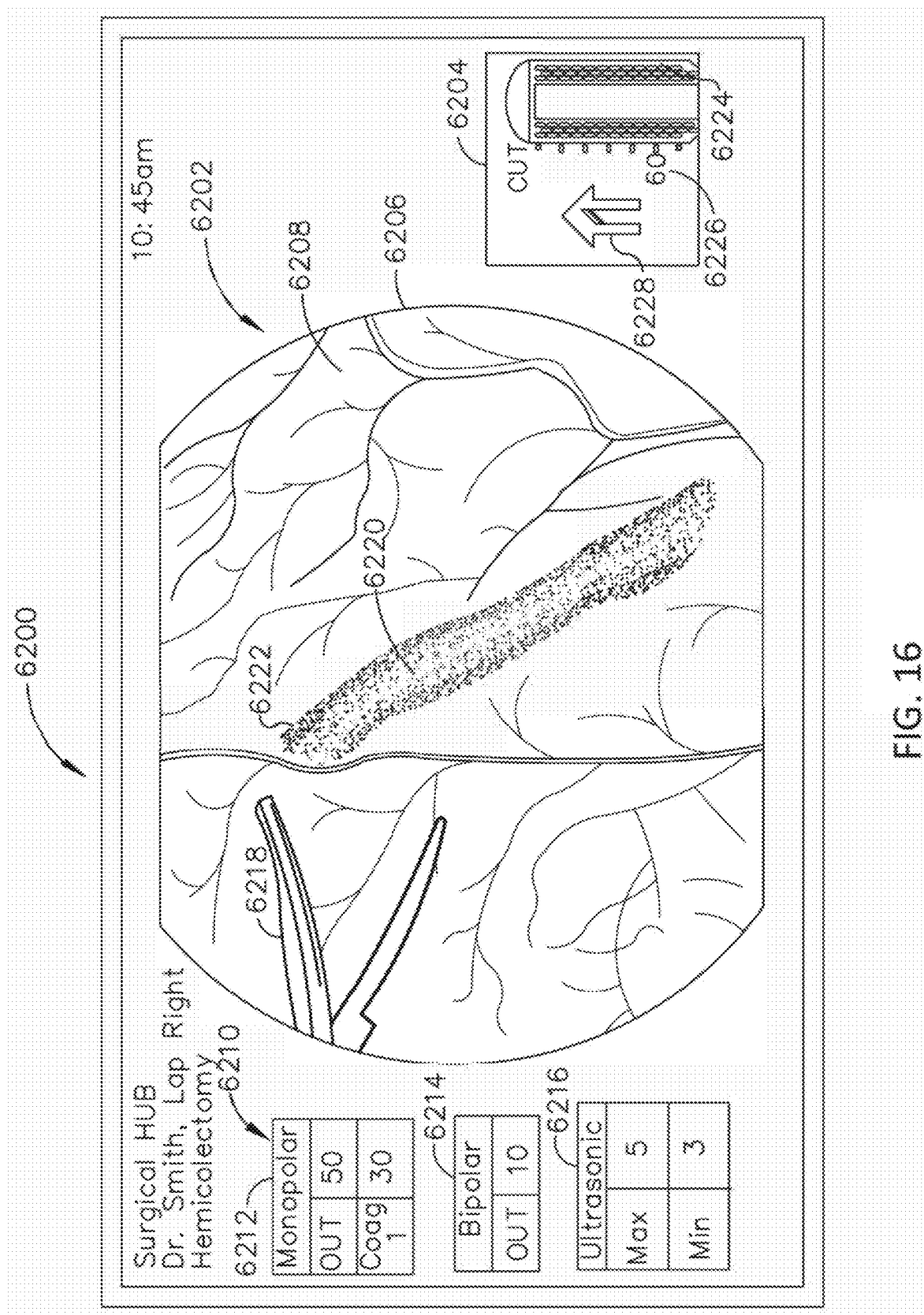
FIG. 16 illustrates a primary display of the surgical hub comprising a global and local display.

FIG. 16 illustrates an example primary display 6200 associate with the surgical hub 206 comprising a global display window 6202 and a local instrument display window 6204, according to one aspect of the present disclosure. With continued reference to FIGS. 1-11 to show interaction with an interactive surgical system 100 environment including a surgical hub 106, 206 and FIGS. 12-14 for surgical hub connected instruments together, the local instrument display 6204 behavior may be displayed when the instrument 235 senses the connectable presence of a global display window 6202 through the surgical hub 206. The global display window 6202 may show a field of view 6206 of a surgical site 6208, as viewed through a medical imaging device such as, for example, a laparoscope/endoscope 219 coupled to an imaging module 238, at the center of the surgical hub display 215, referred to herein also as a monitor, for example. The end effector 6218 portion of the connected instrument 235 may be shown in the field of view 6206 of the surgical site 6208 in the global display window 6202. The images shown on the display 237 located on an instrument 235 coupled to the surgical hub 206 is shown, or mirrored, on the local instrument display window 6204 located in the lower right corner of the monitor 6200 as shown in FIG. 16, for example.

During operation, relevant instrument and information and menus may be displayed on the display 237 located on the instrument 235 until the instrument 235 senses a connection of the instrument 235 to the surgical hub 206 at which point all or some sub-set of the information presented on the instrument display 237 may be displayed (e.g., only) on the local instrument display window 6204 portion of the surgical hub display 6200 through the surgical hub 206. The information displayed on the local instrument display window 6204 may be mirrored on the display 237 located on the instrument 235 or may be no longer accessible on the instrument display 237 detonated screen. This technique frees up the instrument 235 to show different information or to show larger font information on the surgical hub display 6200.

The primary display 6200 may provide perioperative visualization of the surgical site 6208. Advanced imaging may identify and visually highlight 6222 critical structures such as the ureter 6220 (or nerves, etc.) and may track instrument proximity displays 6210 and shown on the left side of the display 6200. In the illustrated example, the instrument proximity displays 6210 may show instrument specific settings. For example, the top instrument proximity display 6212 may show settings for a monopolar instrument, the middle instrument proximity display 6214 may show settings for a bipolar instrument, and the bottom instrument proximity display 6212 may show settings for an ultrasonic instrument.

Figure 17:
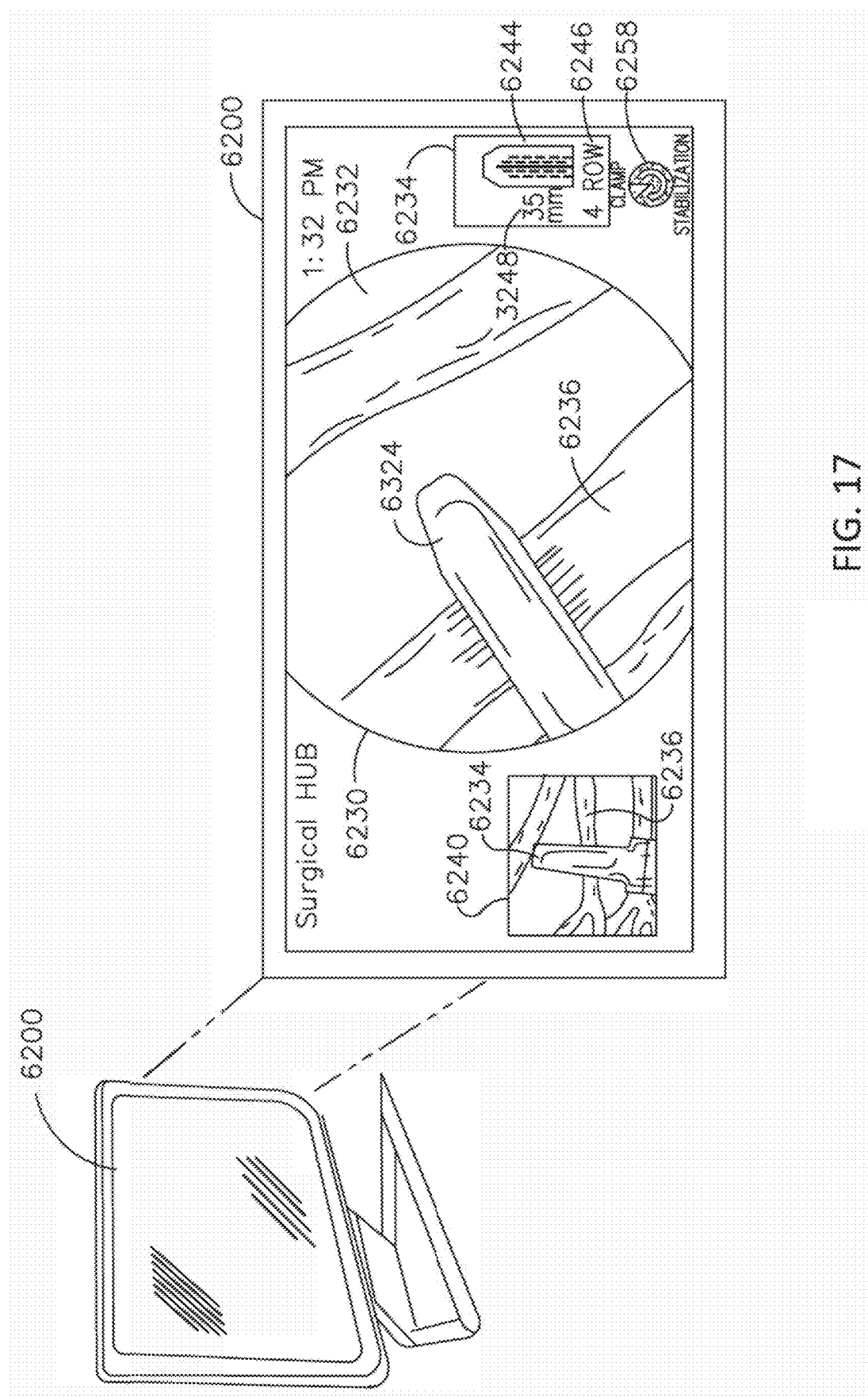
FIG. 17 illustrates an example a primary display of the surgical hub.

FIG. 17 illustrate an example primary display having a composite overhead views of an end-effector 6234 portion of a surgical stapler mapped using two or more imaging arrays or one array and time to provide multiple perspective views of the end-effector 6234 to enable the composite imaging of an overhead field of view. The techniques described herein may be applied to ultrasonic instruments, electrosurgical instruments, combination ultrasonic/electrosurgical instruments, and/or combination surgical stapler/electrosurgical instruments. Several techniques may be performed for overlaying or augmenting images and/or text from multiple image/text sources to present composite images on a display (e.g., a single display).

As shown in FIG. 17, a primary display 6200 of the surgical hub 206 may display a primary window 6230. The primary window 6230 may be located at the center of the screen shows a magnified or exploded narrow angle view of a surgical field of view 6232. The primary window 6230 located in the center of the screen shows a magnified or narrow angle view of an end-effector 6234 of the surgical stapler grasping a vessel 6236. The primary window 6230 may display knitted images to produce a composite image that enables visualization of structures adjacent to the surgical field of view 6232. A second window 6240 may be shown in the lower left corner of the primary display 6200. The second window 6240 displays a knitted image in a wide-angle view at standard focus of the image shown in the primary window 6230 in an overhead view. The overhead view provided in the second window 6240 can enable the viewer to easily see items that are out of the narrow field surgical field of view 6232 without moving the laparoscope, or other imaging device 239 coupled to the imaging module 238 of the surgical hub 206. A third window 6242 can be shown in the lower right corner of the primary display 6200 shows an icon 6244 representative of the staple cartridge of the end-effector 6234 (e.g., a staple cartridge in this instance) and additional information such as "4 Row" indicating the number of staple rows 6246 and "35 mm" indicating the distance 6248 traversed by the knife along the length of the staple cartridge. Below the third window 6242 is displayed an icon 6258 of a frame of the current state of a clamp stabilization sequence 6250 that indicates clamp stabilization.

In an example visualization control mode, display may be controlled by the user, for example, via motion tracking (e.g., head orientation relative to a monitor), hand gestures, voice activation and other means within the sterile field. User gestures may be determined based on a wearable device worn by a user such as smart watch and/or camera(s) in the OR. The user's head movement may be determined based on AR goggles and/or camera(s) in the OR.

Figure 19:
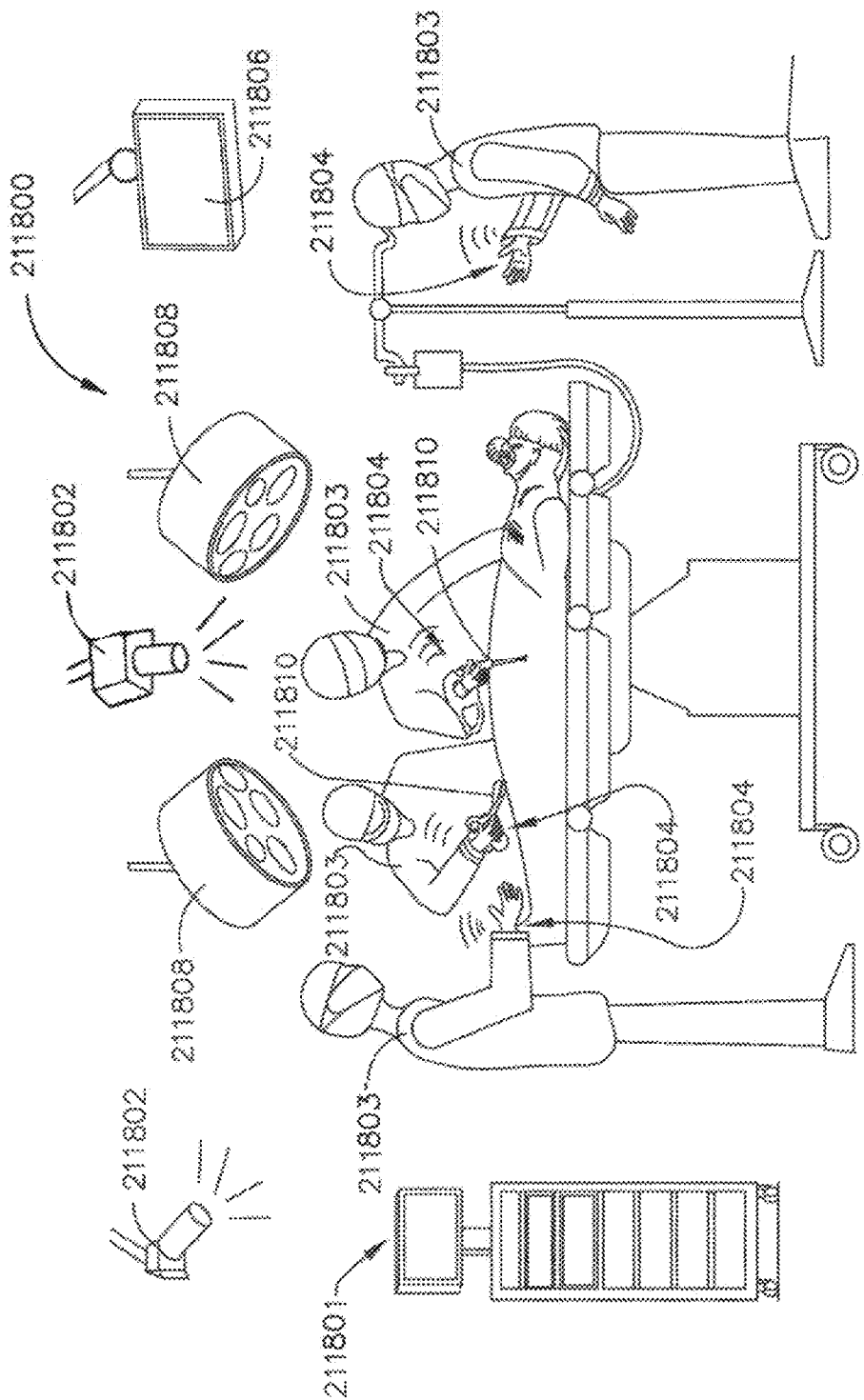
FIG. 19 is a diagram of an illustrative operating room (OR) setup.

FIG. 19 is a diagram of an illustrative OR setup that may enable display control via motion tracking, gesture tracking and/or voice activation. In various implementations, a surgical hub 211801 can be communicably connected to one or more cameras 211802, surgical instruments 211810, displays 211806, overhead lights 211808, and other surgical devices within the OR 211800 via a communications protocol (e.g., Bluetooth). The cameras 211802 can be oriented in order to capture images and/or video of the surgical staff members 211803 and/or surgical instruments 211810 (or other surgical devices) within the OR 211800 during the course of a surgical procedure. The captured image(s) can include static images or moving images (e.g., video). The images of the surgical staff members 211803 and/or surgical instruments 211810 can be captured at a variety of angles and magnifications, utilize different filters, and so on. For example, the cameras 211802 may be arranged within the OR 211800 so that they can collectively visualize each surgical staff member performing the procedure. Accordingly, the surgical hub 211801 can receive the captured image and/or video data from the cameras 211802 to visually analyze the surgical staff members 211803 and/or the surgical instruments 211810 during the surgical procedure. The image and/or video data can be processed utilizing a variety of machine vision, image processing, object recognition, and optical tracking techniques to track characteristics, properties, actions, and movements of the surgical staff members 211803 and/or the surgical instruments 211810.

Figure 20:
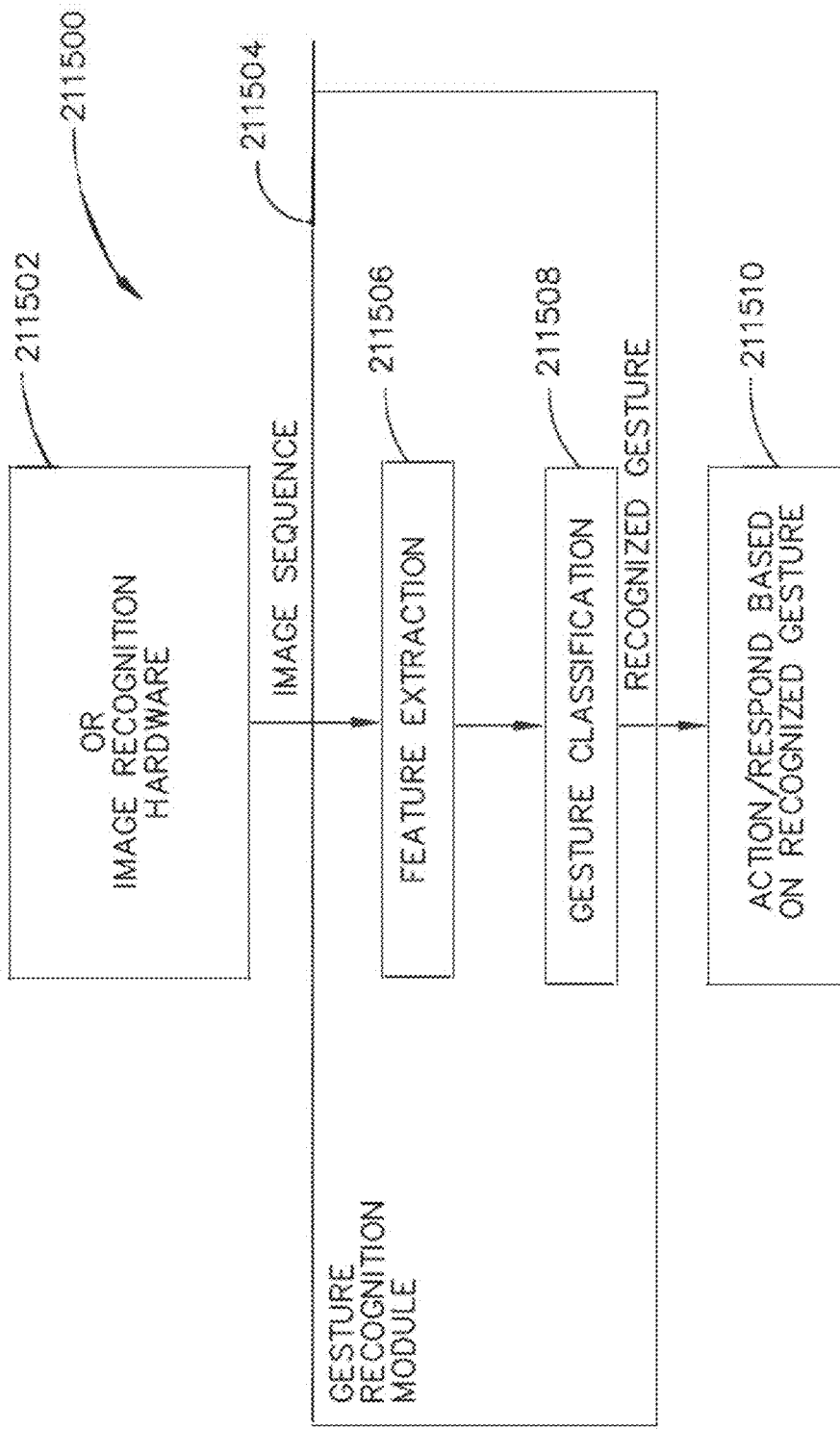
FIG. 20 is a block diagram of a gesture recognition system.

FIG. 20 is a block diagram of a gesture recognition system 211500 that may be used to control display(s) in an example visualization control mode. The gesture recognition system 211500 includes a gesture recognition module 211504 that can be executed by a processor or control circuit of a computer system, such as the processor 244 of the surgical hub 206 illustrated in FIG. 10. Accordingly, the gesture recognition module 211504 can be embodied as a set of computer-executable instructions stored in a memory 249 that, when executed by the processor 244, cause the computer system (e.g., a surgical hub 211801) to perform the described steps.

The gesture recognition system 211500 may receive image or video data from the image recognition hardware/ software (e.g., the cameras 211802), recognize various gestures 211804 that can be performed by the surgical staff members 211803 (e.g., determine 211604, 211624 whether a gesture is being performed in the processes 211600, 211620), and take a corresponding action or otherwise respond to the particular detected gesture 211804 (e.g., control 211606 a surgical device or save 211626 the data as metadata in the processes 211600, 211620). In an aspect, the gesture recognition module 211504 can include a feature extraction module 211506 and a gesture classification module 211508. The feature extract module 211506 may extract measurable, discriminative properties or characteristics (e.g., features) from the image/video data. The features can include edges (extracted via a Canny edge detector algorithm, for example), curvature, corners (extracted via a Harris & Stephens corner detector algorithm, for example), and so on. The gesture classification module 211508 may determine whether the extracted features correspond to a gesture from a gesture set. In an aspect, the gesture classification module 211508 can include a machine learning model (e.g., an artificial neural network or a support vector machine) that has been trained via supervised or unsupervised learning techniques to correlate a feature vector of the extracted features to one or more output gestures. In another aspect, the gesture classification module 211508 can include a Hu invariant moment-based algorithm or a k-curvature algorithm to classify gestures. In yet another aspect, the gesture classification module 211508 can include a template-matching algorithm programmed to match the featurized image/video data (or portions thereof) to templates corresponding to predefined gestures. Other aspects can include various combinations of the aforementioned techniques and other techniques for classifying gestures.

Upon recognizing a gesture via the gesture recognition module 211504, the gesture recognition system 211500 can take an action 211510 or make a response that corresponds to the identified gesture. For example, the action 211510 taken by the computer system includes controlling a surgical display within the OR.

The action 211510 taken by the computer system may include saving the gestures made by the surgical staff as metadata associated with or linked to the perioperative data generated by the surgical devices during the course of the surgical procedure. Such metadata can be useful in order to determine whether surgical staffs are manually controlling the surgical devices or controlling the surgical devices via gestures, which can in turn be correlated to performances of the surgical staff, procedure times, and other such metrics. In various other aspects, the computer system can both control one or more surgical devices and save the gesture data as metadata.

The gesture recognition system 211500 may utilize a magnetic sensing system for receiving non-contact input from users, in addition to or in lieu of cameras 211802 to visually identify gestures. In this aspect, the gesture recognition system 211500 can include, for example, a magnetic sensing array that can be positioned within the OR.

Gesture recognition is further described in U.S. patent application Ser. No. 16/182,269 titled IMAGE CAPTURING OF THE AREAS OUTSIDE THE ABDOMEN TO IMPROVE PLACEMENT AND CONTROL OF A SURGICAL DEVICE IN USE, filed Nov. 6, 2018, which is incorporated by reference herein in its entirety.

Figure 38:
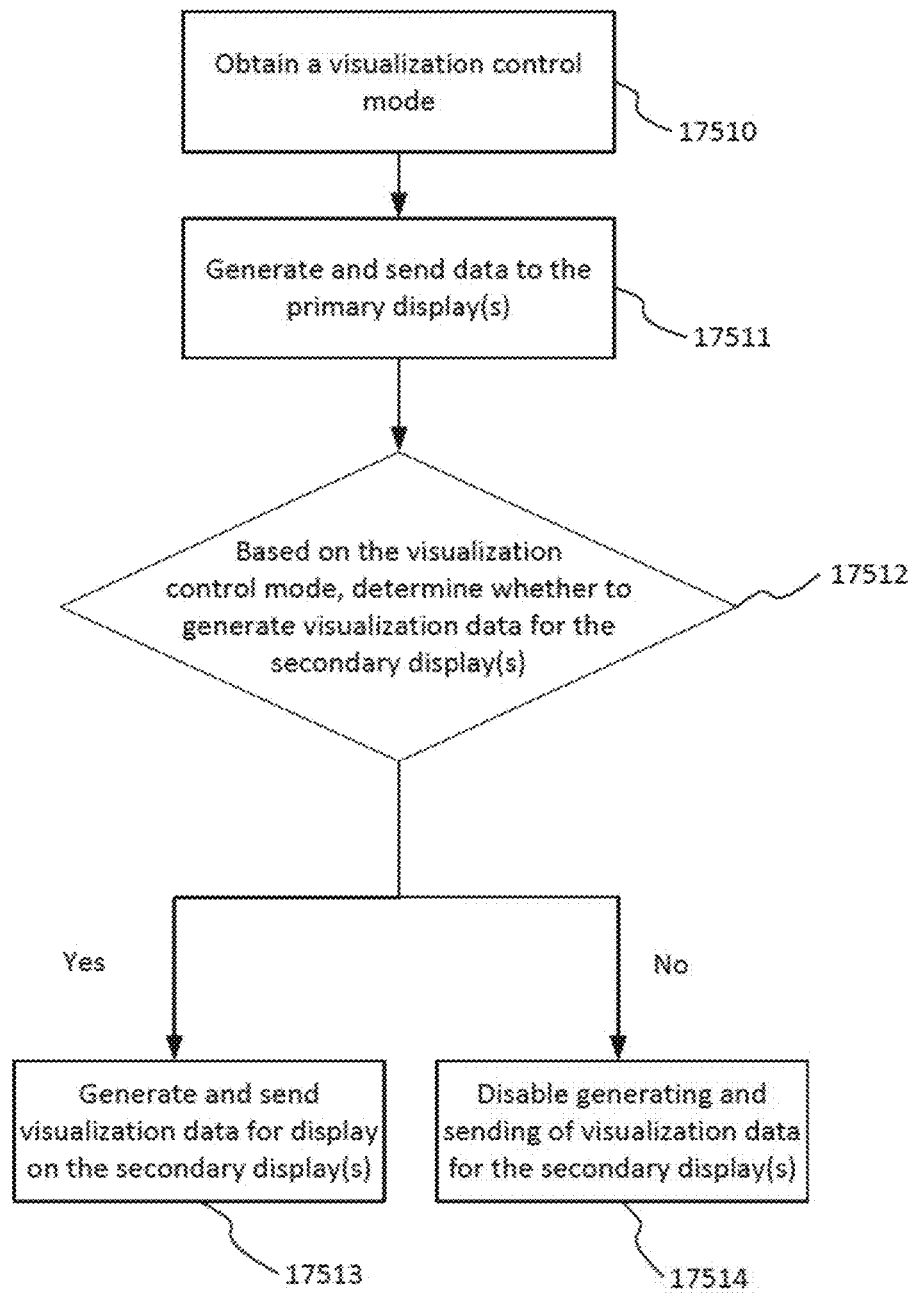
FIG. 38 shows an example flow for a hub operating under tiered visualization control modes.

FIG. 38 shows a detailed example flow for a hub operation under tiered visualization control modes. The hub may obtain a visualization control mode at 17510. At 17511, the hub may generate and send data to the primary display(s) as described herein. At 17512, the hub, based on the visualization control mode, may determine whether to generate visualization data for the secondary display(s).

Some example visualization control mode(s) may support multi-display capabilities, while other example visualization control mode(s) may restrict visualization display to be on the primary display(s) or display the same content on both primary and secondary displays. If the visualization control mode supports multi-display capabilities, at 17513, the hub may generate the visualization data for the secondary display(s) and send the generated visualization data to the respective secondary display(s). If the visualization control mode does not support multi-display capabilities, at 17514, the hub may disable generating and sending of visualization data for the secondary displays and may continue sending the data to the primary displays.

Figure 40:
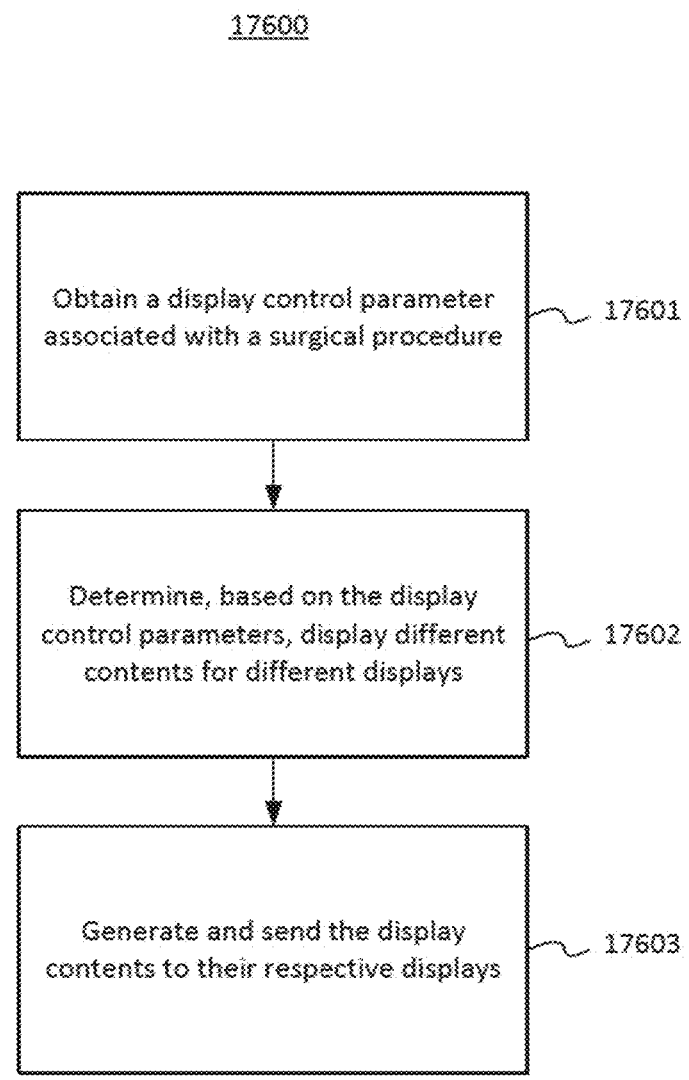
FIG. 40 shows an example flow for a hub operating under a visualization control mode that supports situational awareness capabilities.

FIG. 40 shows an example flow for a hub operating under a visualization control mode that supports multi-display capabilities. At 17601, the hub can obtain display control parameter(s) associated with a surgical procedure. The display control parameter may comprise at least one of: a user's orientation relative to at least one display, a progression of the surgical procedure, a surgical context, and/or the detection of an abnormality associated with the surgical procedure. For example, the display control parameter may be a voice command, a user input via an interactive display, the content type, the intended viewer of the display information, and/or content of information to be displayed.

The hub may determine, based on the display control parameter, different contents for different displays, at 17602. The hub may generate and send the display contents to their respective displays, at 17603.

For example, the display control parameter may be a user's orientation relative to a display. The surgical hub may determine the display content and/or format at one or more displays based on the orientation of the lead surgeons head (or user for which the information is valuable) relative to displays in the OR. The surgical hub may determine the display content and/or format at one or more displays based on user inputs, including user inputs either in or out of the OR. For example, the surgical hub may determine a display location, such as identifying a display, or identify a displaying window within a display, based on the intended viewer of the information and the viewer's relative positions to one or more displays (e.g., each display) in the OR. For example, the surgical hub may select a display closest to the intended viewer of the information. The surgical hub may determine to remove certain display content based on the intended viewer of the information and the viewer's relative positions to various displays in the OR.

In various aspects, controls for a surgical hub, surgical instruments, and other devices can be adjusted based on a screen in operation on a sterile field display. The controls of the surgical devices can be adjusted based on the displayed information. For example, a control that normally controls panning or adjusting the focus of a visualization device (e.g., a scope) can be configured to adjust magnification if a hyperspectral imaging overlay is active, for example. Hyperspectral imaging is further described in U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, which is incorporated by reference herein in its entirety.

For example, the surgeon can control to change, focus, or control that data on the displays. This may enable the healthcare professional to more seamlessly see where they are relative to other imaging or even pre-surgery imaging mechanisms.

The on-handle controls for a surgical instrument in the field of view of a sterile field display can be adjusted by selections on the sterile field display. Moreover, the adjustments can be based on situational awareness in various instances. For example, the system can determine that a particular surgical device is being utilized and permit the functions of that surgical device to be controlled from a second device, such as a display screen within the sterile field.

In an example visualization control mode that supports cooperative display capabilities, multiple displays may be used to display differing aspects of the information or different types of information with relevance to the primary viewer of the display. Some or all of the displays can be controlled by another system that the main hub is only in communication with rather than in control of.

The multiple displays may include but not limited to a primary display on the hub, a visualization tower that may include at least one monitor, displays around the room, and/or tiny device displays.

In an example visualization control mode that supports cooperative display capabilities, the surgical hub may enable a healthcare professional to control a display outside of the sterile field via a display inside the sterile field. During a surgical procedure, the surgeon may not have a user interface device accessible for interactive input by the surgeon and display within the sterile field. Thus, the surgeon may not interface with the user interface device and the surgical hub from within the sterile field and cannot control other surgical devices through the surgical hub from within the sterile field.

For example, a local display, such as a secondary display, may serve as a user interface for displaying and controlling of surgical hub functions from within the sterile field. The secondary display could be used to change display locations, what information is displayed where, pass off control of specific functions or devices. The local display may include a display unit that may be used within the sterile field and accessible for input and display by the surgeon to allow the surgeon to have interactive input control from the sterile field to control other surgical devices and/or displays coupled to the surgical hub. The display unit may be sterile and located within the sterile field to allow the surgeons to interface with the display unit and the surgical hub to directly interface and configure instruments as necessary without leaving the sterile field. The display unit may be a master device and may be used for display, control, interchanges of tool control, allowing feeds from other surgical hubs without the surgeon leaving the sterile field.

The display unit may be or may include an interactive touchscreen display, an interface configured to couple the interactive touchscreen display to a surgical hub, a processor, and a memory coupled to the processor. The memory may store instructions executable by the processor to receive input commands from the interactive touchscreen display located inside a sterile field and may transmit the input commands to a surgical hub to control devices coupled to the surgical hub located outside the sterile field.

The display outside of the sterile field may be or may include the non-sterile display 107 or 109 as shown in FIG. 2. For example, the display inside a surgical sterile field may be or may include a secondary display such as a local display or a display on a surgical instrument. A healthcare personnel may control the secondary display. The primary display(s) and secondary display(s) may have numerous communication levels of operation with the primary hub system. Examples of primary display(s) and secondary display(s) can be found in more detail in U.S. patent application Ser. No. 15/940,671, titled SURGICAL HUB SPATIAL AWARENESS TO DETERMINE DEVICES IN OPERATING THEATER, which was filed on Mar. 29, 2018, which is herein incorporated by reference in its entirety.

Examples of controlling a display outside of the sterile field via a display inside the sterile field are described in a patent application, titled COMMUNICATION CONTROL OPTIONS FOR A SURGEON CONTROLLED SECONDARY DISPLAY AND PRIMARY DISPLAY, filed contemporaneously, which is herein incorporated by reference in its entirety:

Secondary displays may include independent secondary displays and/or dedicated local displays that can be linked to the surgical hub 206 to provide an interaction portal via a touchscreen display and/or a secondary screen that can display any number of surgical hub 206 tracked data feeds to provide a status. The secondary display may display force to fire (FTF), tissue gap, power level, impedance, tissue compression stability (creep), etc., while the primary display may display key variables to keep the feed free of clutter. The interactive display may be used to move the display of specific information to the primary display to a desired location, size, color, etc. In the illustrated example, the secondary display may display the instrument proximity displays 6210 on the left side of the display 6200. The local instrument display 6204 on the bottom right side of the display 6200. The local instrument display 6204 presented on the surgical hub display 6200 may display an icon of the end effector 6218, such as the icon of a staple cartridge 6224 currently in use, the size 6226 of the staple cartridge 6224 (e.g., 60 mm), and an icon of the current position of the knife 6228 of the end effector.

A secondary display may be the display 237 as shown in FIGS. 5 and 6. Referring to FIG. 6, the display 237 located on the instrument 235 can display the wireless or wired attachment of the instrument 235 to the surgical hub 206 and the instrument's communication and/or recording on the surgical hub 206. A setting may be provided on the instrument 235 to enable the user to select mirroring or extending the display to both monitoring devices. The instrument controls may be used to interact with the surgical hub display of the information being sourced on the instrument. The instrument 235 may comprise wireless communication circuits to communicate wirelessly with the surgical hub 206, as described herein.

A first instrument coupled to the surgical hub 206 can pair to a screen of a second instrument coupled to the surgical hub 206 allowing both instruments to display some hybrid combination of information from the two devices of both becoming mirrors of portions of the primary display. The primary display 6200 of the surgical hub 206 can provide a 360° composite top visual view of the surgical site 6208 to avoid collateral structures. For example, a secondary display of the end effector surgical stapler may be provided within the primary display 6200 of the surgical hub 206 or on another display in order to provide better perspective around the areas within a current the field of view 6206.

This secondary display could also be used as a control means for adjusting what and how information is displayed on primary displays outside of the sterile field. This would enable them to better highlight for other surgical personnel information they need to track, be aware of or help with.

These secondary displays could be on instruments, positioned over the patient adjacent to the surgical access ports, or even be worn on the user. These displays could change the multi-spectral imaging, control its overlay on the regular scope feed, overlay the pre-surgical imaging based on established location features, adjust the axillary data displayed around the periphery of the display, or its order, or size, it could even allow the user to move one image or dataset from one location to another on another display.

The primary and the secondary display(s) may be controlled via the gesture recognition system as described herein.

For example, the visualization control parameter may be a progression of the surgical procedure. The surgical hub may determine display contents for the primary and the secondary displays based on the progression of the surgical procedure.

Visualization controls can be adjusted according to the step of the surgical procedure being performed. Situational awareness can inform the surgical hub of the current and/or next step of the surgical procedure. For example, based on the previous surgical actions and/or the order of usage of the surgical device(s) and/or generator(s), a surgical hub can determine what particular step of a particular surgical procedure is being performed, such as whether the procedure is currently in a nodal dissection step, vessel transecting step, and so on. The surgical hub and/or generator can determine the procedural specific step or context.

For example, surgical contextual data can include, the type of surgical procedure being performed, the particular step of the surgical procedure that the surgeon is performing, the type of tissue being operated on, or the body cavity that is the subject of the procedure. This ability by some aspects of the surgical hub to derive or infer information related to the surgical procedure from received data can be referred to as "situational awareness." In one exemplification, the surgical hub can incorporate a situational awareness system, as described herein with reference to FIGS. 9 and 10. A situationally aware surgical hub may derive contextual information pertaining to the surgical procedure from various received surgical data. Such surgical data may include perioperative data from the modular devices 5102 and other data sources (e.g., databases 5122 and patient monitoring devices 5124) that are communicably coupled to the surgical hub 5706.

As described herein, the hub can learn and anticipate the procedural specific step or context by analyzing the particular clinician's most common usage at each stage of the surgical procedure and/or after a particular number or type of surgical instrument exchanges. After monitoring the same clinician's behavior over a predetermined number of procedures that include the same steps, the hub may automatically change content displayed on the display(s) based on the monitored and past display interactions with and/or controls indicated by the clinician. In various instances, the hub can provide notice to the clinician when the display is adjusted. For example, the hub and/or the display(s) can provide an auditory notice (e.g., a beep or verbal explanation), a visual cue (e.g. a flashing light and/or words on a screen), and/or a tactile warning (e.g. vibrations and/or movement of the surgical device or a portion thereof, such as the actuator button itself). In other instances, the surgical hub can recommend a display adjustment. Recommendations from a surgical hub are further described herein.

Figures 41, 42:
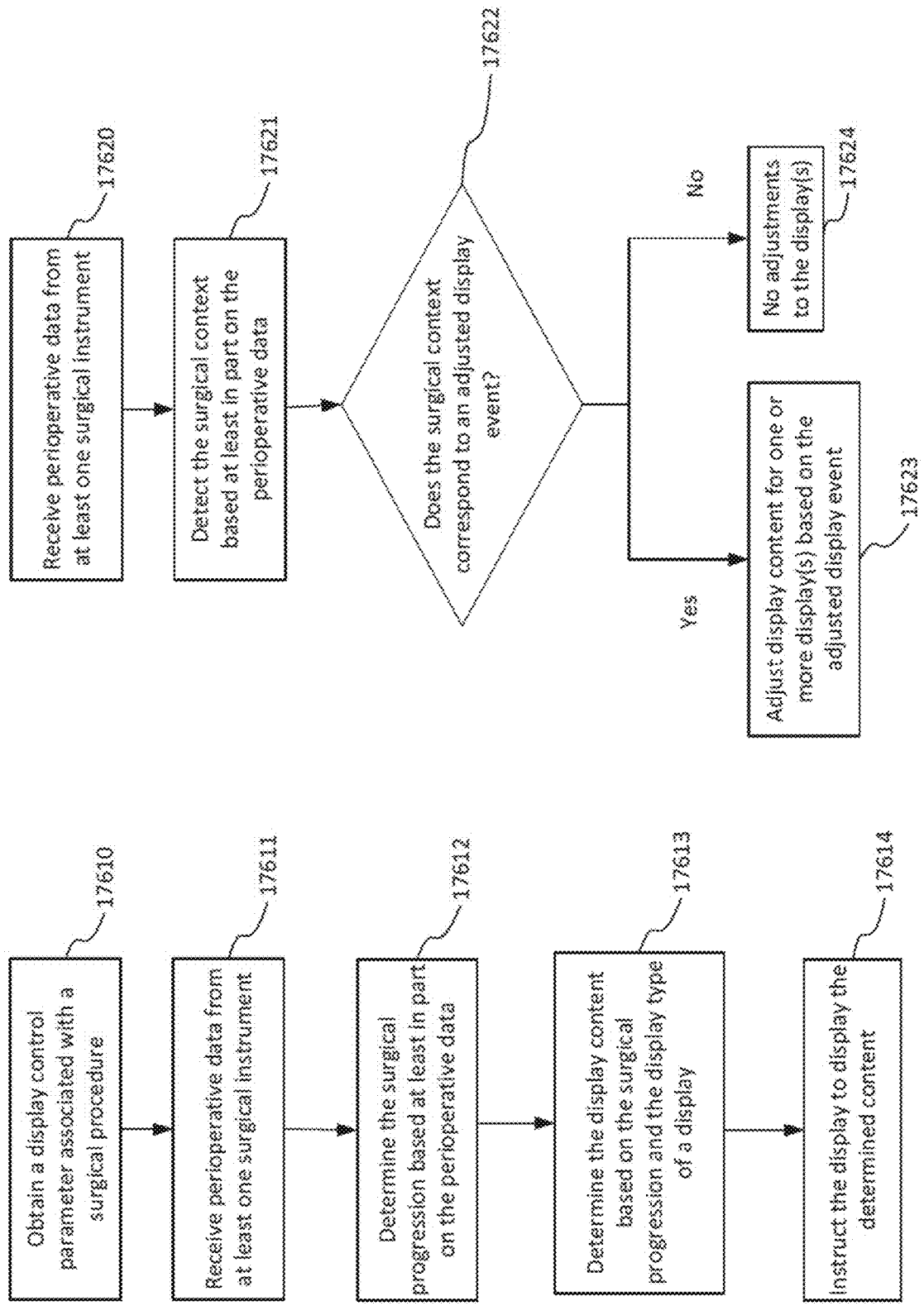
FIG. 41 shows an example flow for a hub operating under a visualization control mode that supports situational awareness capabilities.
FIG. 42 shows an example flow of a hub operating under a visualization control mode that supports adjusting display based on an adjusted display event.

FIG. 41 shows an example flow for a hub operating under a visualization control mode that supports situational awareness capabilities. The hub may obtain a visualization control mode associated with a surgical procedure at 17610. The hub may receive perioperative data from at least one surgical instrument, at 17611. The hub, based on the visualization control mode and at least in part of the perioperative data may determine the surgical progression, at 17612.

Progression of surgical procedure may be determined using a situationally aware surgical system 5100 as shown in FIGS. 9 and 10. For example, a situationally aware hub 5104 may determine what step of the surgical procedure is being performed or will subsequently be performed. The situationally aware hub 5104 may determine whether an event has occurred based on the received data. The event can include, for example, a surgical procedure, a step or portion of a surgical procedure, or downtime between surgical procedures or steps of a surgical procedure. The surgical hub 5104 may track data associated with the particular event, such as the length of time of the event, the surgical instruments and/or other medical products utilized during the course of the event, and the medical personnel associated with the event. The surgical hub 5104 may determine event data via, for example, the situational awareness process as described herein. Situational awareness processes are described in greater detail in U.S. patent application Ser. No. 15/940,654, titled SURGICAL HUB SITUATIONAL AWARENESS, filed Mar. 29, 2018; U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018; and U.S. patent application Ser. No. 16/182,246, titled ADJUSTMENTS BASED ON AIRBORNE PARTICLE PROPERTIES, filed Nov. 6, 2018; the disclosure of each is herein incorporated by reference in its entirety.

Referring back to FIG. 41, based on the determined surgical progression and the types of the displays, the hub may then determine the display content, at 17613. At 17614, the hub may instruct the display to display the determined display content.

Figure 22:
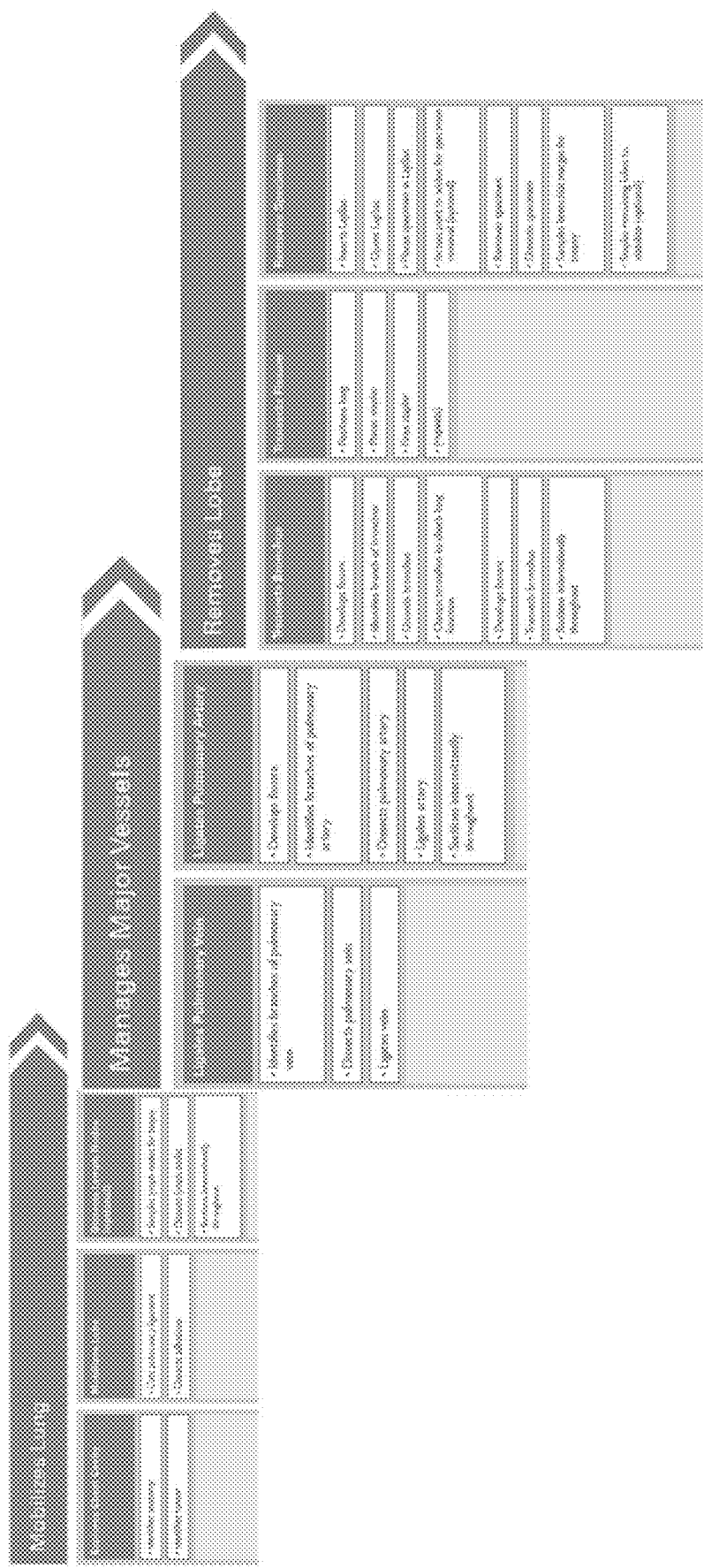
FIG. 22 illustrates example procedural step-based interactions and control related to augmented reality and deviceless control system.

For example, the hub may associate different display contents with different example procedural steps shown in the in FIG. 22. As shown, example surgical steps may include mobilizing the lung, managing major vessels, and removing the lobe. The surgical hub may instruct the display(s) to show information specifically related to a current step in the surgical procedure based on situation awareness and automated control. The surgical hub may determine the type of surgical data for display based on the determined progression of surgical procedure. The surgical hub may select a display among the displays in the OR to display the surgical data base on the determined progression of surgical procedure.

For example, a baseline visualization of an anatomical structure and/or surgical site can be obtained before initiation of a surgical procedure-such as before the manipulation and dissection of tissue at the surgical site. The baseline visualization image of the anatomical geometry can include a visualization of the surface of the anatomical structure and its boundaries. Such a baseline visualization image can be used to preserve overall orientation of the surgical site and anatomic structure even as local regions within the anatomic structure are progressively disrupted, altered, or otherwise manipulated during the surgical procedure.

For example, the surgical hub may update the baseline visualization image upon identifying a particular type of surgical procedure, step in the surgical procedure, type of tissue, and/or one or more specific tissue characteristics. In an example, an updated baseline visualization image can be helpful after a transection or after the application of one or more rows of staples. In certain instances, distorted subregions within an original anatomical structure can separately create a new baseline visualization image or update an existing baseline visualization image for the distorted sub-region(s) to properly inform image overlays. For example, a key region of a patient's anatomy can be updated after removal of a tumor or growth therein.

Figure 23:
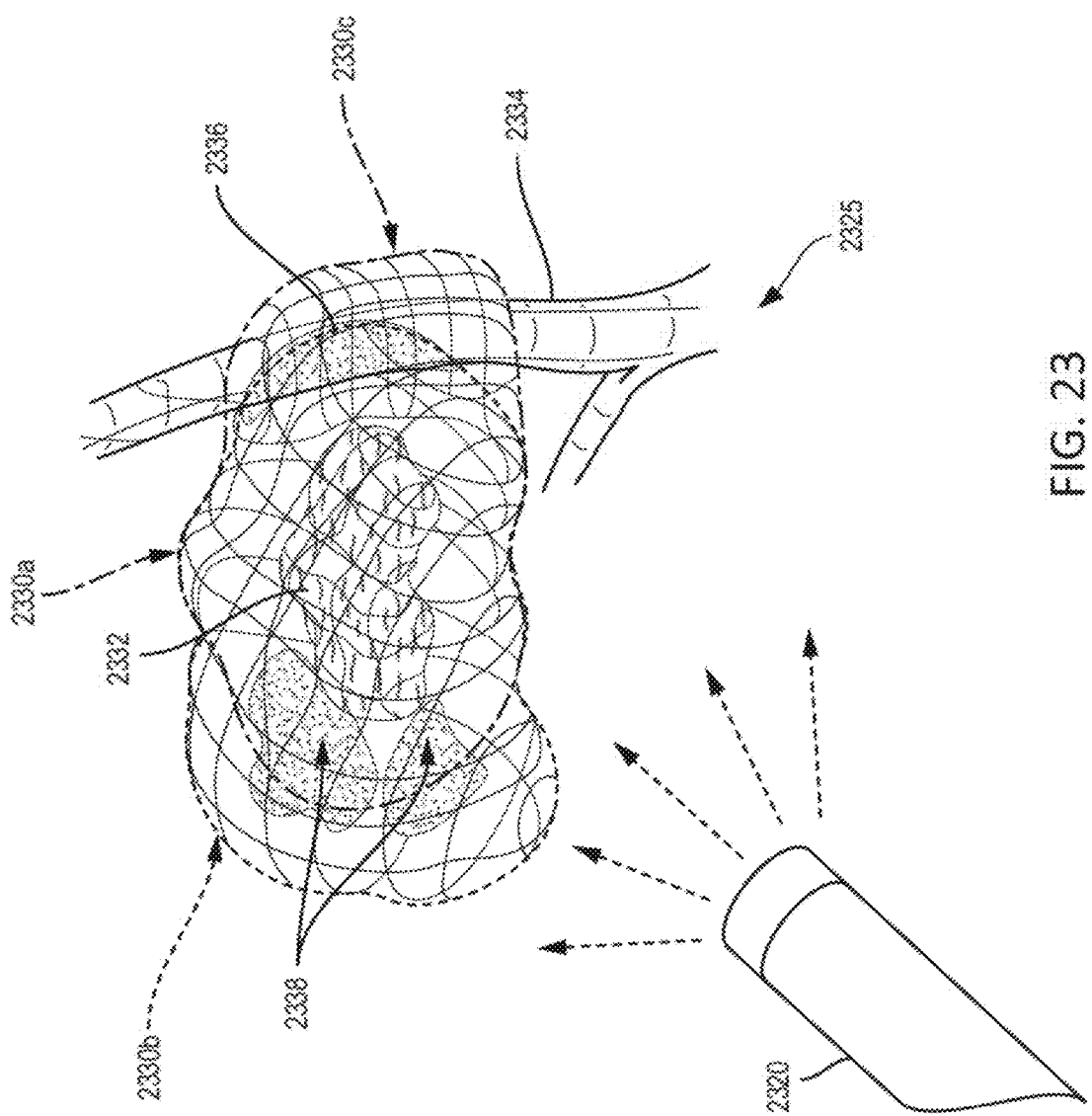
FIG. 23 is a schematic of an example visualization of anatomical structures via a spectral surgical visualization system.

For example, the surgical hub may generate display content using spectral imaging techniques to visualize different tissue types and/or anatomical structures as shown in FIG. 23. In FIG. 23, a spectral emitter 2320 (e.g., spectral light source 150) can be utilized by an imaging system to visualize a surgical site 2325. The EMR emitted by the spectral emitter 2320 and reflected from the tissues and/or structures at the surgical site 2325 can be received by an image sensor to visualize the tissues and/or structures, which can be either visible (e.g., be located at the surface of the surgical site 2325) or obscured (e.g., underlay other tissue and/or structures at the surgical site 2325). In this example, an imaging system can visualize a tumor 2332, an artery 2334, and various abnormalities 2338 (i.e., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system, such as an imaging system display, a primary display, a non-sterile display, a hub display, a device/instrument display, and so on.

The surgical hub may tailor or update the displayed surgical site visualization according to the identified tissue and/or structure types. For example, a margin 2330a associated with the tumor 2332 being visualized may be displayed on a display. The margin 2330a can indicate the area or amount of tissue that should be excised to ensure complete removal of the tumor 2332. A control system can be configured to control or update the dimensions of the margin 2330a based on the tissues and/or structures identified by the imaging system. In the illustrated example, multiple abnormalities 2338 may be identified within the FOV. Accordingly, the control system can adjust the displayed margin 2330a to a first updated margin 2330b having sufficient dimensions to encompass the abnormalities 2338. Further, an artery 2334 may be identified to be partially overlapping with the initially displayed margin 2330a (as indicated by the highlighted region 2336 of the artery 2334). The surgical hub may adjust the displayed margin 2330a to a second updated margin 2330c having sufficient dimensions to encompass the relevant portion of the artery 2334.

For example, upon determining that the next surgical step is resecting a portion of tissue, the surgical hub may display estimated changes in deformation for a proposed resection on a display. The proposed resection line(s) can be added to the digital model, which can be updated to show the anatomical structure with the hypothetical resection. Referring again to FIG. 13B, in one example, a clinician may intend to remove a wedge-shaped portion from the tissue at the surgical site 2325 to remove the tumor 2332 along with the tissue abnormalities 2338. In such instances, the model can be updated to show the organ with the wedge-shaped portion removed therefrom. The updated model can depict the deformation of the tissue, as well as the computed stress and/or strain in the tissue based on the known tissue mechanical properties and the deformation induced by the surgery. For example, the tissue can be shaded or otherwise layered with the stress and/or strain data so that the clinician is informed regarding how a particular resection may impact strain on the tissue. In some aspects, the stress/strain data may be overlaid on the image as a set of vector lines indicating stress/strain direction and line type or color to indicate the value of the stress/strain. Based on the computed stresses and strains, a clinician may modify the proposed resection and consider an alternative strategy to reduce and/or better distribute the stresses and strains within the tissue. For example, the angles of the resections can be modified. In certain instances, the clinician can reorient a staple line with a preferred strain direction.

Figure 24:
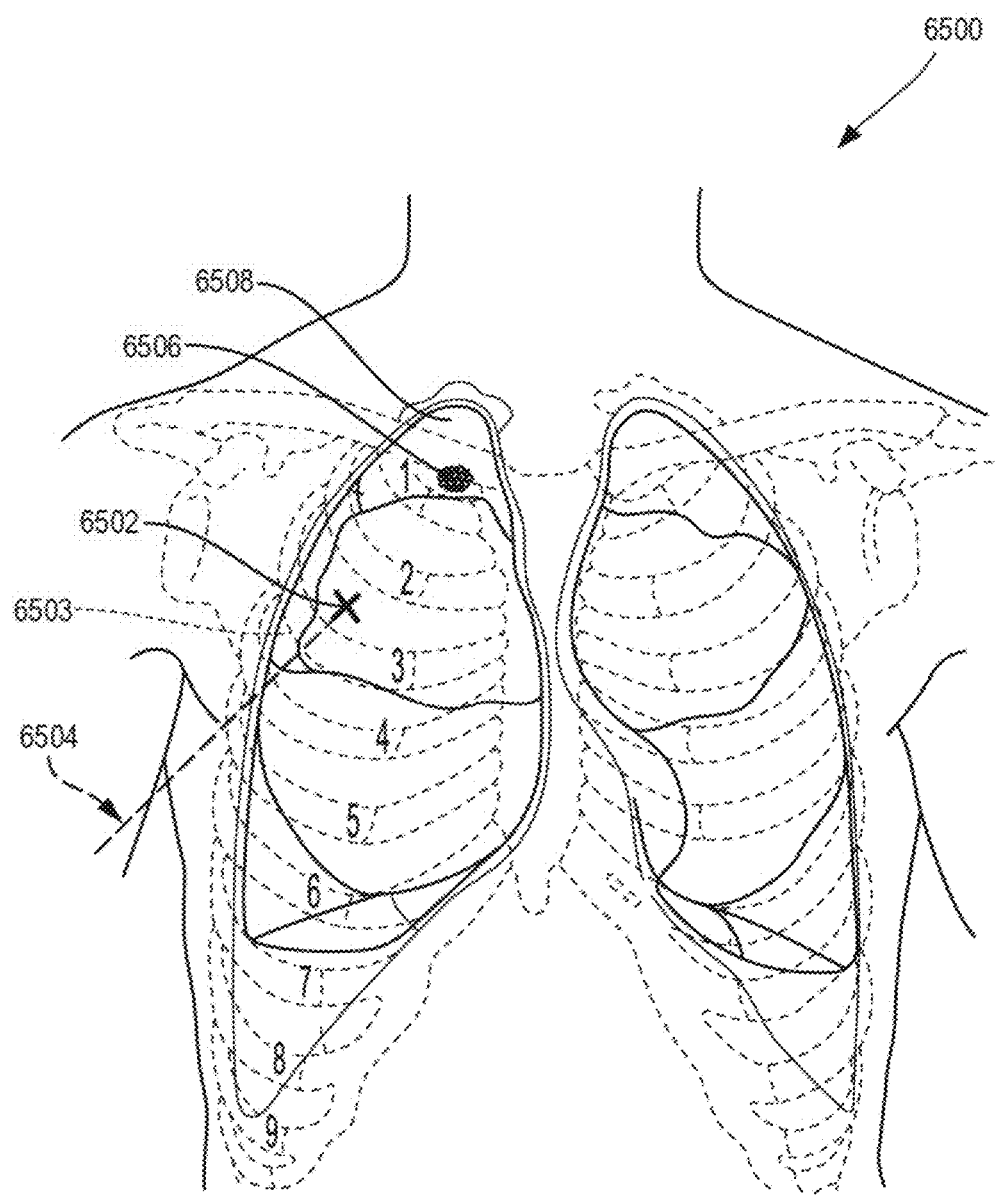
FIG. 24 is a diagram of a surgical instrument access path for a video-assisted thoracoscopic surgery (VATS) procedure, in accordance with at least one aspect of the present disclosure.
Figure 25:
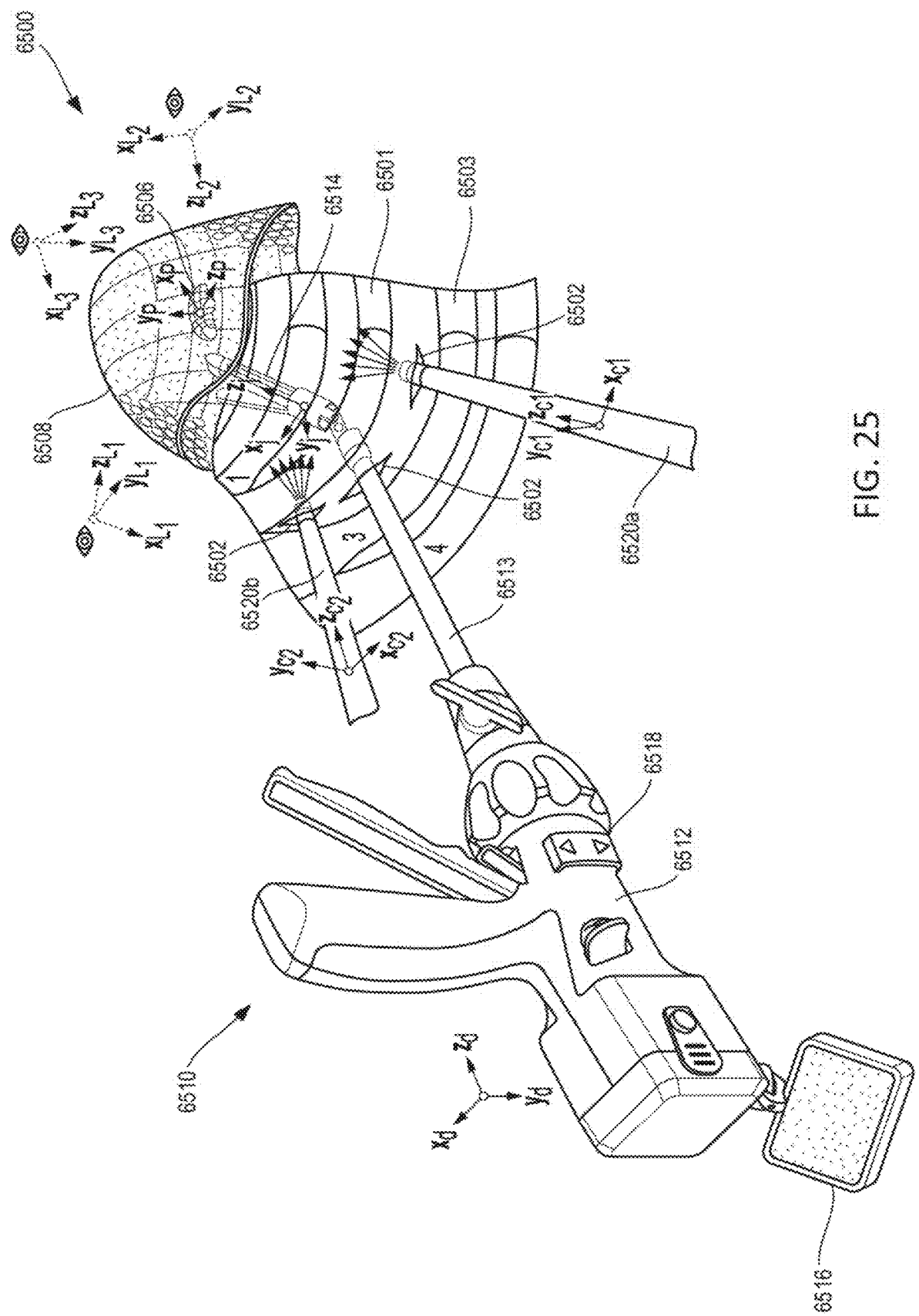
FIG. 25 is a diagram of various coordinate systems associated with a VATS procedure, in accordance with at least one aspect of the present disclosure.

For example, upon determining that the surgical procedure is a video-assisted thoracoscopic surgery (VATS) procedure, the surgical hub may instruct one or more display(s) to show example contents shown in FIGS. 24 and 25. A VATS procedure is a surgical procedure whereby one or more surgical instruments and one or more thoracoscopes (i.e., cameras) are inserted into the patient's chest cavity through slits positioned between the patient's ribs. The cameras are utilized to provide the surgeons with a view of the interior of the patient's chest cavity to allow the surgeon to properly position/move the surgical instrument(s) and manipulate tissue/structures within the chest cavity. Because the surgeon controls the surgical instrument(s) based on what is displayed by the imaging system via the camera(s) and because the surgical instrument(s) may not be aligned with the viewing perspective of the camera(s), the spatial relationship between the surgical instrument and the POV displayed by the imaging system can be potentially disorienting, especially for imaging systems that allow users to pan, manipulate, and reorient the displayed visualization.

FIGS. 24 and 25 show example display content associated with a VATS procedure. In this particular VATS procedure, the surgeon may seek to remove a tumor 6506 located within the apical segment of the superior lobe of a lung 6508. As shown, the surgeon has placed a port 6502 between the second rib 6501 and the third rib 6503 to provide an access path 6504 for a surgical instrument 6510 (e.g., a surgical stapler) insertable through the port 6502 to access the tumor 6506 and/or the surrounding area within the chest cavity. Once the location of the access for the surgical instrument 6510 has been selected, the surgeon can place one or more cameras 6520a, 6520b through other ports 6502 that are positioned to allow the camera(s) 6520a, 6520b to visualize the interior of the patent chest cavity in the vicinity of the surgical site. Visualizing the surgical site in this manner allows the surgeon to position and orient an end effector 6514 of the surgical instrument 6510 to manipulate the tissue as needed (e.g., excise a portion of the lung 6508 around the tumor 6506). In the particular illustrated example, two cameras 6520a, 6520b are utilized, although a different number of cameras can be utilized and/or one or more of the cameras 6520a, 6520b can be oriented in a different manner depending upon the particular type of surgical procedure that is being performed and/or the region within the body of the patient 6500 that needs to be visualized.

For example, when operating under an example visualization control mode, the surgical hub may adjust a secondary display, such as a local display attached to a surgical instrument, based on a local coordinate system. The local coordinate system may be a surgical visualization coordinate system. Upon determining that the surgical procedure is a VATS procedure, the surgical hub may send a locally displayed coordinate system to a surgical instrument or other medical device to enable the instrument/device controls to be adapted to control motion relative to a local visualization coordinate system. At least one measurement derived from the imaging system can be utilized to define the local coordinate system. User controls displayed on the local display may be reoriented relative to the local coordinate system, rather than a standard global coordinate system or another coordinate system.

As shown in FIG. 25 and set forth below in TABLE 1, a variety of different coordinate systems can be defined with respect to the differing POVs of the patient, devices, or device components. Further, when operating under a visualization control mode that allow users to manipulate the displayed visualization, "virtual" POVs can be defined that correspond to the virtual or predicted visualization being displayed to the surgeon and coordinate systems can also be defined according to these POVs. The generation and control of such visualizations are further described herein.

TABLE 1

| Coordinate System | Description |
| --- | --- |
| $x_p, y_p, z_p$ | Patient anatomical plane POV |
| $x_d, y_d, z_d$ | Handle assembly POV |
| $x_j, y_j, z_j$ | End effector/cartridge POV |
| $x_{c1}, y_{c1}, z_{c1}$ | Camera #1 POV |
| $x_{c2}, y_{c2}, z_{c2}$ | Camera #2 POV |
| $x_{L1}, y_{L1}, z_{L1}$ | Virtual local POV #1 |
| $x_{L2}, y_{L2}, z_{L2}$ | Virtual local POV #2 |
| $x_{L3}, y_{L3}, z_{L3}$ | Virtual local POV #3 |

The coordinate systems can be defined based upon sensor measurements and/or measurements by the imaging system. For example, a coordinate system with respect to a surgical instrument handle assembly 6512, a shaft 6513, or the end effector 6514 could be defined according to measurements by an accelerometer or another such sensor associated with the respective components. As another example, any of the aforementioned coordinate systems could be defined based upon measurements of the relative distances and/or positions of objects with respect to each other or a global coordinate system as determined by imaging the objects via the imaging system.

Figure 26:
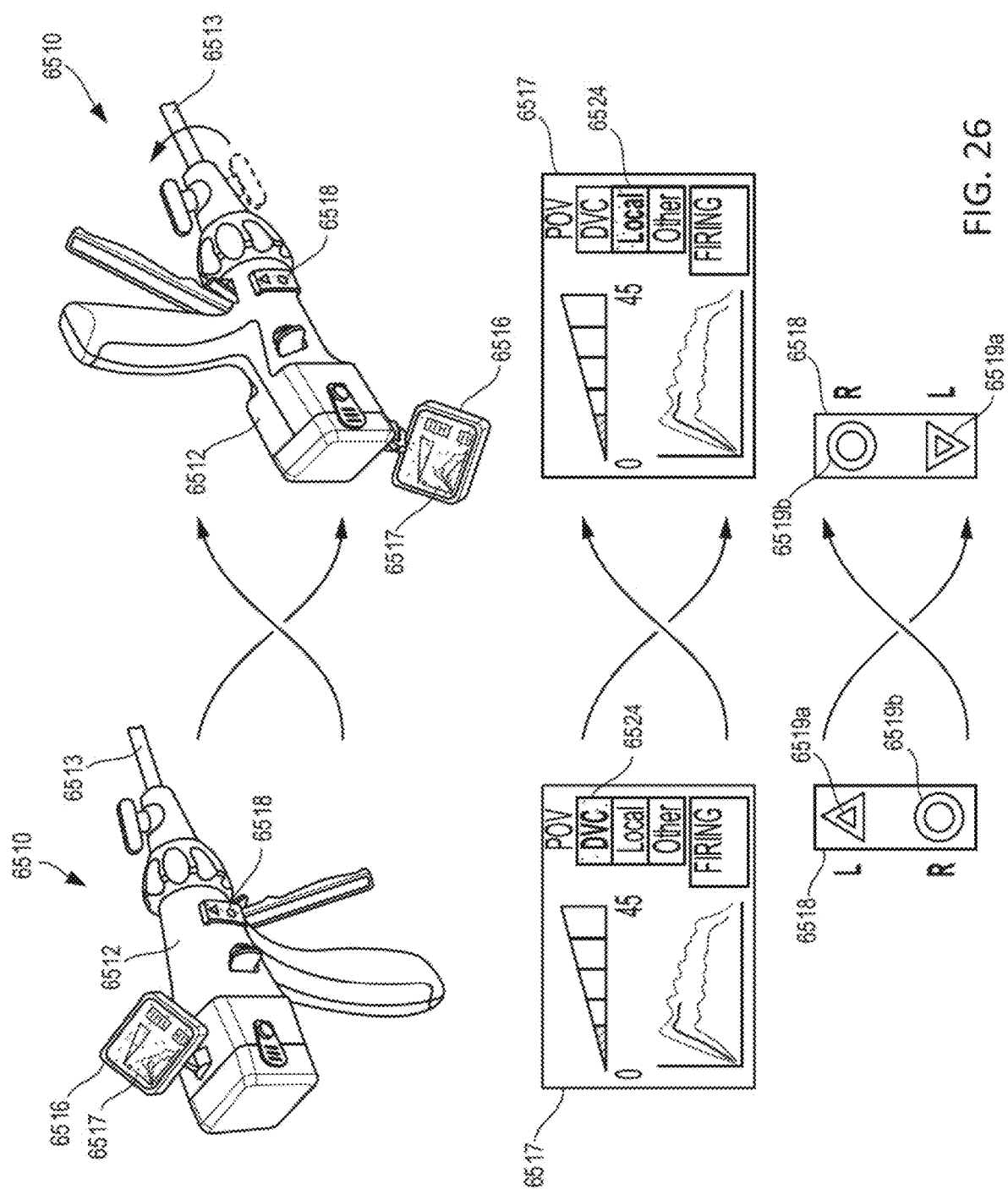
FIG. 26 is a diagram depicting an example change in orientation of a display and user controls in response to a change in orientation of the surgical instrument.

In the example shown in FIG. 26, the surgical instrument 6510 has utilized the provided transfer function to determine that the controls 6518 and display screen 6516 should be adjusted based on the updated coordinates. In various instances, situational awareness, as further described herein, can inform when the controls 6518 and/or the display screen 6516 are updated. The display screen 6516 can display a GUI 6517 that is adjusted from a first orientation, shown on the left side of FIG. 26, to a second orientation, shown on the right side of FIG. 26, to ensure that the GUI 6517 is oriented properly for the surgeon controlling the surgical instrument 6510. In one aspect, the GUI 6517 can further include a GUI element 6524 (e.g., an icon) indicating the POV or coordinate system being utilized by the surgical instrument 6510. In this example, the GUI element 6524 shifts to indicate that the POV displayed by the visualization system 2108 has changed from the device coordinate system ("DVC") to the local coordinate system ("Local") associated with the image/video displayed by the visualization system 2108.

As an example, the surgical instrument controls 6518 that are adjusted according to the updated coordinates can include articulation controls. The articulation controls can include a first control 6519a configured to cause the surgical instrument 6510 to articulate in a first direction and a second control 6519b configured to cause the surgical instrument 6510 to articulate in a second direction, for example. The articulation controls 6519a, 6519b can be embodied as a rocker, toggle, or separate actuators and/or buttons, for example. In this example, the surgical instrument 6510 has caused the first articulation control 6519a and the second articulation control 6519b to swap functions in response to the change in orientation of the surgical instrument 6510. In other words, actuating the first articulation control 6519a would instead cause the surgical instrument 6510 to articulate in the second direction, and actuating the second articulation control 6519b would cause the surgical instrument 6510 to articulate in the first direction. Accordingly, the functions of the articulation controls 6519a, 6519b can be set according to the orientation of the surgical instrument 6510 or a component thereof (e.g., the end effector 6514) as displayed to the user.

Additionally, or alternatively, in certain instances, the GUI 6517 on the display screen 6516 can be adjusted. For example, the GUI 6517 can be inverted when the handle assembly 6512 is inverted. In certain instances, the GUI 6517 can include a touch screen such that the surgeon can switch between coordinate systems by interacting with the GUI 6517. For example, the surgeon can toggle between a device POV, local POV, and/or one or more other POVs by interacting with the GUI 6517.

When operating under an example visualization control mode, the surgical hub may fuse images from different sources to expand visualization field scope, for example upon determining that the current surgical step may benefit from an expanded visualization field scope. For example, the surgical hub may generate and send fused images from different sources when upon determining that the current surgical step is dissecting a vessel.

3D representations of objects within the visualization field of the imaging system may be created, and the 3D shapes may be characterized to allow users to alter the displayed visualization with respect to the established coordinate system to better visualize the surgical site. The 3D representations can be generated from images generated from real-time sources or non-real-time sources (e.g., CT scans or MRIs). In one aspect, structured light, or structured EMR may be projected to create structured 3D shapes that can be tracked in real time. These 3D shapes could be generated in such a manner as to allow the POV displayed by a display to be moved or rotated away from the scanning source's local coordinate system to improve the perspective view of the user through the display.

Figure 27:
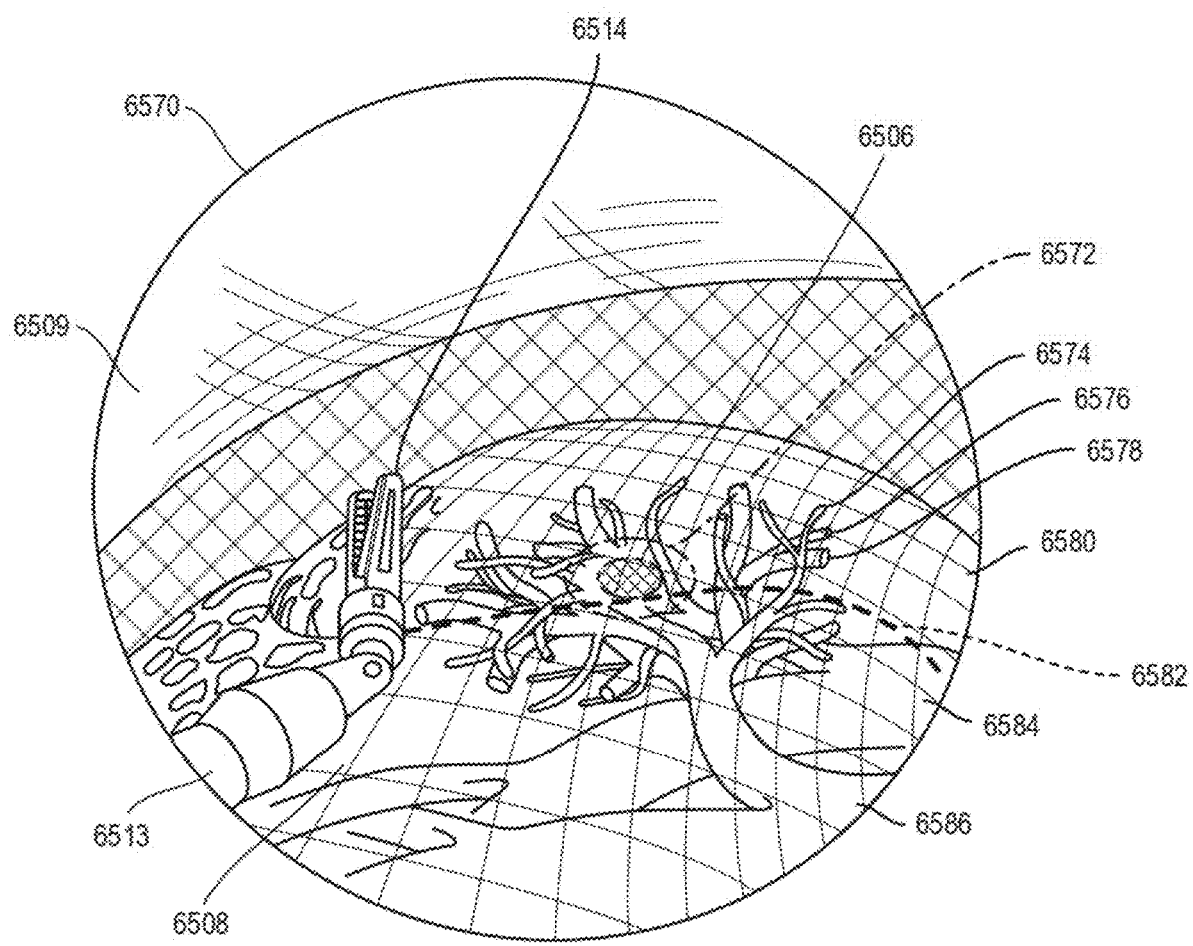
FIG. 27 depicts an example camera view of a surgical procedure.

FIG. 27 illustrates an example FOV 6570 of a camera during a VATS procedure. The target of this particular illustrative procedure is a tumor 6506 located within the apical segment of the superior lobe 6580 of a lung 6508. A number of biological structures are identifiable within this FOV 6570, including the thoracic wall 6509, veins 6574, arteries 6576, bronchi 6578, the fissure 6582 delineating the superior lobe 6580, a pulmonary artery 6584, and a pulmonary vein 6586. Non-biological objects are also viewable within the FOV 6570, including the end effector 6514 and the shaft 6513 of the surgical instrument 6510 being controlled by the surgeon. In an example imaging system, such a view, in combination with any corresponding views from any additional camera(s) 6520 being utilized, would be the sole view(s) available to surgeons performing a video-assisted procedure. Although the cameras are placed with the intent to provide the surgeon with an adequate visualization field scope for performing the surgical procedure, the visualization field scope provided by the camera(s) 6520 may ultimately not provide the ideal FOV 6570 for performing each step or task in the surgical procedure, or unexpected obstructions may be present at the surgical site that impede the surgeon's view. Further, intraoperatively repositioning or reorienting the camera(s) 6520 can be impractical or undesirable in certain instances due to the surgical constraints of the procedure.

A surgical system can be configured to expand the visualization field scope provided by the camera(s) by combining multiple images of the surgical site, including preoperative images and intraoperative images, to generate 3D representations of the surgical site or tissues and/or structures located at the surgical site. During the surgical procedure, the user can then manipulate the 3D representations displayed by the imaging system 142 to visualize the surgical site from orientations that are outside the scope of the FOV 6570 of the camera(s) being utilized in the procedure. Such reoriented views can be referred to as "virtual POVs," as noted above. Accordingly, the surgical system can supplement the FOV 6570 provided by the camera(s) and allow surgeons to dynamically adjust the displayed visualization of the surgical site during the surgical procedure to find ideal viewing POVs for performing one or more of the surgical tasks.

Locally displayed coordinate system is further described in U.S. patent application Ser. No. 16/729,747 titled DYNAMIC SURGICAL VISUALIZATION SYSTEMS, filed Dec. 31, 2019, which is incorporated by reference herein in its entirety.

FIG. 42 shows an example flow of a hub operation under a visualization control mode that supports adjusting display based on an adjusted display event. At 17620, the hub may receive data from at least one surgical instrument. At 17621, the hub may detect the surgical context based at least in part on the perioperative data. The hub may determine, based on the surgical context whether the surgical context correspond to an adjusted display event, at 17622. If the surgical context includes an adjusted display event, the hub may then adjust display content for one or more displays based on the adjusted display event, as described in 17623. The adjusted display event may include a stressful procedure step, a critical procedure step, and/or a pre-defined procedural step.

For example, the surgical hub may adjust the display format and/or content at a display to a focused mode, upon determining that the current surgical step is a stressful procedure step, a critical procedure step, or a pre-defined procedural step.

Figure 33:
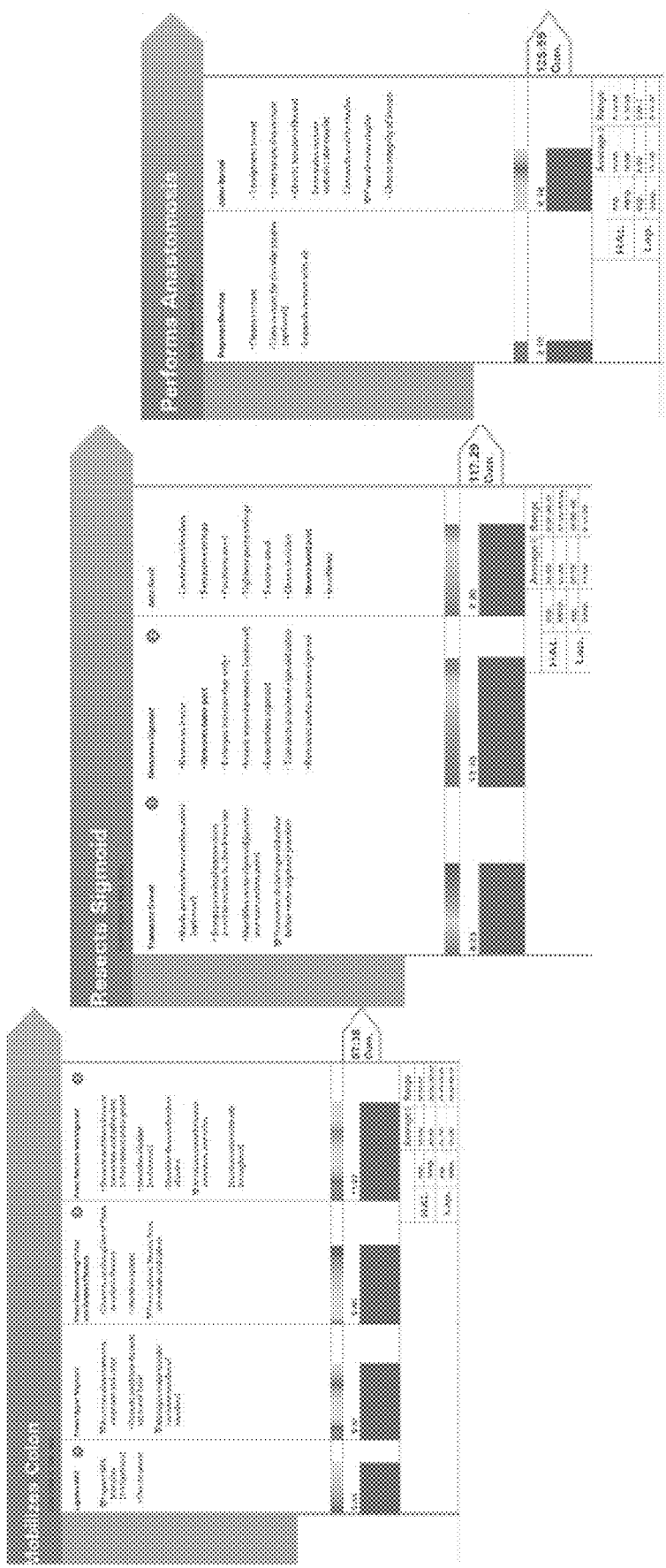
FIG. 33 illustrates example procedural steps and progression that may be detected by example situation awareness capabilities of the system.

FIG. 33 illustrates example procedural steps and progression that may be detected by example situation awareness capabilities of the system. Certain steps may be considered important to the success of the surgery or may be associated with heightened stress level. For example, ligating IMA branches, accessing plane between omentum and colon, managing major bleeder, freeing splenic flexure from omentum and spleen and colon as shown under segment "mobilizes the colon" may be considered a stressful procedure step by the surgical hub. As shown in FIG. 33, steps such as transecting distal sigmoid colon below recto-sigmoid junction under segment "resects sigmoid" and firing circular stapler under segment "performs anastomosis" may be considered stressful procedure steps that may warrant display content and/or format change(s).

For example, display content may be adjusted by zooming in on a target in an image, removing extraneous information from the first display content and/or emphasizing a portion of a laparoscopic scope image.

The adjusted display event may include a detection of an abnormality associated with the surgical procedure, received surgical data being outside of expected value range, or a system parameter being outside of desirable system parameter range. The display content may be adjusted by projecting a warning, error message, or an indication of the detected abnormality on a hub display (e.g., the main monitor). The display content may be adjusted by overlaying a warning, error message, or an indication of the detected abnormality on the display.

The adjusted display event may include a detection of steps for use being out of sequence. For example, procedural steps for use of a surgical instrument may be displayed on a device screen such as display attached to the surgical instrument. Based on the surgical context based at least in part on the perioperative data received, a situational aware hub may detect that the steps for use of the surgical instrument are out of sequence. Upon detection, the display content on the primary display (e.g., the main screen) may be adjusted to show an indication of the steps for use of the surgical instrument being out of sequence. If an early action is identified, the surgical hub may instruct the primary display to show an indication of a recommended step. For example, upon sensing that firing trigger is being pulled prior to clamp time, the surgical hub may adjust the display content on the primary display to show an indication to direct user to wait or a countdown prior to firing.

In examples, display content may be adjusted by moving certain data to another display. An interactable display may receive a user indication, for example, from a healthcare professional, such as a surgeon, that indicates a selection of where the data is to be displayed. The selection may be indicated for a specific surgical step, for stressful procedure step(s), critical procedure step(s) and/or in the event an abnormality associated with the surgical procedure is detected. The content may be sent to the selected display location for display.

Referring back to FIG. 42, if the surgical context does not include an adjusted display event, the hub may refrain from making additional adjustments to the displays at 17624.

In examples, the hub, in communication with the AR devices and at least one smart surgical device, can provide interactive overlay of a surgical display superimposing information onto another surgical display. The surgical display may connect to an AR device in a surgical suite. The AR device may overlay or superimpose additional datasets or data streams received from the hub onto a display such as a surgical display or a display on a smart device. This interactive overlay may enable the user of the AR device to layer data on a screen when the user is looking at the screen. The surgical hub may adjust the layer data based on the display the user is viewing. For example, the hub may adjust the layer data when the user looks from one display to another display. The AR device can adjust the displayed data on the monitor or the device screen. For example, a display control indication may be received from an AR device. In response, the surgical hub may adjust the content for displaying on the monitor or the device screen based on the received display control indication.

The AR device may provide auditory overlay, for example, in addition to hearing OR sounds rather than in place of them. The AR system may communicate certain information only to the targeted individual within the OR that could utilize the information.

The AR content may be enabled or disabled based on the location of the AR device. For example, the surgical hub may detect that the AR device is outside of the bounds of a surgical operating room. In response, the surgical hub may disable sending AR content to the AR device.

Figure 39:
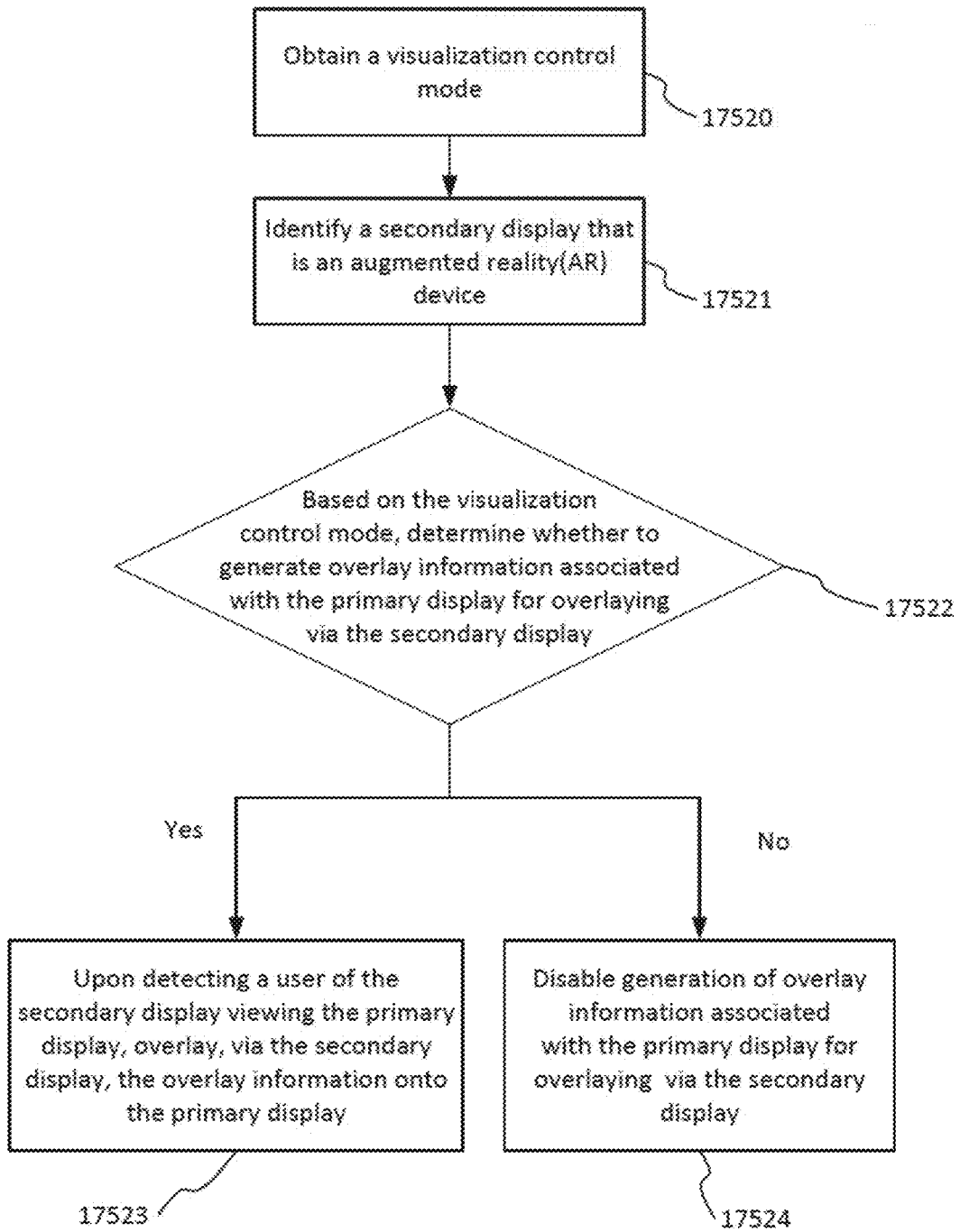
FIG. 39 shows a detailed example flow for a hub operating under a visualization control mode where the secondary display is an augmented reality (AR) device.

FIG. 39 shows an example flow for a hub operation under a visualization control mode where the secondary display is an augmented reality (AR) device. At 17520, the hub may obtain a visualization control mode. The hub may identify a secondary display that is an AR device, at 17521.

As shown in FIG. 39, the hub, at 17522, may determine whether to generate overlay information associated with the primary display for overlaying via the secondary display based on the visualization control mode. If the visualization control mode does support AR capabilities, the hub may disable generation of information associated with the primary display for overlaying via the secondary display, at 17524.

A secondary display may be or may include an AR device. The AR device may include a head-mounted display (HMD). An HMD may include a processor, a non-transitory computer readable memory storage medium, and executable instructions contained within the storage medium that are executable by the processor to carry out methods or portions of methods disclosed herein. The HMD may include a graphics processor for rendering 2D or 3D video and/imaging for display.

Figure 18:
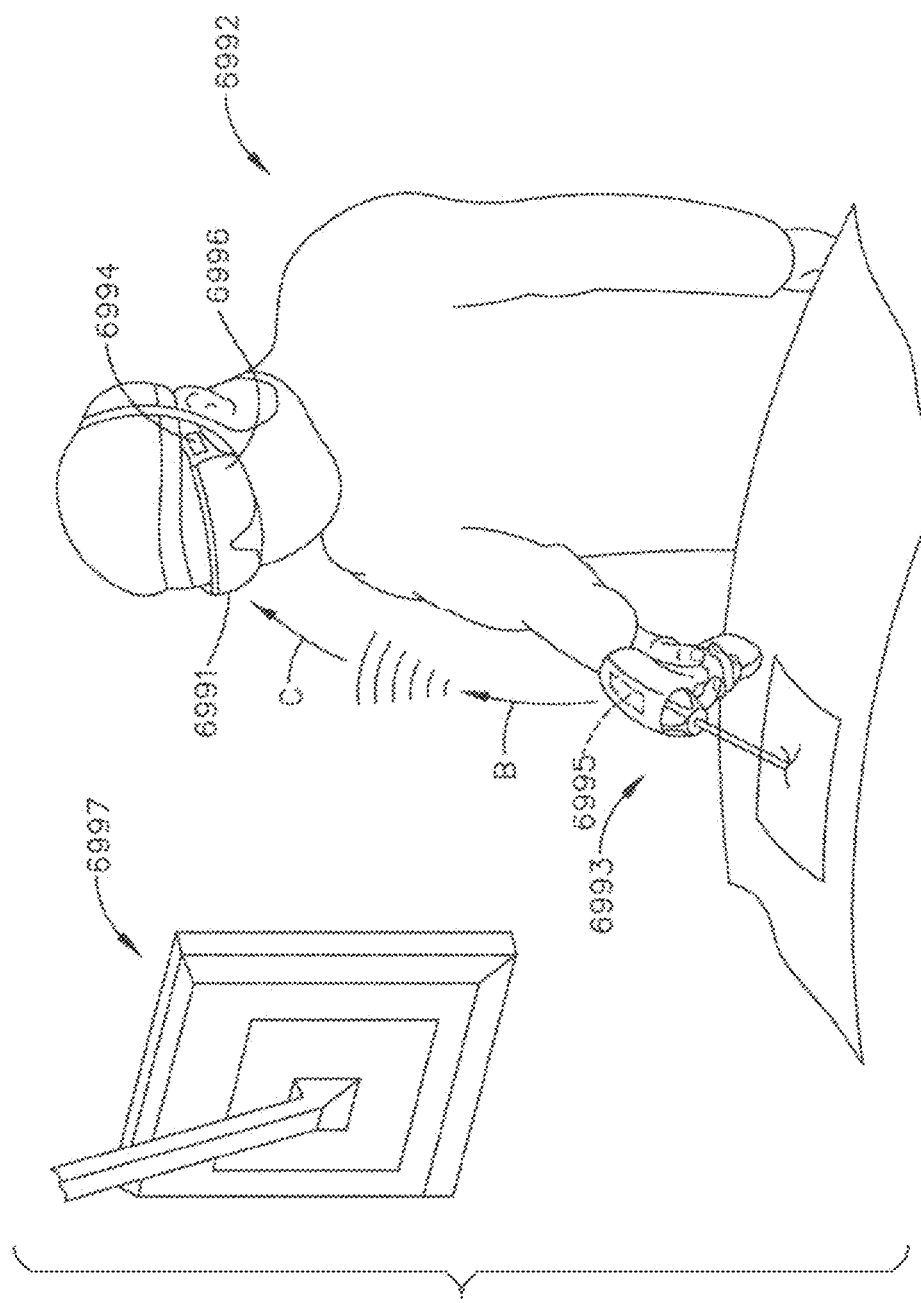
FIG. 18 depicts a perspective view of a surgeon using a surgical instrument that includes a handle assembly housing and a wireless circuit board during a surgical procedure, with the surgeon wearing a set of safety glasses.

FIG. 18 depicts a perspective view of a surgeon using a surgical instrument that includes a handle assembly housing and a wireless circuit board during a surgical procedure, with the surgeon wearing a set of safety glasses. The safety glasses may be or may include an AR device that may serve as a secondary display. The wireless circuit board transmits a signal to a set of safety glasses worn by a surgeon using the surgical instrument during a procedure. The signal is received by a wireless port on the safety glasses. One or more lighting devices on a front lens of the safety glasses may change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 18 shows a version of safety glasses 6991 that may be worn by a surgeon 6992 during a surgical procedure while using a medical device. In use, a wireless communications board housed in a surgical instrument 6993 may communicate with a wireless port 6994 on safety glasses 6991. Exemplary surgical instrument 6993 is a battery-operated device, though instrument 6993 could be powered by a cable or otherwise. Instrument 6993 includes an end effector. Particularly, wireless communications board 6995 transmits one or more wireless signals indicated by arrows (B, C) to wireless port 6994 of safety glasses 6991. Safety glasses 6991 receive the signal, analyze the received signal, and display indicated status information received by the signal on lenses 6996 to a user, such as surgeon 6992, wearing safety glasses 6991. Additionally, or alternatively, wireless communications board 6995 transmits a wireless signal to surgical monitor 6997 such that surgical monitor 6997 may display received indicated status information to surgeon 6992, as described above.

A version of the safety glasses 6991 may include lighting device on peripheral edges of the safety glasses 6991. A lighting device provides peripheral-vision sensory feedback of instrument 6993, with which the safety glasses 6991 communicate to a user wearing the safety glasses 6991. The lighting device may be, for example, a light-emitted diode ("LED"), a series of LEDs, or any other suitable lighting device known to those of ordinary skill in the art and apparent in view of the teachings herein.

As shown in FIG. 39, if the visualization control mode supports AR capabilities, at 17523, the hub may overlay, via the secondary display, the overlay information onto the primary display upon detecting a user of the secondary display viewing the primary display.

In an example, the primary display may display a livestream of a surgical site in the surgical operating room from a medical imaging device, and the secondary display may be AR glasses. As an example, a doctor performing a laparoscopic surgery wearing AR glasses may see the image of the tumor overlay on the screen. When the hub detects that the doctor is looking down at the patient (e.g., via gesture recognition described herein, via HMD-based motion tracking, via image recognition based on images captured by the AR glasses), the hub may instruct the AR glasses overlay the laparoscopic images with AR content with the orientation of the devices inside the patient. This may allow the doctor to see an overlay with the orientation of the devices inside the patient. As the tumor is in three-dimensional space, although the doctor can only see the outside draping of the tissue, with the help of the AR glasses, the doctor can better orient the surgical instrument.

The surgical hub, communicating with the specific AR devices, can generate and send different overlays based on the targeted displays within the OR. The users can observe different overlays when they look at different displays without interfering with each other. The hub can adjust information contained in the overlays based on different displays within the OR room, the specific situation, information received from surgical devices, specific user requirements, and/or the specific operation procedure.

In an example visualization control mode that supports targeted AR content, individual users may have different display devices that may work in concert with a shared display. Different display devices may be provided with different AR content for overlaying on the shared display. This may allow the users to view personally directed information or overlaid data that only they can view and/or interact with. Example interactive surgical systems are described in detail in U.S. patent application Ser. No. 15/940,671, titled SURGICAL HUB SPATIAL AWARENESS TO DETERMINE DEVICES IN OPERATING THEATER, which was filed on Mar. 29, 2018, which is herein incorporated by reference in its entirety.

The augmentation of the user's perceptions could be visual, for example, via AR glasses or local display. For example, FIG. 28, FIGS. 34A-C provide example visual augmentation of the user's perceptions. Further visual augmentation examples are described in U.S. patent application Ser. No. 15/940,704, titled USE OF LASER LIGHT AND RED-GREEN-BLUE COLORATION TO DETERMINE PROPERTIES OF BACK SCATTERED LIGHT, which was filed on Mar. 29, 2018, which is herein incorporated by reference in its entirety.

The augmentation of the user's perceptions could be audible, for example. An audible overlay may be provided via an ear bud set with pass through noise capabilities and/or via a bone conduction speaker system.

The surgical hub may adjust the visual, audible and/or other types of user perception augmentation based on its situational awareness capabilities as described herein. AR content may be adjusted based on a detected surgical progression, for example. AR content may be adjusted based on the activities the user is conducting, voice command, hand gestures, and/or in a predefined manner. AR devices may be instructed to operate by the user in a manner customizable in advance.

AR content may include pre-surgical imaging, intraoperative imaging, instrument data, or procedural instructions. Intraoperative imaging may be obtained via indocyanine green (ICG) fluorescence imaging. AR content may include real time surgical data received from another connected system. AR content may include steps-for-use, device settings, device instruction for use, device status, operational parameters, irregularities detected, or some combination of data derived from the instrument operation.

Figure 43:
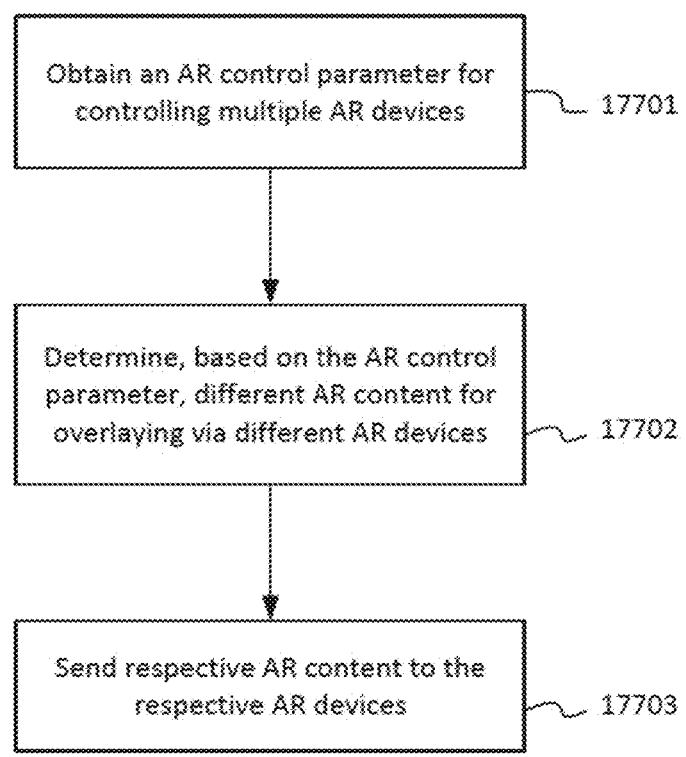
FIG. 43 shows an example flow of a hub operating under a visualization control mode that support AR capabilities.

FIG. 43 shows an example flow of a hub operation under a visualization control mode with AR capabilities. The hub may obtain an AR control parameter for controlling multiple AR devices, at 17701. The AR control parameter for controlling multiple AR devices may include user role(s), a user's orientation relative to a display, a progression of the surgical procedure, a surgical context, a real-time user input, and/or a preconfigured user preference.

At 17702, the hub may then determine, based on the AR control parameter, different AR contents for overlaying via different AR devices. Based on the determined AR contents for different AR devices, the hub may send respective AR contents to the respective AR devices, at 17703.

The AR content may include a step for use associated with a surgical instrument, a device setting, a device status, a device instruction for use, at least one operation parameter, or an indication of a detected abnormality.

The AR control parameter may be a user's orientation relative to a display, and different AR contents for overlaying via different AR devices may be determined based on the user's orientation relative to the display. FIG. 46 shows an example flow of a hub operation under a visualization control mode with AR capabilities that allow overlays on various displays. The hub may obtain an AR control parameter, at 17730. The hub may determine, based on the AR control parameter, overlay data for overlaying on a display via an AR device, at 17731. The hub may detect a user of the AR device viewing the display, at 17732. The hub may overlay, via the AR device, the overlay data onto the content displayed on the display, at 17733. For example, upon determining that a user is viewing a display, the hub may generate and overlay AR contents associated with that display (e.g., the AR content associated with the content displayed on the display). Upon determining that a user is not viewing the display, the hub may remove the AR content associated with the display from the AR device.

In examples, the AR control parameter may be the user role(s) associated with the AR device(s). Different AR contents for overlaying via different AR devices may be generated based on the user role(s) associated with each AR device.

FIG. 45 shows an example flow of a hub operation under a visualization control mode with role-based AR capabilities. The hub may identify a first user role associated with the first AR device, at 17721. The hub may determine, based on the first user role, a first overlay data set for the first AR content, at 17722. The hub may then identify a second user role associated with the first AR device, at 17723. The hub may determine, based on the second user role, a second overlay data set for the second AR content, at 17724.

For example, the surgical hub may identify a user role associated with the AR device and the display type associated with the display. The surgical hub may determine, based on a display type and the user role, the AR content for overlaying on content displayed on the display via the AR device. The display type may be an instrument display located on a smart surgical instrument, a shared display in a surgical suite, or a personal display. The AR content may be adjusted based on the display type of the display onto which the AR content may be superimposed. For example, when the display is a shared display with a larger screen, the AR content may be sized up to fit the image on the shared display. When the display is a surgical device display, AR content may be sized down to accommodate the smaller screen. For example, when the display is a surgical device display, surgical information that may not fit into the surgical device display may be added to the AR content to make such information available to the user.

Figure 21:
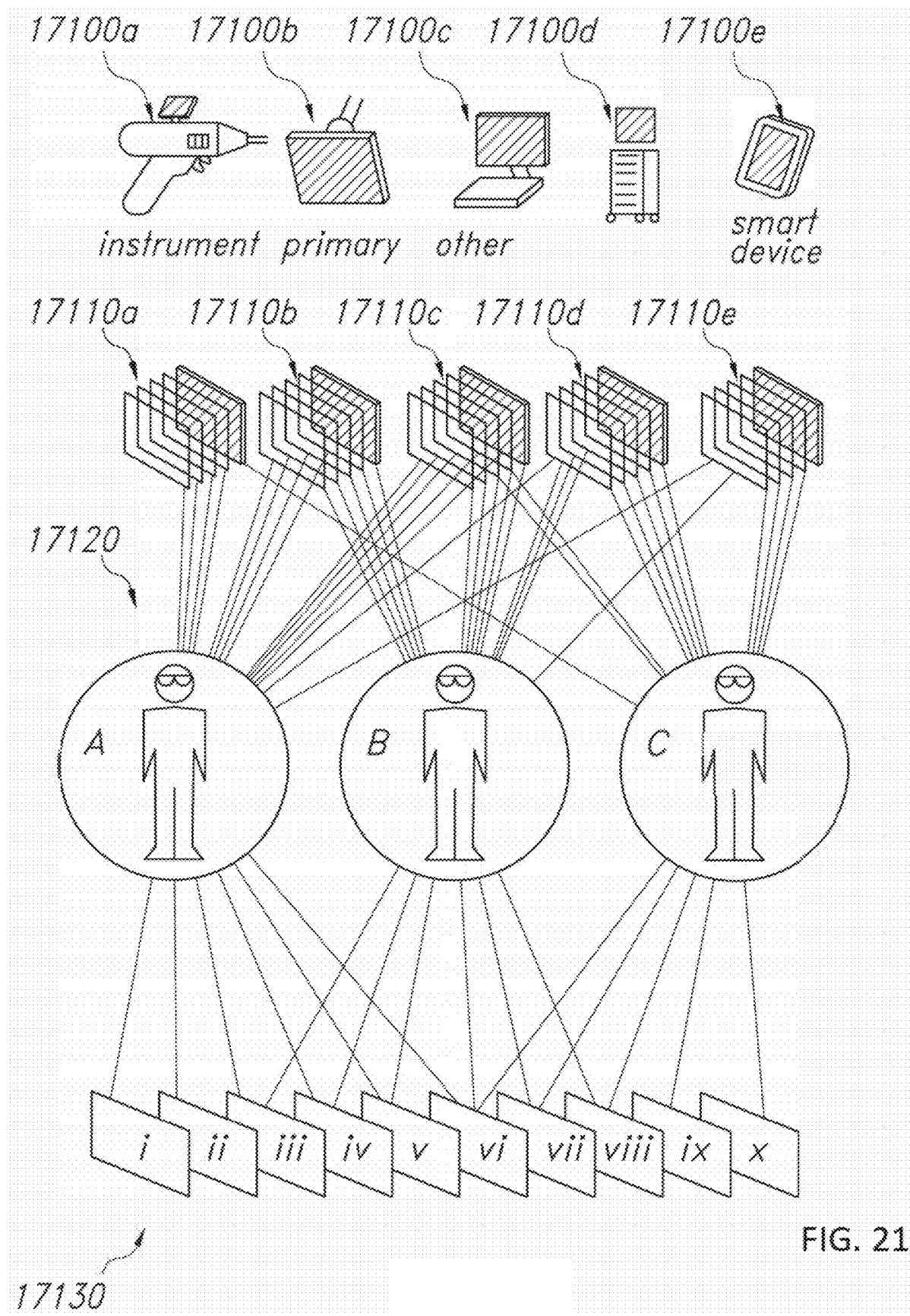
FIG. 21 illustrates example role-based interaction and control related to augmented reality and deviceless control system.

FIG. 21 illustrates an augmented reality system that can be controlled by multiple users. As shown, the system may include various OR displays 17100, including an instrument 17100(a), a primary display 17100(b), other displays 17100(c), a surgical hub 17104 and a smart device 17100(d). The hub 17104 and the AR devices worn by users 17120(A), (B) and (C) can superimpose a predefined set of overlay data layers 17110(a)-(e) on various OR displays 17100(a)-(e). Healthcare professional users 17120(A), (B) and (C) may each wear an augmented reality device, such as safety glasses with an AR display, AR goggles, or HMDs as described herein. The surgical hub and/or the AR device(s) can control access to certain displays and the overlay data layers.

AR content displayed on an AR device may be generated based on its user's role, situation awareness-related data, and/or the visualization control mode (such as subscription tier). As shown, user 17120(A)'s AR device may receive overlays 17110(a)-(e) based on 17120(A)'s user role, the operation situation and/or the tier level of the system, while user 17120(B)'s AR device may only receive overlays 17110(b)-(e). A subset of overlay data layers that user 17120(A)'s AR device and user 17120(B)'s AR device receive may be the same, while some of the overlay data layers received at the devices may be different, as shown in FIG. 21. Example interactive set of overlay data layers 17130 may include pre-surgical imaging, intraoperative imaging, instrument data, procedural information and/or data generated based on the aforementioned. As an example, user 17120(A), (B) and (C) may access to different set of overlays based on their different roles and different procedures of the situation.

Figure 44:
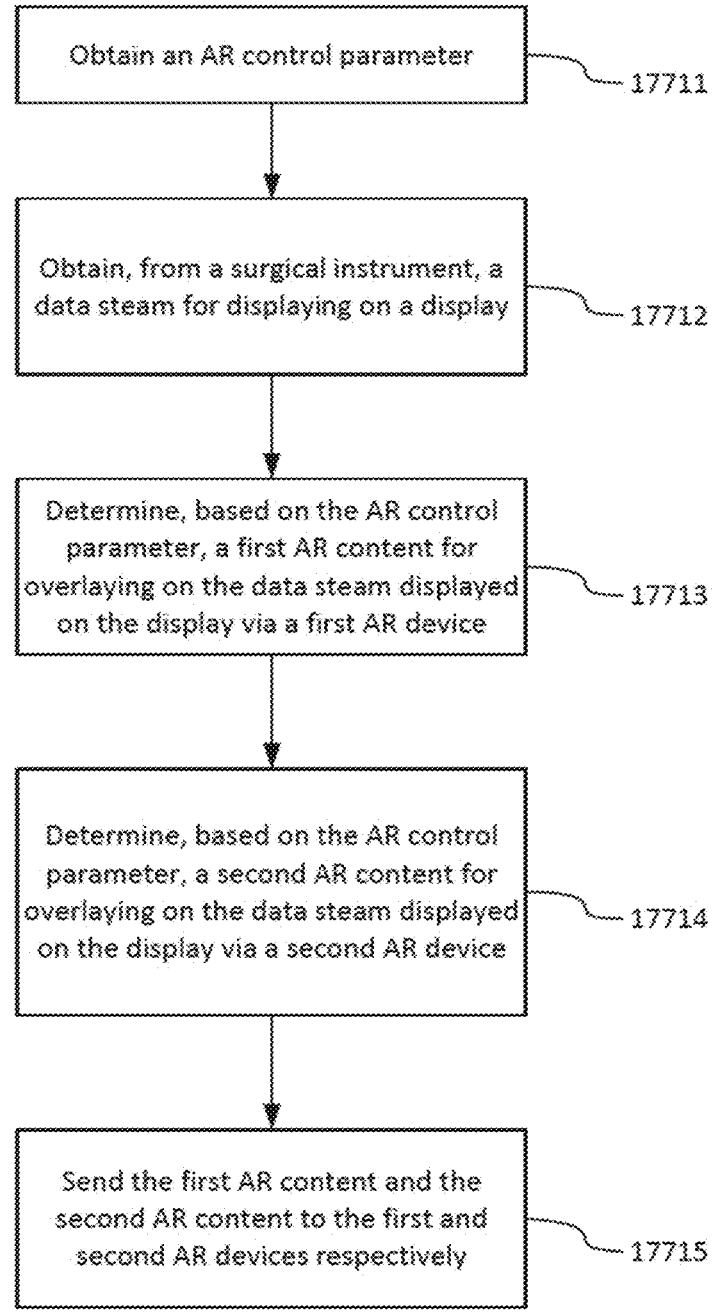
FIG. 44 shows an example flow of a hub operating on under a visualization control mode that support AR capabilities.

FIG. 44 shows an example flow of a hub operation under a visualization control with AR capabilities. At 17711, the hub may obtain an AR control parameter as described herein. At 17712, the hub may obtain, from a surgical instrument, a data stream for displaying on a display. The data stream may be or may include video image of a surgical site within a patient. The hub, at 17713, may determine, based on the AR control parameter, a first AR content for overlaying on the data stream displayed on the display via a first AR device. The first AR content may include a step for use a surgical instrument, a device setting, a device status, a device instruction for use, at least one operation parameter, or an indication of a detected abnormality. The hub, at 17714, may determine, based on the AR control parameter, a second AR content for overlaying on the data stream displayed on the display via a second AR device. At 17715, the hub, based on the determined AR contents for the respective AR devices for display, may send the AR contents to the respective AR devices.

In an example visualization control mode that supports augmented reality content, the surgical hub may overlay surgical information onto an anatomical structure model on a display. For example, based on a determination that the user associated with the AR device is a surgeon, the surgical hub may send AR content that includes visualization of the tumor, the tumor margin and possible emphysema to the AR device. For example, based on a determination that the user associated with the AR device is a surgeon's assistant, the surgical hub may send AR content that includes the step surgical step that requires assistance, a device setting and/or a device status.

Figure 28:
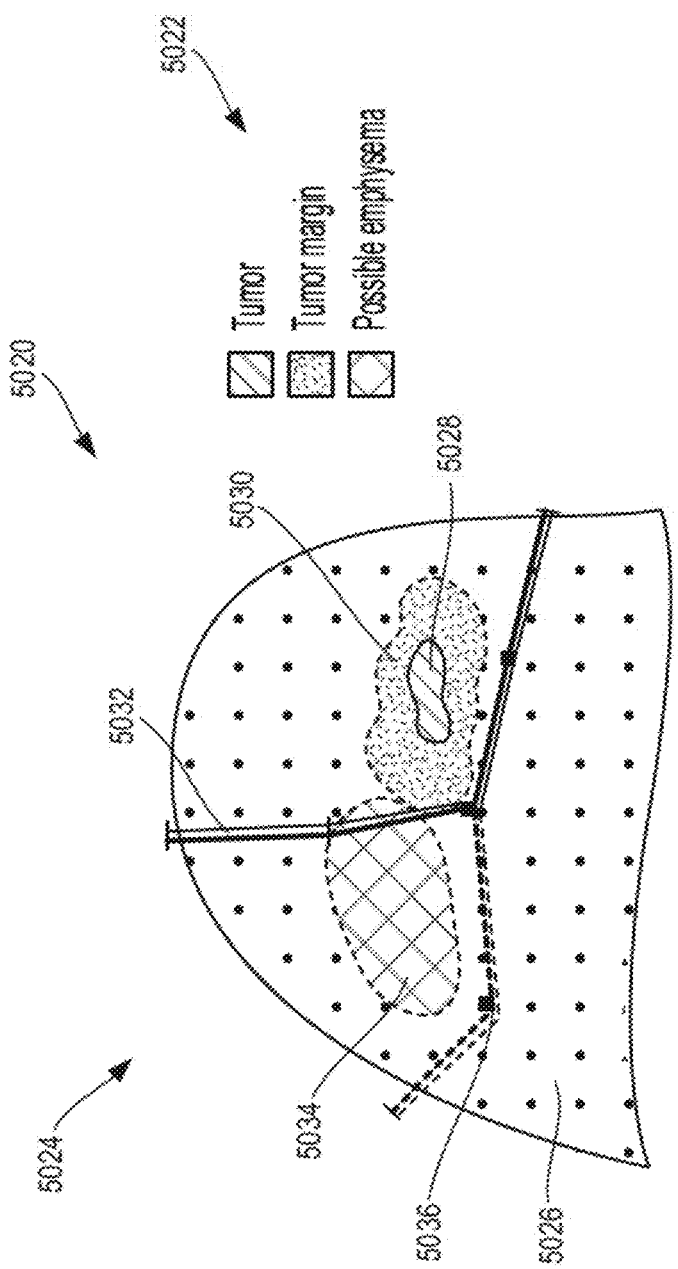
FIG. 28 shows an example display of a surgical visualization system shown in accordance with at least one aspect of the present disclosure.

FIG. 28 shows an example display 5020 that may be viewed from an AR device. Display 2020 includes screen content displayed on a screen overlaid with AR content. Display 5020 can depict an information index 5022 and a model of an anatomical structure 5024 generated by a control system of the surgical visualization system. The anatomical structure 5024 may include unaffected tissue 5026 that is neither diseased, nor occupied by a critical structure. The model of the anatomical structure 5024 can depict detected and/or determined features, such as a subject tissue 5028, a predetermined margin 5030, a resection margin 5032, a first characteristic 5034 of the anatomical structure 5024, and an adjusted resection margin 5036. The control system 133 of the surgical visualization system has designated each of these detected features of the anatomical structure 5024 a specific color, and the display 5020 can depict each of the detected features in its specifically designated color, as is represented via the cross-hatching of FIG. 28. The information index 5022 can depict a correlation of each specific color with information that is relevant to its designated detected feature. For example, the information index 5022 of FIG. 28 correlates each specific color with a textual description of a corresponding feature of the anatomical structure 5024. In other aspects, the information index 5022 correlates each specific color with additional information that is relevant to a corresponding feature.

As depicted in FIG. 28, the surgical visualization system can detect a subject tissue 5028 within the anatomical structure 5024. The information index 5022 of the display 5020 can indicate that the detected subject tissue 5028 is a tumor. An instruction stored in the memory of a control system of the surgical visualization system can instruct the control circuit to apply a predetermined margin 5030 around the subject tissue 5028 based on detected qualities of the tumor, including its size, geometry, and/or type. Accordingly, the control system 133 can designate the resection margin 5030 a specific color, and the information index 5022 can correlate the specific color with additional information associated with the resection margin 5030. The control circuit of the surgical visualization system can determine a resection margin 5032 around the subject tissue 5028, in consideration of the detected subject tissue 5028 and predetermined margin 5030. In the display 5020 of FIG. 28, the resection margin 5032 is depicted in linear segments about the anatomical structure 5024, corresponding to the capabilities of an intended surgical instrument. For example, the surgical instrument can be a surgical stapler configured to staple tissue before cutting it via a linear stroke. However, the display 5020 can alternately depict the resection margin 5032 if other surgical instruments are implemented.

The display 5020 of FIG. 28 depicts a characteristic 5034 of the anatomical structure 5024 detected by the surgical visualization system. The information index 5022 of the display 5020 of FIG. 28 can indicate that the detected characteristic 5034 of the anatomical structure 5024 is tissue 5026 that has been damaged by emphysema. The AR content may include the initially determined resection margin 5032 of FIG. 28, which can traverse through the characteristic 5034 of the anatomical structure 5024. The control circuit of the surgical visualization system can determine an adjusted resection margin 5036 to encompasses the characteristic 5036, the subject tissue 5028, and the predetermined margin 5030. The AR content may include the adjusted resection margin 5036 via dashed lines. Such AR content may allow the operating clinician(s) to select either the initially determined resection margin 5032, or the adjusted resection margin 5036. In other aspects, the display 5020 will limit the operating clinician(s) to the adjusted resection margin 5036 based on an instruction stored in the memory of the control system.

Figure 29:
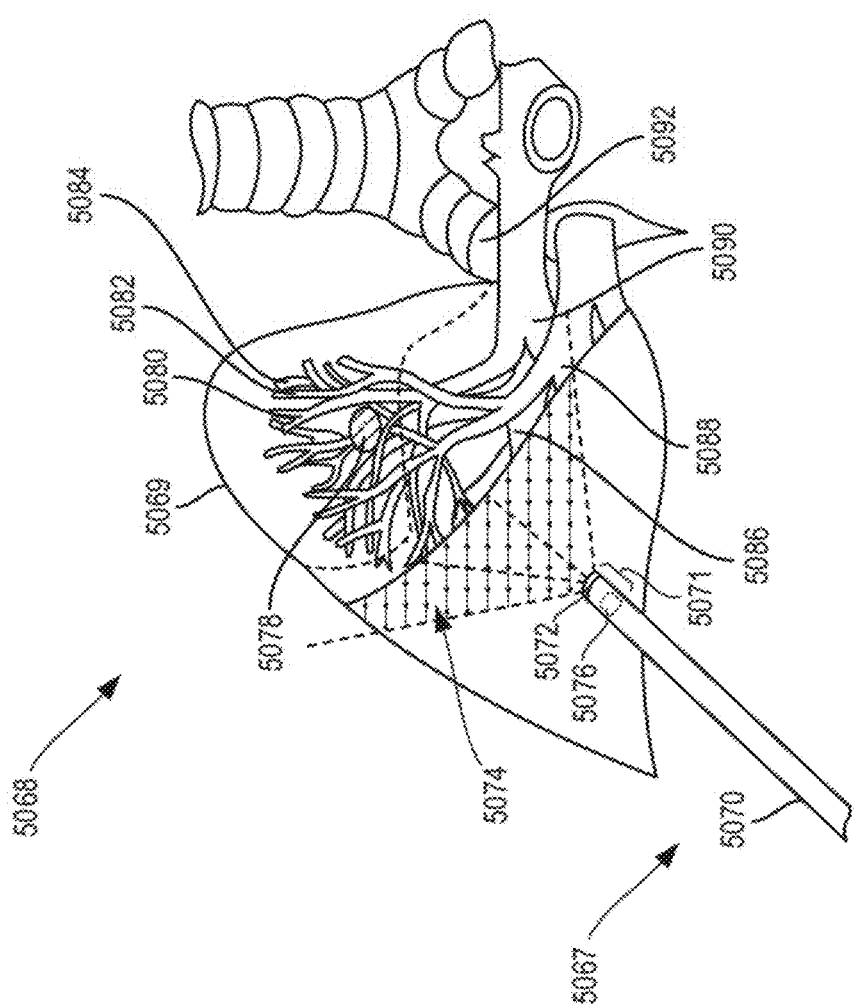
FIG. 29 shows an example model of an anatomical structure generated by an example surgical visualization system.

For example, AR content may be generated for surgical planning and/or critical structure detection, etc. Referring now to FIG. 29, a three-dimensional model 5068 of an anatomical structure 5069 generated by a surgical visualization system is depicted. The surgical visualization system can include an imaging device 5070 with a distance sensor system 5071 having an emitter 5072 configured to emit electromagnetic radiation 5074 onto the anatomical structure 5069, and a receiver 5076 configured to detect reflected electromagnetic radiation 5074. The imaging device 5070 of FIG. 29 can utilize the aforementioned spectral light, structured light, and Laser Doppler techniques to identify critical structures, such as a tumor 5078, and generate a fully integrated model 5068 and detailed characterization of the anatomical structure 5069. For example, the three-dimensional model 5068 of FIG. 25 can depict the anatomical structure 5069 as the superior lobe of a right lung, and can depict various characteristics of the anatomical structure 5069 with specificity, such as an artery 5080, a vein 5082, a bronchus 5084, a superior lobar bronchus 5086, a right pulmonary artery 5090, and/or a main bronchus 5092. Although the anatomical structure 5069 of FIG. 29 is a lung, the surgical visualization system can model various anatomical structures depending on the intended implementation. Accordingly, the surgical visualization system can use spectral light, structured light, and/or Laser Doppler to characterize any anatomical structure and display detected characteristics in detail via a three-dimensional model.

AR content may include a proximity alert when the distal tip of a surgical instrument moves within a certain range of the critical structure 5078. For example, real-time, three-dimensional spatial tracking of the distal tip of a surgical instrument may be performed. The distance sensor system 5071 of the imaging device 5070 can be positioned on the distal tip of a surgical instrument. Accordingly, the emitter 5072 can emit electromagnetic radiation 5074 onto the surface of the anatomical structure 5069 and the receiver 5076 can detect electromagnetic radiation 5074 that has reflected off the surface of the anatomical structure 5069. The surgical visualization system can determine a position of the emitter 5072 relative to the surface of the anatomical structure 5069 based on a time-of-flight of the electromagnetic radiation 5074, or the time between its emission from the emitter 5072 and its detection by the receiver 5076. Although the surgical visualization system may use a distance sensor system 5071 and time-of-flight technique to determine the position of a surgical instrument relative to the anatomical structure 5069, other suitable components and/or techniques can be employed to achieve the same effect and include the position of a surgical instrument in the three-dimensional model 5068 of the anatomical structure 5069.

In examples, the AR control parameter may be a progression of the surgical procedure, and different AR contents for overlaying via different AR devices may be determined based on the progression of the surgical procedure. For example, based the surgical progression approaches a transection, the AR content provided to the AR device associated with a surgeon may include a proposed transection path. The AR content provided to another AR device may include a notification that the surgery is reaching an important step.

Figure 30:
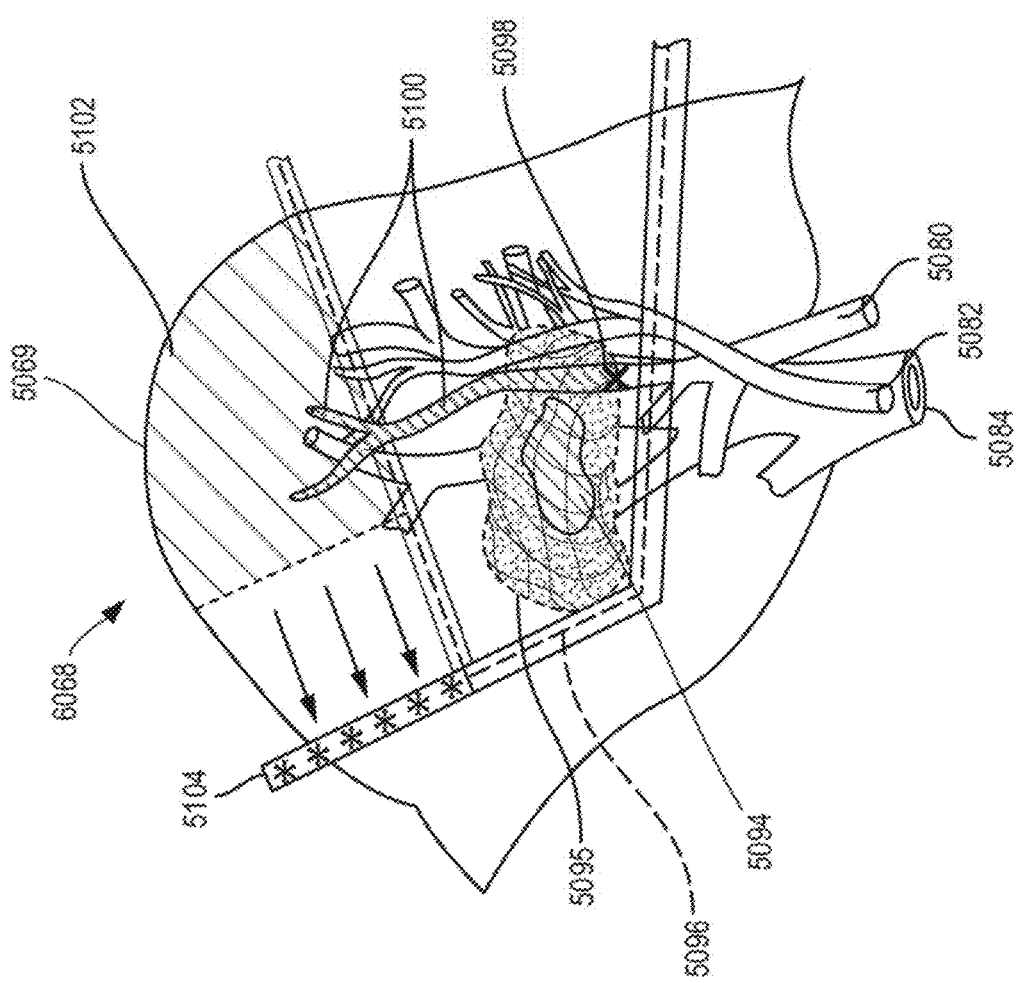
FIG. 30 shows an example display of an example model in accordance with at least one aspect of the present disclosure.

Referring to FIG. 30, a display of the three-dimensional model 5068 of FIG. 29 is depicted in accordance with at least one aspect of the present disclosure. The AR content may include a resection margin overlay configured to depict user selected transection path 5096 and a system proposed transection path 5104. For example, the resection margin overlay can further depict detected characteristics such as the artery 5080, vein 5082, and bronchus 5084, detected subject tissues such as a tumor 5094, and/or a predetermined margin 5095 based on an instruction stored in the memory 134 (FIG. 2). Having reviewed the AR content superimposed or overlaid on the surgical display, the operating clinician(s) can determine a user selected transection path 5096 to remove the tumor 5094 and predetermined margin 5095. For example, the operating clinician(s) can determine a user selected transection path 5096 that can optimize the residual volume of the anatomical structure 5069, such as lung volume. Accordingly, the operating clinician(s) can provide the user selected transection path 5096 to the surgical visualization system via a user interface.

The surgical visualization system can receive the user selected transection path 5096 via user interface and assess the user selected transection path 5096 relative to the position of any detected characteristics of the anatomical structure 5069. For example, as depicted in FIG. 30, the surgical visualization system can identify that the user selected transection path 5096 interferes with an artery 5080, vein 5082, and bronchus 5084 of the anatomical structure 5069. Accordingly, the combined view 5093 (e.g., surgical display superimposed with AR content) can depict the anticipated interference and issue a notification to the operating clinician(s). The notification can be visual, audible, haptic, and/or any combination thereof. The display can additionally highlight a characteristic or a portion of the anatomical structure 5069 affected by the user selected transection path 5096 and/or a portion of the anatomical structure 5069 that can be rendered non-viable by the user selected transection path 5096. For example, the AR content can highlight a transected portion 5098 of the artery 5080 to represent a blood supply 5100 that would be affected by the user selected transection path 5096. The AR content may highlight a portion 5102 of the anatomical structure 5069 that can be rendered non-viable by the user selected transection path 5096 dude to a lack of blood or air.

Additionally and/or alternatively, the AR content may include a system proposed transection path 5104 that may optimize the residual volume of the anatomical structure 5069, remove the subject tissue 5094 and predetermined margin 5095, and minimize adverse impacts to the detected characteristics of the anatomical structure 5069. For example, although the system proposed transection path 5104 may preserve less residual volume of the anatomical structure 5069, it may not interfere with the artery 5080, vein 5082, and bronchus 5084 and may still remove the tumor 5094 and predetermined margin 5095 from the superior lobe of the lung. In some aspects, the surgical visualization system can allow the operating clinician(s) to choose either the user selected transection path 5096 or the system proposed transection path 5104. In other aspects, the surgical visualization system can allow the operating clinician(s) to decline the system proposed transection path 5104 and input a second user selected transection path based on the depicted information on the display.

Figure 31:
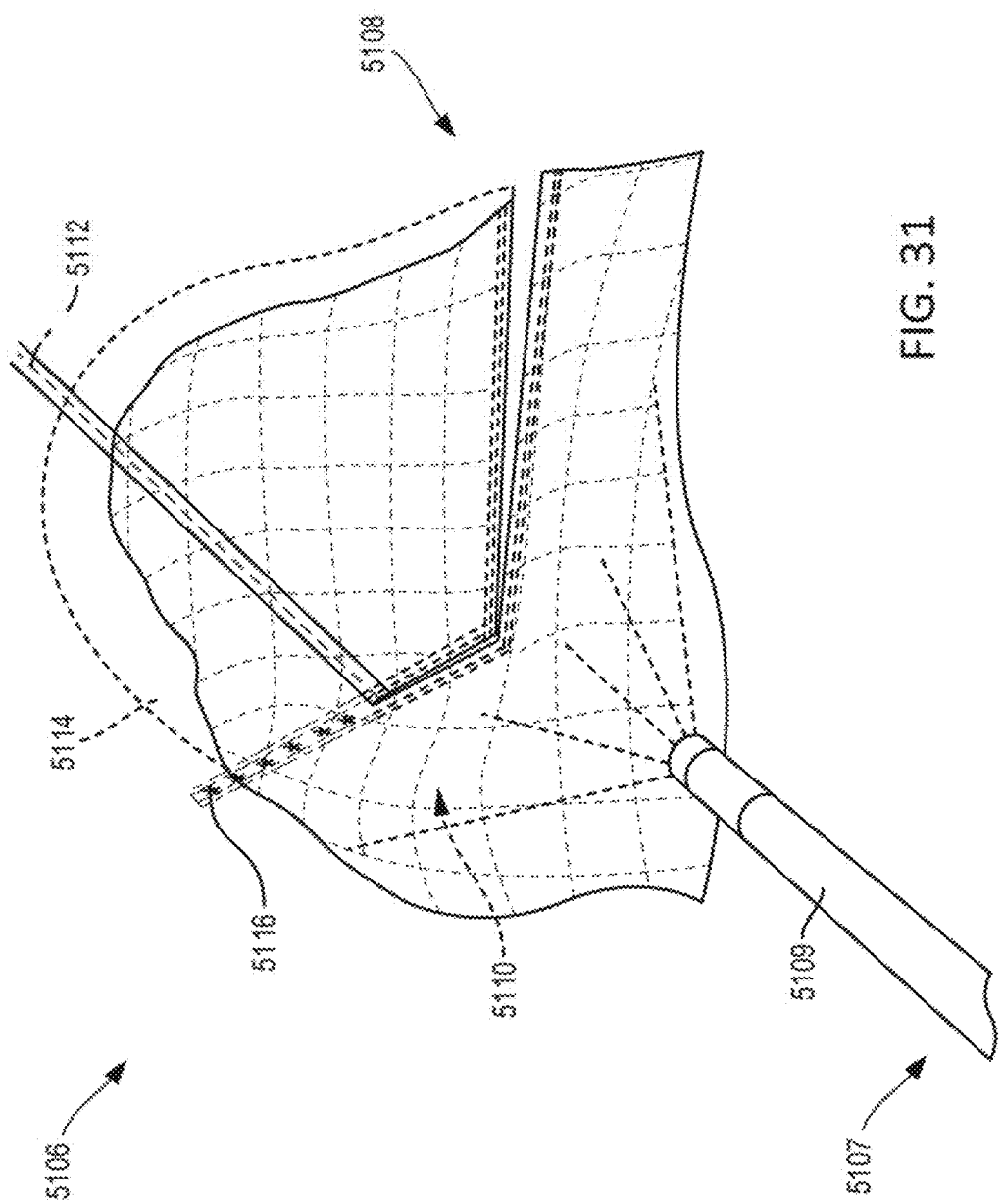
FIG. 31 shows an example display of an example model of an anatomical structure generated by an example surgical visualization system.

Referring now to FIG. 31, an AR content combined with display view 5106 three-dimensional model 5108 of an anatomical structure 5110 generated by a surgical visualization system 5107 is depicted in accordance with at least one aspect of the present disclosure. The surgical visualization system 5107 can include a surgical instrument 5109 with a distance sensor system, a structured light system, a spectral light system, or any combination thereof. Having reviewed the display 5106, the operating clinician(s) can determine a user selected transection path 5112 to remove a subject tissue from the anatomical structure 5110. The surgical visualization system 5107 of FIG. 31 can receive the user selected transection path 5112 via user interface and assess the user selected transection path 5112 relative to the position of any detected characteristics of the anatomical structure 5110. For example, the surgical visualization system 5107 of FIG. 31 has identified that the user selected transection path 5112 can interfere with a portion 5114 of the anatomical structure 5110 that is underinflated. The underinflated portion 5114 of the anatomical structure 5110 can have an adverse effect on the excision of a subject tissue and can lead to post-operative complications, including a less than optimal residual volume of the anatomical structure 5110. Accordingly, the AR content include an indication of the anticipated problem and a notification to the operating clinician(s). The notification can be visual, audible, haptic, and/or any combination thereof.

Additionally and/or alternatively, the AR content shown in FIG. 31 can depict a system proposed transection path 5116 that may be overlaid on the display. The system proposed path may optimize the residual volume of the anatomical structure 5110, remove the subject tissue and predetermined margin, and/or minimize adverse impacts caused by the detected characteristics of the anatomical structure 5110. For example, the transection of underinflated tissue 5114 could complicate the surgical procedure and introduce unnecessary risk. The system proposed transection path 5116 of FIG. 31 directs the operating clinician(s) to the fully inflated tissue of the anatomical structure 5110, thereby minimizes the risk. In some aspects, the surgical visualization system 5107 can allow the operating clinician(s) to choose either the user selected transection path 5112 or the system proposed transection path 5116. In other aspects, the surgical visualization system 5107 can allow the operating clinician(s) to decline the system proposed transection path 5116 and input a second user selected transection path based on the depicted information on the display 5106.

The surgical instrument(s) described herein can be configured with a distance sensor system, or other means to enable the surgical visualization system to detect a position of the surgical instrument relative to the anatomical structure. The surgical visualization systems discussed herein can also issue notifications via the AR device(s), informing the operating clinician(s) if a detected position of the surgical instrument does not comply with the selected transection path. The surgical visualization systems can issue, via the AR device(s), a visual, audible, and/or haptic notification to the operating clinician(s) indicating that the surgical instrument should be repositioned prior to commencing the surgical procedure. In some aspects, the surgical visualization system can, via the AR device(s), prevent the operating clinician(s) from performing the surgical procedure until the surgical instrument is properly positioned in accordance with the selected transection path depicted on the display.

Display of automatically adjustable tumor margins based on visually identified key structures, anomalies, and instrument sensed tissue properties is further described in U.S. patent application Ser. No. 16/729,778 titled SYSTEM AND METHOD FOR DETERMINING, ADJUSTING, AND MANAGING RESECTION MARGIN ABOUT A SUBJECT TISSUE, filed Dec. 31, 2019, which is incorporated by reference herein in its entirety.

In examples, the AR content may include visualization of obstructed portions of a surgical site. The visualization of the obstructed portions of the surgical site may be overlaid on the livestream of a surgical site in the surgical operating room from the medical imaging device. The visualization of the obstructed portions of the surgical site may be generated using a multispectral EMR source.

Figure 32:
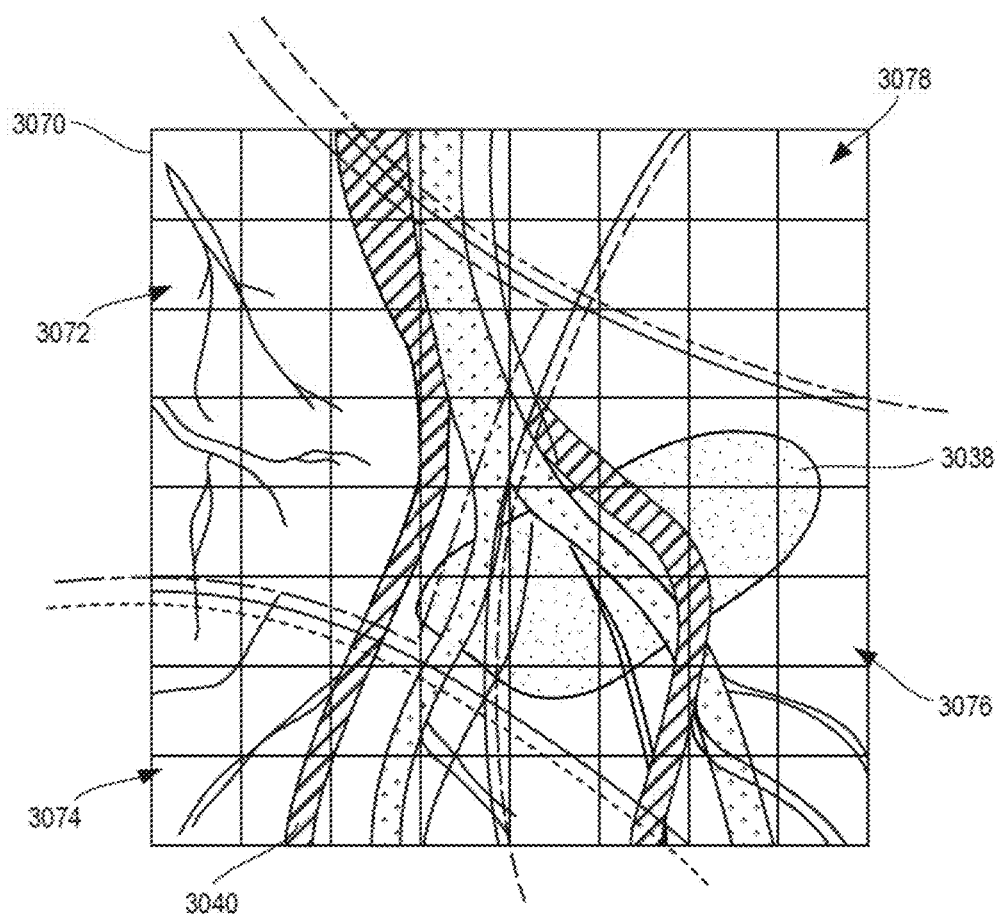
FIG. 32 is a diagram of an example fused image generated from a multispectral EMR source.

FIG. 32 shows an example fused image generated from a multispectral EMR source. The fused image may be generated using image data from at least three different EMR wavelength ranges to generate the resulting image. Multiple images may be used to collectively visualize the surgical site at the corresponding EMR wavelength range. For example, a first image may be captured utilizing the visible light portion of the EMR spectrum and includes a first unobstructed portion, with the remaining portions of the image being obstructed; the second image may be captured utilizing the MWIR portion of the EMR spectrum and includes a second unobstructed portion; and a third image 3042c may be captured utilizing the LWIR portion of the EMR spectrum and includes a third unobstructed portion. For example, a fourth image may be captured utilizing the visible light portion of the EMR spectrum and thus can correspond to the first image, but may include additional image processing to identify a fluid (water) obstructed portion. Accordingly, the corresponding portion of the first image could be filtered at a corresponding wavelength or wavelength range (e.g., the blue-green portion of the visible light spectrum) to remove the obstruction.

A combination or fused image 3070 may be generated from the aforementioned initial images. The fused image 3070 can include a first portion 3072 corresponding to the unobstructed portion of the first image generated from the visible light portion of the EMR spectrum, a second portion 3074 corresponding to the unobstructed portion of the second image generated from the MWIR portion of the EMR spectrum, a third portion 3076 corresponding to the unobstructed portion of the third image generated from the LWIR portion of the EMR spectrum, and a fourth portion 3078 corresponding to the obstructed portion of an image generated from the visible light portion of the EMR spectrum, but post-processed to remove the blue-green portion of the visible light spectrum. Each of the aforementioned image portions 3072, 3074, 3076, 3078 can be fused together to generate the fused image 3070 that provides for an unobstructed visualization of the tumor 3038 and any other relevant structures 3040.

Utilization of fusion imagery is described in detail in U.S. patent application Ser. No. 16/729,807 titled METHOD OF USING IMAGING DEVICES IN SURGERY, filed Dec. 31, 2019, which is incorporated by reference herein in its entirety.

Figure 34A:
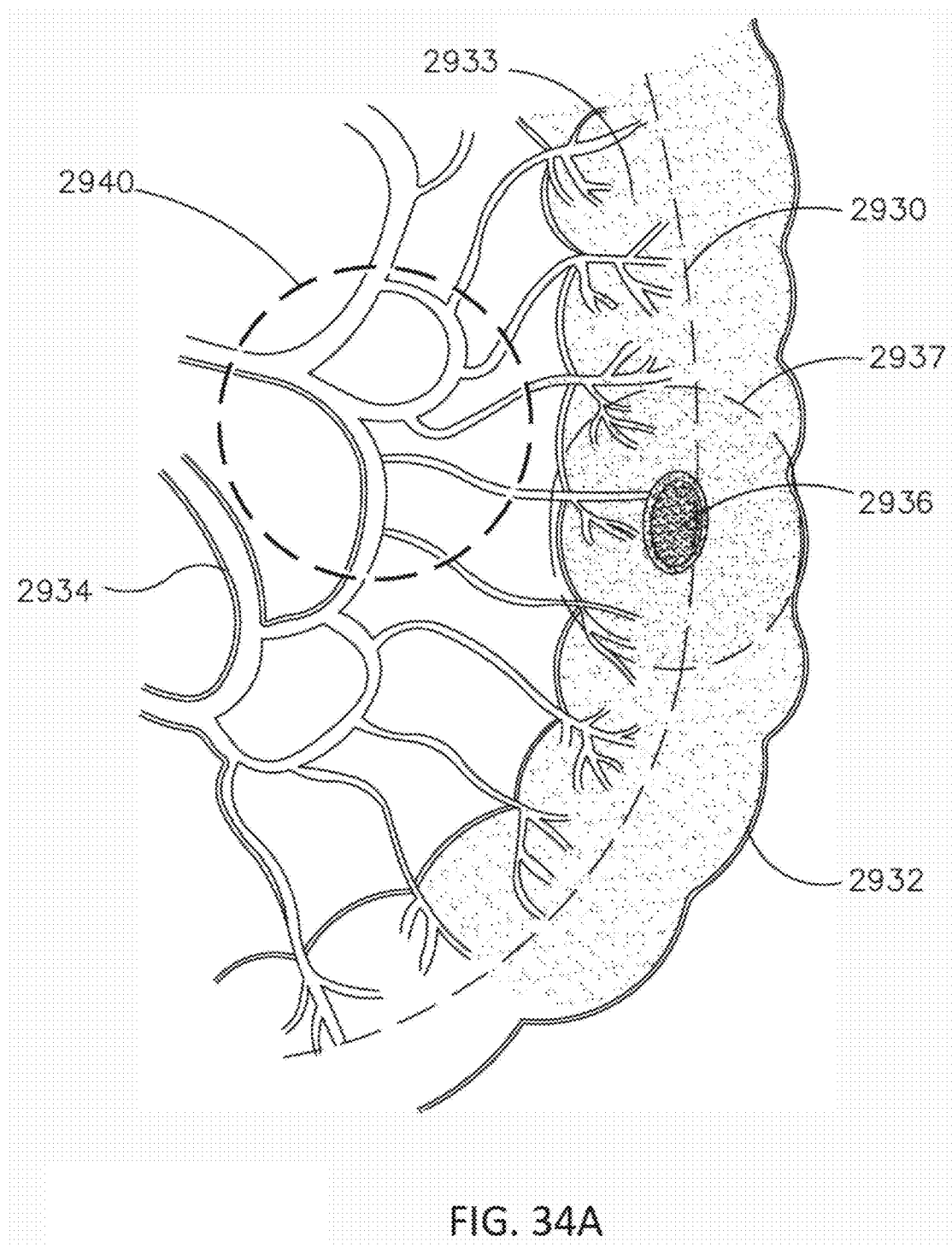
FIG. 34A-C illustrate examples of a sequence of surgical steps with multi-image analysis at the surgical site.
Figure 34B:
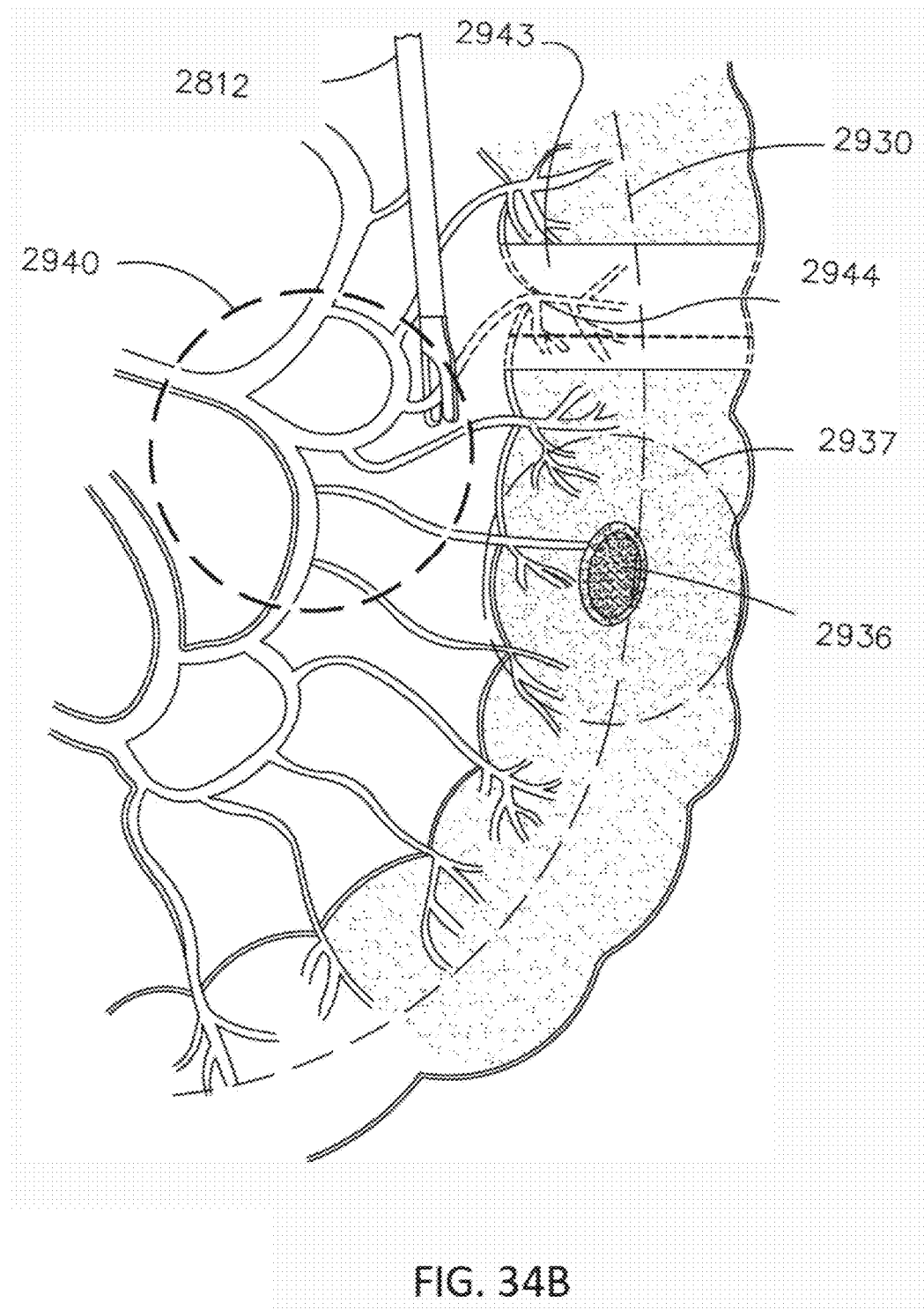
Figure 34C:
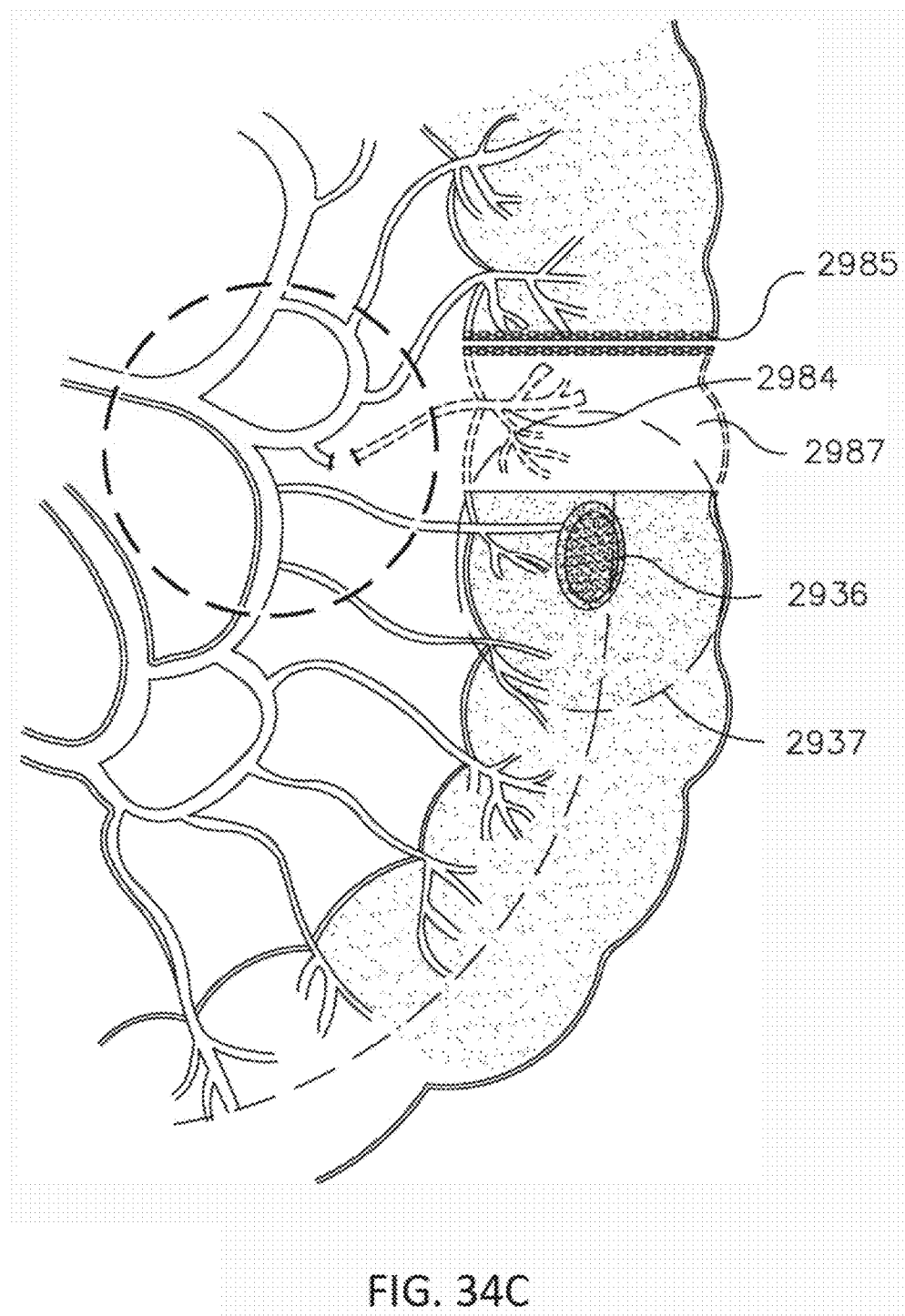

FIGS. 34A-C illustrate examples of a sequence of surgical steps for the removal of an intestinal/colon tumor and which may benefit from the AR content generated using multi-image analysis at the surgical site. FIG. 34A depicts a portion of the surgical site, including the intestines 2932 and the ramified vasculature 2934 supplying blood and nutrients to the intestines 2932. The intestines 2932 may have a tumor 2936 surrounded by a tumor margin 2937. A first light sensor module of a visualization system may have a wide field of view 2930, and it may provide imaging data of the wide field of view 2930 to a display system. A second light sensor module of the visualization system may have a narrow or standard field of view 2940, and it may provide imaging data of the narrow field of view 2940 to the display system. In some aspects, the wide field image and the narrow field image may be displayed by the same display device. In another aspect, the wide field image and the narrow field image may be displayed by separate display devices.

During the surgical procedure, it may be important to remove not just the tumor 2936 but the margin 2937 surrounding it to assure complete removal of the tumor. A wide-angle field of view 2930 may be used to image both the vasculature 2934 as well as the section of the intestines 2932 surrounding the tumor 2936 and the margin 2637. As noted above, the vasculature feeding the tumor 2936 and the margin 2637 should be removed, but the vasculature feeding the surrounding intestinal tissue must be preserved to provide oxygen and nutrients to the surrounding tissue. Transection of the vasculature feeding the surrounding colon tissue will remove oxygen and nutrients from the tissue, leading to necrosis. In some examples, laser Doppler imaging of the tissue visualized in the wide-angle field 2630 may be analyzed to provide a speckle contrast analysis 2933, indicating the blood flow within the intestinal tissue.

The AR content may include an indication of blood flow within a tissue. For example, the AR content may include an indication of which part of the vascular tree may supply blood to a tumor. FIG. 34B illustrates a step during the surgical procedure. The surgeon may be uncertain which part of the vascular tree supplies blood to the tumor 2936. The surgeon may test a blood vessel 2944 to determine if it feeds the tumor 2936 or the healthy tissue. The surgeon may clamp a blood vessel 2944 with a clamping device 2812 and determine the section of the intestinal tissue 2943 that is no longer perfused by means of the speckle contrast analysis. The narrow field of view 2940 displayed on an imaging device may assist the surgeon in the close-up and detailed work required to visualize the single blood vessel 2944 to be tested. When the suspected blood vessel 2944 is clamped, a portion of the intestinal tissue 2943 is determined to lack perfusion based on the Doppler imaging speckle contrast analysis. The suspected blood vessel 2944 does not supply blood to the tumor 2935 or the tumor margin 2937, and therefore is recognized as a blood vessel to be spared during the surgical procedure.

FIG. 34C depicts a following stage of the surgical procedure. In stage, a supply blood vessel 2984 has been identified to supply blood to the margin 2937 of the tumor. When this supply blood vessel 2984 has been severed, blood is no longer supplied to a section of the intestine 2987 that may include at least a portion of the margin 2937 of the tumor 2936. In some aspects, the lack of perfusion to the section 2987 of the intestines may be determined by means of a speckle contrast analysis based on a Doppler analysis of blood flow into the intestines. The non-perfused section 2987 of the intestines may then be isolated by a seal 2985 applied to the intestine. In this manner, only those blood vessels perfusing the tissue indicated for surgical removal may be identified and scaled, thereby sparing healthy tissue from unintended surgical consequences.

The AR content may be generated based on imaging analysis of the surgical site. The surgical site may be inspected for the effectiveness of surgical manipulation of a tissue. Non-limiting examples of such inspection may include the inspection of surgical staples or welds used to seal tissue at a surgical site. Cone beam coherent tomography using one or more illumination sources may be used for such methods. The AR content may include landmarks denoted in an image of a surgical site. In some examples, the landmarks may be determined through image analysis techniques. In some examples, the landmarks may be denoted through a manual intervention of the image by the surgeon. In some aspects, non-smart ready visualizations methods may be imported for used in hub image fusion techniques.

The instruments that are not integrated in the hub system may be identified and tracked during their use within the surgical site. In this aspect, computational and/or storage components of the hub or in any of its components (including, for example, in the cloud system) may include a database of images related to EES and competitive surgical instruments that are identifiable from one or more images acquired through any image acquisition system or through visual analytics of such alternative instruments. The imaging analysis of such devices may further permit identification of when an instrument is replaced with a different instrument to do the same or a similar job. The identification of the replacement of an instrument during a surgical procedure may provide information related to when an instrument is not doing the job or a failure of the device.

In examples, AR content may include anatomical identification information that may be generated based on pre-operative image(s). The AR content may be overlaid on a video image of a surgical site within the patient. The anatomical identification information may be overlaid on the livestream of a surgical site in the surgical operating room from the medical imaging device.

Figure 35:
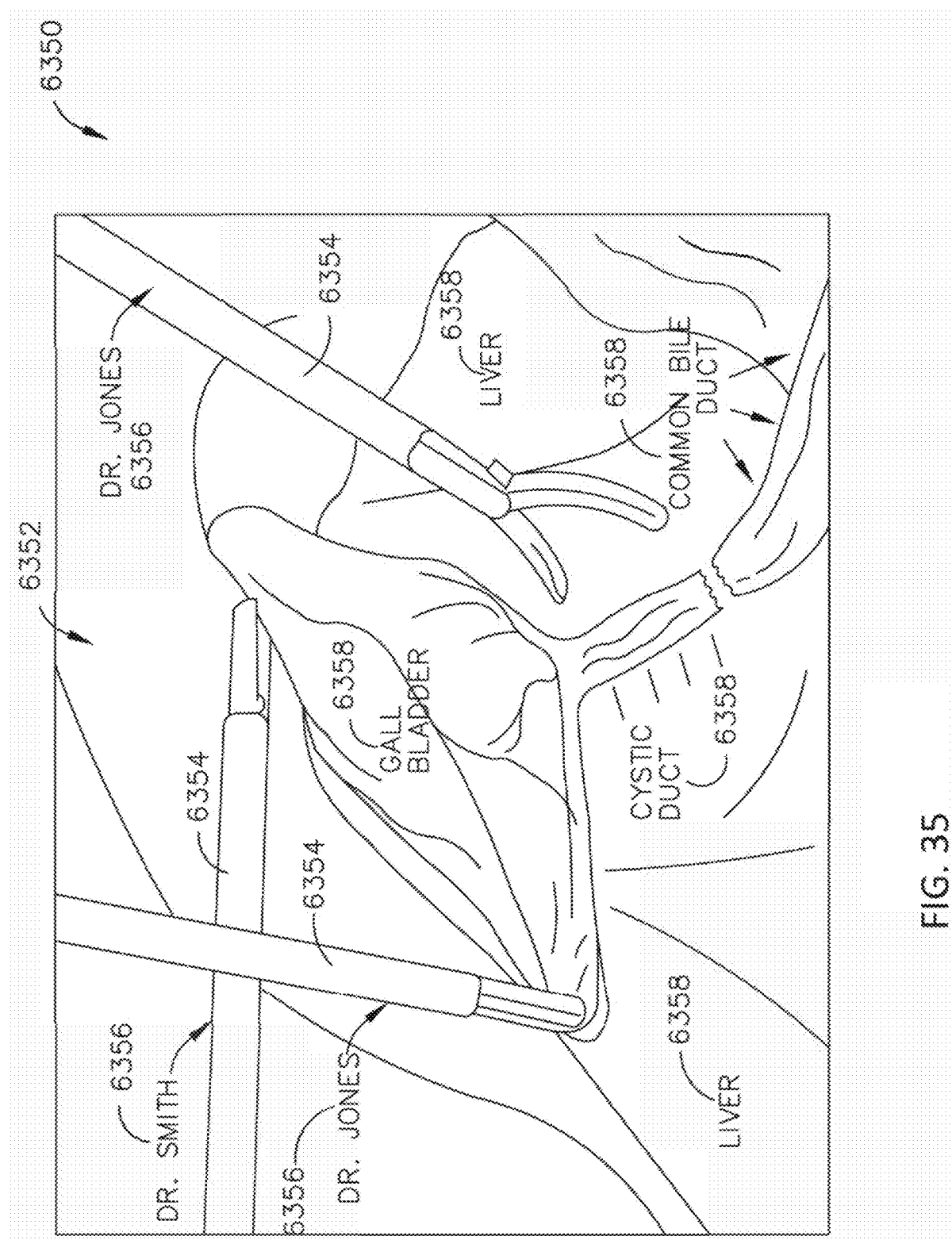
FIG. 35 illustrates an example of an augmented video image of a pre-operative video image augmented with data identifying displayed elements.

FIG. 35 illustrates an example of an augmented video image 6350 comprising a pre-operative video image 6352 augmented with data 6354, 6356, 6358 identifying displayed elements. AR data may be overlaid or superimposed onto a pre-operative image 6352 via an AR device. A pre-operative image 6352 of an anatomical section of a patient may be generated. An augmented video image of a surgical site within the patient may be generated. The augmented video image 6350 can include an image of at least a portion of a surgical tool 6354 operated by a user 6456. The pre-operative image 6352 may be processed to generate data about the anatomical section of the patient. The AR content can include a label 6358 for the anatomical section and a peripheral margin of at least a portion of the anatomical section. The peripheral margin can be configured to guide a surgeon to a cutting location relative to the anatomical section, embedding the data and an identity of the user 6356 within the pre-operative image 6350 to display an augmented video image 6350 to the user about the anatomical section of the patient. A loading condition on the surgical tool 6354 may be sensed, a feedback signal may be generated based on the sensed loading condition. The AR content, including the data and a location of the identity of the user operating the surgical tool 6354 may be updated in real time, in response to a change in a location of the surgical tool 6354 within the augmented video image 6350. Further examples are disclosed in U.S. Pat. No. 9,123,155, titled APPARATUS AND METHOD FOR USING AUGMENTED REALITY VISION SYSTEM IN SURGICAL PROCEDURES, which issued on Sep. 1, 2015, which is herein incorporated by reference in its entirety.

Radiographic integration techniques may be employed to overlay the pre-operative image 6352 with data obtained through live internal sensing or pre-procedure techniques. Radiographic integration may include marker and landmark identification using surgical landmarks, radiographic markers placed in or outside the patient, identification of radio-opaque staples, clips or other tissue-fixated items. Digital radiography techniques may be employed to generate digital images for overlaying with a pre-operative image 6352. Digital radiography is a form of X-ray imaging that employs a digital image capture device with digital X-ray sensors instead of traditional photo graphic film. Digital radiography techniques provide immediate image preview and availability for overlaying with the pre-operative image 6352. In addition, special image processing techniques can be applied to the digital X-ray mages to enhance the overall display quality of the image.

Digital radiography techniques can employ image detectors that include flat panel detectors (FPDs), which are classified in two main categories indirect FPDs and direct FPDs. Indirect FPDs include amorphous silicon (a-Si) combined with a scintillator in the detector's outer layer, which is made from cesium iodide (CSI) or gadolinium oxy-sulfide (Gd202S), converts X-rays to light. The light can be channeled through the a-Si photodiode layer where it is converted to a digital output signal. The digital signal is then read out by thin film transistors (TFI's) or fiber-coupled charge coupled devices (CODs). Direct FPDs include amorphous selenium (a-Se) FPDs that convert X-ray photons directly into charge. The outer layer of a flat panel in this design is typically a high-voltage bias electrode. X-ray photons create electron hole pairs in a-Se, and the transit of these electrons and holes depends on the potential of the bias voltage charge. As the holes are replaced with electrons, the resultant charge pattern in the selenium layer is read out by a TFT array, active matrix array, electrometer probes or micro plasma line addressing. Other direct digital detectors are based on CMOS and CCD technology. Phosphor detectors also may be employed to record the X-ray energy during exposure and is scanned by a laser diode to excite the stored energy which is released and read out by a digital image capture array of a CCD.

In examples, the AR control parameter may be a real-time user input, and different AR contents for overlaying via different AR devices may be determined based on user input. For example, a user interface may be presented for the user to select one or more AR content for displaying at the AR device. The hub may generate and send the AR content in accordance with the user selection.

Figure 36:
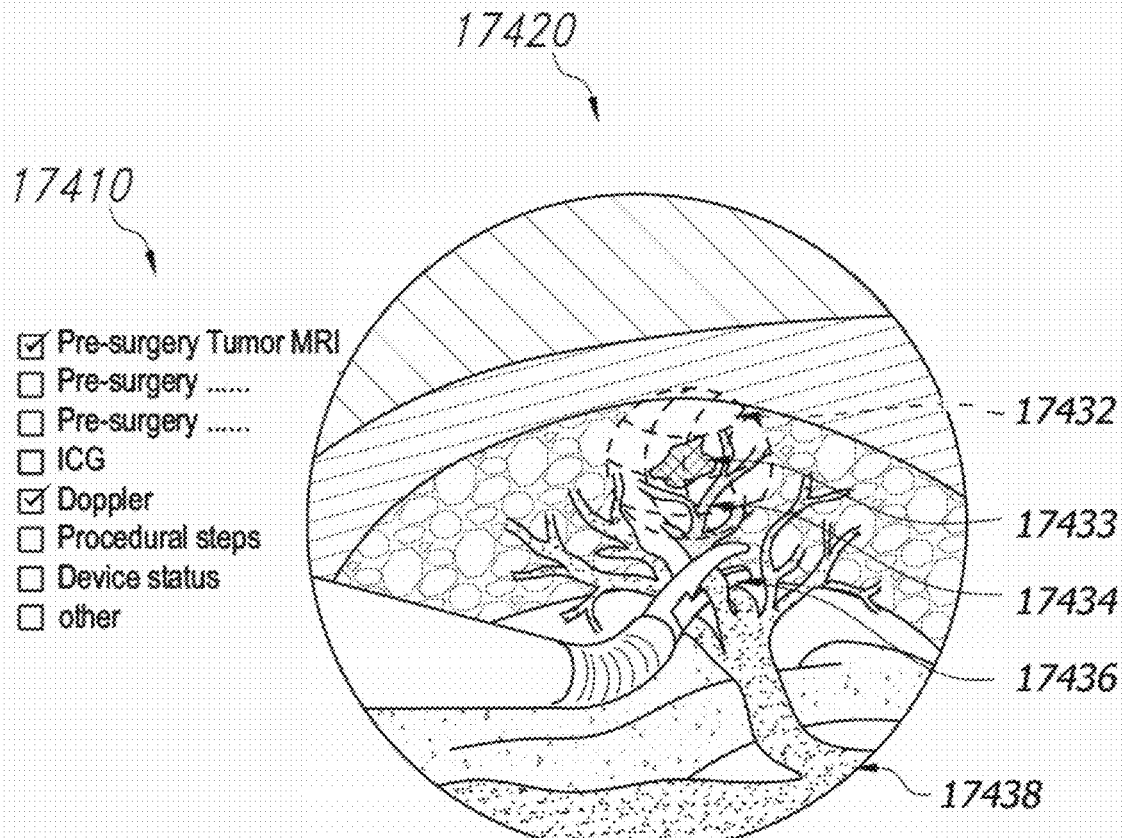
FIG. 36 illustrates an example of am augmented reality overlay for a targeted area with pre-surgery tumor data and real time doppler monitoring.

FIG. 36 illustrates an example of customizable AR content overlay. As shown, AR content options 17410 may be presented, for example, on an interactive display screen. AR content options 17410 may include available overlay layers, which can include pre-surgery tumor MRI, other relevant pre-surgery data, ICG data, real-time doppler monitoring, procedural steps, device status, and other overlays customizable by the users. The overlay layers may be provided by the hub. In this example, pre-surgery tumor data and real time doppler monitoring have been selected, and such data is included in the AR content to be overlaid on the surgical image. Through the AR device, the user may view vision 17420, which shows the two selected overlays: pre-surgery tumor MRI and real time Doppler monitoring. As shown, AR content may include marking the tumor 14733 and the tumor margin 17432. With the help of the overlay, the user can clamp jaws 17436 onto a vessel to verify if the vessel is within, or without tumor margins. AR content may indicate the blood flow of a vessel. For example, whether a vessel is associated with low blood flow or high blood flow may be indicated via color coding in the AR content. To illustrate, the AR content may include changing the low blood flow vessels 17434 to blue vessels, and changing high blood flow vessels 17438 to red.

The hub, in communication with the augmented reality device can provide simulation or confirmation of the intended action. The AR content may include an indication of a predicted outcome if user performs the intended action. As an example, if the user clamps or has the jaws over the intended area to staple, dissect, or seal, the AR content may indicate to the user the change of flow of fluids. This may provide guidance to the user to move in one direction or another. For example, the surgical hub may receive an indication of an intended action on a target area. The indication may include an image captured via a surgical scope indicating a surgical instrument being placed on or proximate to a target area. The indication may include an image captured via the AR device indicating a surgical instrument being placed on or proximate to a target area. For example, the AR content may be generated based on a microwave ablation confirmation, which can show the predicted output based on time and temperature. The surgical hub may receive visual input from the camera(s) in the OR, and sensor input from the surgical device(s) in the OR. The surgical hub may combine and compile the received inputs and generate confirmation and/or feedback of expected outcome for inclusion in the AR content. The hub may synthesize various data streams into a coherent output that can be overlay or shown on the displays, including the primary and/or the secondary displays, AR displays and/or non-AR displays. The surgical hub may obtain a predicted outcome associated with performing the intended action on the target area and may include the predicted outcome in the AR content. The predicted outcome may be determined based on visual data received from the surgical scope and surgical data received from the surgical instrument(s). The predicted outcome may be determined by the surgical hub, or with the help of a remote server. For example, the surgical hub may obtain visual data from a surgical scope and sensor input data from the at least one surgical instrument and send the visual data and the sensor input data to a remote server. The predicted outcome may be received from the remote server and included in the AR content for display at the AR device.

FIG. 44 shows an example flow of a hub operation under a visualization control with AR capabilities. The AR content for overlaying on a display may vary by the AR device. At 17711, the hub may obtain an AR control parameter as described herein. The AR control parameter may comprise at least one of: a user's role, a user's orientation relative to the first display, a progression of the surgical procedure, a surgical context, a real-time use input, or a preconfigured user preference. At 17712, the hub may obtain, from a surgical instrument, a data stream for displaying on a display. The data stream may be or may include video image(s) of a surgical site within a patient. The hub, at 17713, may determine, based on the AR control parameter, the AR content for overlaying on the data stream displayed on the display via a first AR device. An AR device for use by a surgeon may display AR content different than the AR content displayed via an AR device for use by a surgeon's assistant. An AR device with one preconfigured user preference may display AR content different than the AR content displayed via an AR device with a different preconfigured user preference. The AR content may include a step for use associated with a surgical instrument, a device setting, a device status, a device instruction for use, operation parameter(s), and/or an indication of a detected abnormality. The hub, at 17714, may determine, based on the AR control parameter, the AR content for overlaying on the data stream displayed on the display via a second AR device. At 17715, the hub, based on the determined AR contents for the respective AR devices for display, send the AR contents to the respective AR devices.

The invention claimed is:

1. A surgical hub comprising:
a communication array operably connected to a primary display and a secondary display, a laparoscopic scope and at least one surgical instrument; and
a processor configured to:
obtain a visualization control mode based on a visualization control parameter, wherein the visualization control parameter comprises available data bandwidth associated with the surgical hub;
generate first visualization data for the primary display;
determine whether to generate second visualization data for the secondary display based on the obtained visualization control mode, the second visualization data being different from the first visualization data, wherein the second visualization data for the secondary display is generated based on a determination that the available data bandwidth associated with the surgical hub is capable of supporting multi-display capabilities, and generation of the second visualization data for the secondary display is disabled based on a determination that the available data bandwidth associated with the surgical hub lacks capacity to support multi-display capabilities; and
send data for display on at least one of the primary display or the secondary display based on the determination.

2. The surgical hub of claim 1, wherein the visualization control parameter further comprises at least one of:
a hardware capability associated with the surgical hub, the primary display and the secondary display;
a software capability associated with the surgical hub, the primary display and the secondary display;
heat generated by the surgical hub; or
heat generated by the secondary display.

3. The surgical hub of claim 1, wherein the processor is further configured to:
receive an indication of changing the visualization control mode to an updated visualization control mode;
determine whether to generate the second visualization data for the secondary display based on the updated visualization control mode; and
send data for display on at least one of the primary display or the secondary display based on the updated determination.

4. The surgical hub of claim 1, wherein the processor is further configured to:
determine whether to generate the second visualization data based on a user role associated with the secondary display and the visualization control mode.

5. The surgical hub of claim 1, wherein the processor is further configured to:
determine whether to generate the second visualization data based on a contactless control parameter and the visualization control mode, wherein the contactless control parameter comprises at least one of: a detected user motion, a detected head orientation relative to a monitor, a detected user hand gesture, or a user voice activation.

6. The surgical hub of claim 1, wherein the processor is further configured to:
determine, based on the visualization control mode, whether to receive a visualization control indication that indicates a display change on at least one of the primary display or the secondary display; and
based on a determination to receive the visualization control indication, generate the first or second visualization data for display based on the display change indicated in the visualization control indication.

7. The surgical hub of claim 1, wherein the secondary display is an augmented reality device, and the processor is further configured to:
determine, based on the visualization control mode, whether to generate overlay information for overlaying on the primary display via the secondary display; and
based on a determination that the visualization control mode supports augmented reality, generate the overlay information, and overlay the overlay information on the primary display via the secondary display upon detecting a user of the secondary display viewing the primary display.

8. The surgical hub of claim 1, wherein the visualization control parameter further comprises a subscription level associated with surgical display, and the processor is further configured to:
generate the second visualization data for the secondary display based on a determination that the subscription level associated with surgical display indicates support for multi-display capabilities; and
disable generating the second visualization data for the secondary display based on a determination that the subscription level associated with surgical display does not support multi-display capabilities.

9. The surgical hub of claim 1, wherein the visualization control parameter further comprises a power capability associated with the surgical hub, and the processor is further configured to:
generate the second visualization data for the secondary display based on a determination that the power capability associated with the surgical hub is capable of supporting multi-display capabilities; and
disable generating the second visualization data for the secondary display based on a determination that the power capability associated with the surgical hub lacks capacity to support multi-display capabilities.

10. A method for a surgical hub operably connected to a primary display and a secondary display, a laparoscopic scope and at least one surgical instrument, the method comprising:
obtaining a visualization control mode based on a visualization control parameter, wherein the visualization control parameter comprises a free processing capability associated with the surgical hub;
generating first visualization data for the primary display;
determining whether to generate second visualization data for the secondary display based on the obtained visualization control mode, the second visualization data being different from the first visualization data, wherein the second visualization data for the secondary display is generated based on a determination that the free processing capability associated with the surgical hub is capable of supporting multi-display capabilities, and generation of the second visualization data for the secondary display is disabled based on a determination that the free processing capability associated with the surgical hub lacks capacity to support multi-display capabilities; and
sending data for display on at least one of the primary display or the secondary display based on the determination.

11. The method of claim 10, wherein the visualization control parameter further comprises at least one of:
a hardware capability associated with the surgical hub, the primary display and the secondary display;

a software capability associated with the surgical hub, the primary display and the secondary display;
a subscription level associated with surgical display;
a power capability associated with the surgical hub;
heat generated by the surgical hub; or
heat generated by the secondary display.

12. The method of claim 10, further comprising:
receiving, from a tiered control system, an indication of changing the visualization control mode to an updated visualization control mode; and
sending data for display on at least one of the primary display or the secondary display based on the updated visualization control mode.

13. The method of claim 10, further comprising:
determining whether to generate the second visualization data based on a contactless control parameter based on the visualization control mode, wherein the contactless control parameter comprises at least one of: a detected user motion, a detected head orientation relative to a monitor, a detected user hand gesture, or a user voice activation.

14. The method of claim 10, further comprising:
determining, based on the visualization control mode, whether to generate overlay information for overlaying on the primary display via the secondary display; and
based on a determination that the visualization control mode supports augmented reality, generating the overlay information, and overlay the overlay information on the primary display via the secondary display upon detecting a user of the secondary display viewing the primary display.

15. A surgical hub comprising:
a communication array operably connected to a primary display and a secondary display, a laparoscopic scope and at least one surgical instrument; and
a processor configured to:
obtain a visualization control mode based on a visualization control parameter, wherein the visualization control parameter comprises available memory associated with the surgical hub;
generate first visualization data for the primary display;
determine whether to generate second visualization data for the secondary display based on the obtained visualization control mode, the second visualization data being different from the first visualization data, wherein the second visualization data for the secondary display is generated based on a determination that the available memory associated with the surgical hub is capable of supporting multi-display capabilities, and generation of the second visualization data for the secondary display is disabled based on a determination that the available memory associated with the surgical hub lacks capacity to support multi-display capabilities; and
send data for display on at least one of the primary display or the secondary display based on the determination.

16. The surgical hub of claim 15, wherein the visualization control parameter further comprises at least one of:
a hardware capability associated with the surgical hub, the primary display and the secondary display;
a software capability associated with the surgical hub, the primary display and the secondary display;
heat generated by the surgical hub; or
heat generated by the secondary display.

17. The surgical hub of claim 15, wherein the processor is further configured to:
receive an indication of changing the visualization control mode to an updated visualization control mode;
determine whether to generate the second visualization data for the secondary display based on the updated visualization control mode; and
send data for display on at least one of the primary display or the secondary display based on the updated determination.

18. The surgical hub of claim 15, wherein the processor is further configured to:
determine whether to generate the second visualization data based on a user role associated with the secondary display and the visualization control mode.

19. The surgical hub of claim 15, wherein the processor is further configured to:
determine whether to generate the second visualization data based on a contactless control parameter and the visualization control mode, wherein the contactless control parameter comprises at least one of: a detected user motion, a detected head orientation relative to a monitor, a detected user hand gesture, or a user voice activation.

20. The surgical hub of claim 15, wherein the visualization control parameter further comprises a subscription level associated with surgical display, and the processor is further configured to:
generate the second visualization data for the secondary display based on a determination that the subscription level associated with surgical display indicates support for multi-display capabilities; and
disable generating the second visualization data for the secondary display based on a determination that the subscription level associated with surgical display does not support multi-display capabilities.

* * * * *